(12) United States Patent
Di Fabio et al.

(10) Patent No.: US 7,427,630 B2
(45) Date of Patent: Sep. 23, 2008

(54) CONDENSED N-HETEROCYCLIC COMPOUNDS AND THEIR USE AS CRF RECEPTOR ANTAGONISTS

(75) Inventors: Romano Di Fabio, Verona (IT); Fabio Maria Sabbatini, Verona (IT); Yves St-Denis, Verona (IT)

(73) Assignees: SB Pharmaco Puerto Rico Inc., San Juan, PR (US); Neurocrine Biosciences Inc., San Diego, CA (US)

( * ) Notice: Subject to any disclaimer, the term of this patent is extended or adjusted under 35 U.S.C. 154(b) by 0 days.

(21) Appl. No.: 10/552,493

(22) PCT Filed: Apr. 7, 2004

(86) PCT No.: PCT/IB2004/001350

§ 371 (c)(1),
(2), (4) Date: Sep. 21, 2006

(87) PCT Pub. No.: WO2004/094420

PCT Pub. Date: Nov. 4, 2004

(65) Prior Publication Data

US 2007/0004708 A1    Jan. 4, 2007

(30) Foreign Application Priority Data

Apr. 9, 2003 (GB) .................................. 0308208.8

(51) Int. Cl.
| A01N 43/42 | (2006.01) |
| A61K 31/44 | (2006.01) |
| C07D 471/02 | (2006.01) |
| C07D 491/02 | (2006.01) |
| C07D 498/02 | (2006.01) |

(52) U.S. Cl. ...................................... 514/300; 546/113
(58) Field of Classification Search ................. 546/113; 514/300

See application file for complete search history.

(56) References Cited

U.S. PATENT DOCUMENTS

| 5,006,530 A | 4/1991 | Angerbauer et al. ......... 514/277 |
| 5,120,782 A | 6/1992 | Hubsch et al. .............. 514/300 |
| 5,169,857 A | 12/1992 | Angerbauer et al. ........ 514/344 |
| 5,378,700 A | 1/1995 | Sakuma et al. ............. 514/212 |
| 5,401,746 A | 3/1995 | Angerbauer et al. ........ 514/277 |
| 5,502,187 A | 3/1996 | Ayer et al. .................. 544/117 |
| 5,955,613 A | 9/1999 | Horvath et al. ................. 546/87 |
| 5,962,479 A | 10/1999 | Chen .......................... 514/348 |
| 6,107,301 A | 8/2000 | Aldrich et al. .............. 514/258 |
| 6,133,282 A | 10/2000 | Horvath et al. .............. 514/292 |
| 6,355,651 B1 | 3/2002 | Horvath et al. .............. 514/292 |
| 6,436,932 B1 | 8/2002 | Ge et al. ................... 514/234.5 |
| 6,525,067 B1 | 2/2003 | Chen .......................... 514/311 |
| 2002/0111490 A1 | 8/2002 | Horvath et al. ................. 546/81 |
| 2004/0110785 A1 | 6/2004 | Wang et al. .................. 514/300 |
| 2004/0176400 A1 | 9/2004 | Capelli et al. ............ 514/264.11 |
| 2004/0198726 A1 | 10/2004 | DiFabio et al. ............. 514/230.2 |
| 2004/0235871 A1 | 11/2004 | DiFabio et al. .............. 514/267 |
| 2004/0242623 A1 | 12/2004 | DiFabio et al. .............. 514/292 |
| 2005/0054661 A1 | 3/2005 | DiFabio et al. ............. 514/265.1 |
| 2007/0021429 A1 | 1/2007 | Yves et al. |
| 2007/0287705 A1 | 12/2007 | Luo et al. .................. 514/228.5 |
| 2007/0293508 A1 | 12/2007 | Williams et al. ......... 514/255.05 |
| 2007/0293511 A1 | 12/2007 | Luo et al. .................. 514/259.3 |

FOREIGN PATENT DOCUMENTS

| DE | 4239440 | 11/1992 |
| EP | 325130 | 1/1989 |
| EP | 414767 | 8/1990 |
| EP | 0465970 | 6/1991 |
| EP | 729758 | 2/1996 |
| EP | 773023 A1 | 5/1997 |
| EP | 1040831 | 3/2000 |
| EP | 1103553 | 11/2000 |
| GB | 2248618 | 4/1992 |
| JP | 7010876 | 1/1995 |
| JP | 11335376 A | 12/1999 |
| JP | 2000086663 | 3/2000 |
| WO | WO 91/05784 A | 5/1991 |
| WO | WO 92/12718 | 8/1992 |
| WO | WO 93/20078 | 10/1993 |
| WO | WO 95/10506 | 4/1995 |
| WO | WO 95/34563 | 12/1995 |
| WO | WO 98/05661 | 2/1998 |
| WO | WO 98/08846 | 5/1998 |
| WO | WO 98/08847 | 5/1998 |
| WO | WO 98/35967 | 8/1998 |

(Continued)

OTHER PUBLICATIONS

Mulder et al., "Sandwich ELISA for glutathione S-transferase Alpha1-1: plasma concentrations in controls and in patients with gastrointestinal disorders", Clinical Chemistry, 1996, vol. 42, pp. 416-419.*

Primary Examiner—Margaret D. Seamani
Assistant Examiner—Niloofar Rahmani
(74) Attorney, Agent, or Firm—Laura K. Madden; Loretta J. Sauermelch; Mary E. McCarthy

(57) ABSTRACT

The present invention provides compounds of formula (I) including stereoisomers, prodrugs and pharmaceutically acceptable salts or solvates thereof to processes for their preparation, to pharmaceutical compositions containing them and to their use in the treatment of conditions mediated by corticotrophin-releasing factor (CRF).

18 Claims, No Drawings

FOREIGN PATENT DOCUMENTS

| | | |
|---|---|---|
| WO | WO 98/45295 | 10/1998 |
| WO | WO 99/07703 | 2/1999 |
| WO | WO 99/51599 | 10/1999 |
| WO | WO 00/058301 | 10/2000 |
| WO | WO 00/058307 | 10/2000 |
| WO | WO 00/058313 | 10/2000 |
| WO | WO 00/66585 | 11/2000 |
| WO | WO 01/23389 | 4/2001 |
| WO | WO 01/53263 | 7/2001 |
| WO | WO 02/02549 | 1/2002 |
| WO | WO 02/019975 | 3/2002 |
| WO | WO 02/055084 | 7/2002 |
| WO | WO 02/088095 | 11/2002 |
| WO | WO 02/100863 | 12/2002 |
| WO | WO 03/008412 | 1/2003 |
| WO | WO 03/022214 | 3/2003 |
| WO | WO 04/000843 | 12/2003 |
| WO | WO2004/062665 A1 | 7/2004 |
| WO | WO 05/063749 | 7/2005 |
| WO | WO 05/063755 | 7/2005 |
| WO | WO 05/063756 | 7/2005 |

* cited by examiner

CONDENSED N-HETEROCYCLIC COMPOUNDS AND THEIR USE AS CRF RECEPTOR ANTAGONISTS

This application is a 371 of International Application No. PCT/IB2004/001350, filed Apr. 7, 2004.

The present invention relates to bicyclic derivatives, to processes for their preparation, to pharmaceutical compositions containing them and to their use in therapy.

The first corticotropin-releasing factor (CRF) was isolated from ovine hypothalami and identified as a 41-amino acid peptide (Vale et al., Science 213: 1394-1397, 1981).

CRF has been found to produce profound alterations in endocrine, nervous and immune system function. CRF is believed to be the major physiological regulator of the basal and stress-release of adrenocorticotropic hormone ("ACTH"), Bendorphin and other propiomelanocortin ("POMC")-derived peptides from the anterior pituitary (Vale et al., Science 213: 1394-1397, 1981).

In addition to its role in stimulating the production of ACTH and POMC, CRF appears to be one of the pivotal central nervous system neurotransmitters and plays a crucial role in integrating the body's overall response to stress.

Administration of CRF directly to the brain elicits behavioral, physiological and endocrine responses identical to those observed for an animal exposed to a stressful environment. Accordingly, clinical data suggests that CRF receptor antagonists may represent novel antidepressant and/or anxiolytic drugs that may be useful in the treatment of the neuropsychiatric disorders manifesting hypersecretion of CRF.

The first CRF receptor antagonists were peptides (see, e.g., Rivier et al., U.S. Pat. No. 4,605,642; Rivier et al., Science 224: 889, 1984). While these peptides established that CRF receptor antagonists can attenuate the pharmacological responses to CRF, peptide CRF receptor antagonists suffer from the usual drawbacks of peptide therapeutics including lack of stability and limited oral activity. More recently, small molecule CRF receptor antagonists have been reported.

WO 95/10506 describes inter alia compounds of general formula (A) with general CRF antagonist activity

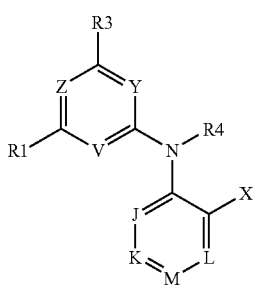

wherein Y may be CR29; V may be nitrogen, Z may be carbon or nitrogen, R3 may correspond to an amine derivative and R4 may be taken together with R29 to form a 5-membered ring and is CH(R28) when R29 is CH(R30).

WO 95/33750 also describes compounds of general formula (B) having CRF antagonistic activity,

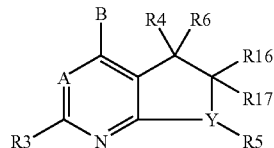

in which A and Y may be nitrogen and carbon and B may correspond to an amine derivative.

Recently a patent application has been published as WO 02/08895 in which the following compounds, CRF antagonists, are objects of the Patent Application:

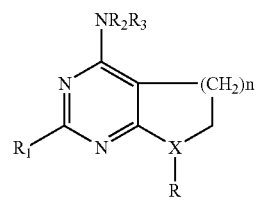

In particular, $R_2$ and $R_3$ with N may form a saturated or unsaturated heterocycle, which may be substituted by a 5-6 membered heterocycle, which may be substituted by 1 to 3 groups selected among: C1-C6 alkyl, halo C1-C2 alkyl, C1-C6 alkoxy, halogen, nitro or cyano.

Another recent patent application has been published as WO 03/008412 in which the following compounds, CRF antagonists, are objects of the Patent Application:

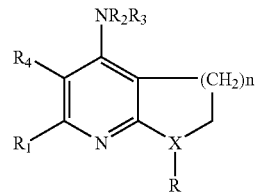

In particular, $R_2$ and $R_3$ with N may form a 5-14 membered heterocycle, which may be substituted by a 5-6 membered heterocycle, which may be saturated or may contain one to three double bonds, and which may be substituted by 1 or more groups such as C3-C7 cycloalkyl, C1-C6 alkyl, C1-C6 alkoxy, halo C1-C6 alkyl, C2-C6 alkenyl, C2-C6 alkynyl, halo C1-C6 alkoxy, hydroxy, halogen, nitro, cyano, or C(O)$NR_6R_7$.

None of the above references disclosed compounds falling into the scope of the present invention.

Due to the physiological significance of CRF, the development of biologically-active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

While significant strides have been made toward achieving CRF regulation through administration of CRF receptor antagonists, there remains a need in the art for effective small molecule CRF receptor antagonists. There is also a need for pharmaceutical compositions containing such CRF receptor antagonists, as well as methods relating to the use thereof to treat, for example, stress-related disorders. The present invention fulfills these needs, and provides other related advantages.

In particular the invention relates to novel compounds which are potent and specific antagonists of corticotropin-releasing factor (CRF) receptors.

The present invention provides compounds of formula (I) including stereoisomers, prodrugs and pharmaceutically acceptable salts or solvates thereof

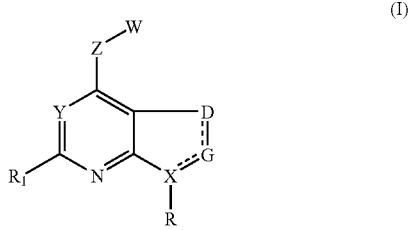

wherein
the dashed line may represent a double bond;
R is aryl or heteroaryl, each of which may be substituted by 1 to 4 groups J selected from:
  halogen, C1-C6 alkyl, C1-C6 alkoxy, halo C1-C6 alkyl, C2-C6 alkenyl, C2-C6 alkynyl, halo C1-C6 alkoxy, C(O)R$_2$, nitro, hydroxy, NR$_3$R$_4$, cyano or a group Z;
R$_1$ is hydrogen, C3-C7 cycloalkyl, C1-C6 alkyl, C1-C6 alkoxy, C1-C6 thioalkyl, C2-C6 alkenyl, C2-C6 alkynyl, halo C1-C6 alkyl, halo C1-C6 alkoxy, halogen, NR$_3$R$_4$ or cyano;
R$_2$ is a C1-C4 alkyl, OR$_3$ or NR$_3$R$_4$;
R$_3$ is hydrogen or C1-C6 alkyl;
R$_4$ is hydrogen or C1-C6 alkyl;
R$_5$ is a C1-C6 alkyl, halo C1-C6 alkyl, C1-C6 alkoxy, halo C1-C6 alkoxy, C3-C7 cycloalkyl, hydroxy, halogen, nitro, cyano, NR$_3$R$_4$; C(O)R$_2$;
R$_6$ is a C1-C6 alkyl, halo C1-C6 alkyl, C1-C6 alkoxy, halo C1-C6 alkoxy, C3-C7 cycloalkyl, hydroxy, halogen, nitro, cyano, NR$_3$R$_4$; C(O)R$_2$;
R$_7$ is hydrogen, C1-C6 alkyl, halogen or halo C1-C6 alkyl;
R$_8$ is hydrogen, C3-C7 cycloalkyl, C1-C6 alkyl, C2-C6 alkenyl, C2-C6 alkynyl, NR$_3$R$_4$ or cyano;
R$_9$ is hydrogen, C3-C7 cycloalkyl, C1-C6 alkyl, C2-C6 alkenyl, C2-C6 alkynyl, NR$_3$R$_4$ or cyano;
R$_{10}$ is hydrogen, C3-C7 cycloalkyl, C1-C6 alkyl, C2-C6 alkenyl, C2-C6 alkynyl, NR$_3$R$_4$ or cyano;
R$_{11}$ is hydrogen, C3-C7 cycloalkyl, C1-C6 alkyl, C2-C6 alkenyl, C2-C6 alkynyl, NR$_3$R$_4$ or cyano;
R$_{12}$ is R$_3$ or C(O)R$_2$;
D is CR$_8$R$_9$ or is CR$_8$ when double bonded with G;
G is CR$_{10}$R$_{11}$ or is CR$_{10}$ when double bonded with D or is CR$_{10}$ when double bonded with X when X is carbon;
X is carbon or nitrogen;
Y is nitrogen or CR$_7$;
W is a 4-8 membered ring, which may be saturated or may contain one to three double bonds, and
in which:
  one carbon atom is replaced by a carbonyl or S(O)$_m$; and
  one to four carbon atoms may optionally be replaced by oxygen, nitrogen or NR$_{12}$, S(O)$_m$, carbonyl, and such ring may be further substituted by 1 to 8 R$_6$ groups;

Z is a 5-6 membered heterocycle, which may be substituted by 1 to 8 R$_5$ groups or a phenyl ring, which may be substituted by 1 to 4 R$_5$ groups;
m is an integer from 0 to 2.

The compounds of the present invention may be in the form of and/or may be administered as a pharmaceutically acceptable salt. For a review on suitable salts see Berge et al, J. Pharm. Sci., 1977, 66, 1-19.

Typically, a pharmaceutical acceptable salt may be readily prepared by using a desired acid or base as appropriate. The salt may precipitate from solution and be collected by filtration or may be recovered by evaporation of the solvent.

Suitable addition salts are formed from acids which form non-toxic salts and examples are hydrochloride, hydrobromide, hydroiodide, sulphate, bisulphate, nitrate, phosphate, hydrogen phosphate, acetate, maleate, malate, fumarate, lactate, tartrate, citrate, formate, gluconate, succinate, piruvate, oxalate, oxaloacetate, trifluoroacetate, saccharate, benzoate, methansulphonate, ethanesulphonate, benzenesulphonate, p-toluensulphonate, methanesulphonic, ethanesulphonic, p-toluenesulphonic, and isethionate.

Pharmaceutically acceptable base salts include ammonium salts, alkali metal salts such as those of sodium and potassium, alkaline earth metal salts such as those of calcium and magnesium and salts with organic bases, including salts of primary, secondary and tertiary amines, such as isopropylamine, diethylamine, ethanolamine, trimethylamine, dicyclohexyl amine and N-methyl-D-glucamine.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention.

In addition, prodrugs are also included within the context of this invention.

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

With regard to stereoisomers, the compounds of structure (I) may have one or more asymmetric carbon atom and may occur as racemates, racemic mixtures and as individual enantiomers or diastereomers. All such isomeric forms are included within the present invention, including mixtures thereof.

Where a compound of the invention contains an alkenyl or alkenylene group, cis (E) and trans (Z) isomerism may also occur. The present invention includes the individual stereoisomers of the compound of the invention and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent may also be prepared from a corresponding optically pure intermediate or by resolution, such as H.P.L.C. of the corresponding racemate using a suitable chiral support or by fractional crystallisation of the diastereoisomeric salts formed by reaction of the corresponding racemate with a suitable optically active acid or base, as appropriate.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compounds of the invention are within the scope of the invention.

Furthermore, some of the crystalline forms of the compounds of structure (I) may exist as polymorphs, which are included in the present invention.

The term C1-C6 alkyl as used herein as a group or a part of the group refers to a linear or branched alkyl group containing from 1 to 6 carbon atoms; examples of such groups include methyl, ethyl, propyl, isopropyl, n-butyl, isobutyl, tert butyl, pentyl or hexyl.

The term C3-C7 cycloalkyl group means a non aromatic monocyclic hydrocarbon ring of 3 to 7 carbon atom such as, for example, cyclopropyl, cyclobutyl, cyclopentyl, cyclohexyl or cycloheptyl; while unsaturated cycloalkyls include cyclopentenyl and cyclohexenyl, and the like.

The term halogen refers to a fluorine, chlorine, bromine or iodine atom.

The term halo C1-C6 alkyl, or halo C1-C2 alkyl means an alkyl group having one or more carbon atoms and wherein at least one hydrogen atom is replaced with halogen such as for example a trifluoromethyl group and the like.

The term C1-C6 thioalkyl may be a linear or a branched chain thioalkyl group, for example thiomethyl, thioethyl, thiopropyl, thioisopropyl, thiobutyl, thiosec-butyl, thiotert-butyl and the like.

The term C2-C6 alkenyl defines straight or branched chain hydrocarbon radicals containing one or more double bond and having from 2 to 6 carbon atoms such as, for example, ethenyl, 2-propenyl, 3-butenyl, 2-butenyl, 2-pentenyl, 3-pentenyl, 3-methyl-2-butenyl or 3-hexenyl and the like.

The term C1-C6 alkoxy group may be a linear or a branched chain alkoxy group, for example methoxy, ethoxy, propoxy, prop-2-oxy, butoxy, but-2-oxy or methylprop-2-oxy and the like.

The term halo C1-C6 alkoxy group may be a C1-C6 alkoxy group as defined before substituted with at least one halogen, preferably fluorine, such as $OCHF_2$, or $OCF_3$.

The term C2-C6 alkynyl defines straight or branched chain hydrocarbon radicals containing one or more triple bond and having from 2 to 6 carbon atoms including acetylenyl, propynyl, 1-butynyl, 1-pentynyl, 3-methyl-1-butynyl and the like.

The term aryl means an aromatic carbocyclic moiety such as phenyl, biphenyl or naphthyl.

The term heteroaryl means an aromatic heterocycle ring of 5 to 10 members and having at least one heteroatom selected from nitrogen, oxygen and sulfur, and containing at least 1 carbon atom, including both mono- and bicyclic ring systems.

Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, triazolyl, tetrazolyl, quinazolinyl, and benzodioxolyl.

The term 5-6 membered heterocycle means, according to the above definition, a 5-6 monocyclic heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized. Heterocycles include heteroaryls as defined above. The heterocycle may be attached via any heteroatom or carbon atom. Thus, the term include (but are not limited to) morpholinyl, pyridinyl, pyrazinyl, pyrazolyl, thiazolyl, triazolyl, imidazolyl, oxadiazolyl, oxazolyl, isoxazolyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydropyrimidinyl, tetrahydrothiophenyl, tetrahydrothiopyranyl, and the like.

The term W defines a 4-8 membered ring, which may be saturated or may contain from one to three double bonds, and in which:

one carbon atom is replaced by a carbonyl or $S(O)_m$; and one to four carbon atoms may optionally be replaced by oxygen, nitrogen or $NR_{12}$, $S(O)_m$, carbonyl, and such ring may be further substituted by 1 to 8 $R_6$ groups;

The 4-8 membered ring means a 4-8 monocyclic carbocyclic ring which is either saturated, or unsaturated o aromatic and one to four carbon atoms may be replaced by an heteroatom as defined above. The carbocycle may be attached via any heteroatom or carbon atom. Thus, the term include (but are not limited to): cyclobutane, cyclopentane, cyclohexane, cycloheptane, cyclooctane, azirydinyl, azetidinyl, pyrrolidinyl, piperidinyl, imidazolidinyl, morpholinyl, piperazinyl, hydantoinyl, valerolactamyl, oxetanyl, tetrahydrofuranyl, tetrahydropyranyl, tetrahydropyridinyl, tetrahydropyrimidinyl, tetrahydrothiophenyl, tetrahydrothiopyranyl, 1,3-dihydro-2H-imidazol-2-one, imidazolidin-2-one, tetrahydropyrimidin-2(1H)-one, 2,5-dihydro-1,2,5-thiadiazole 1-oxide, 1,2,5-thiadiazolidine 1-oxide, 2,5-dihydro-1,2,5-thiadiazole 1,1-dioxide, 1,2,6-thiadiazinane 1-oxide, pyrrolidin-2-one, 2,5-dihydro-1,2,5-thiadiazolidine 1,1-dioxide, 1,3-oxazolidin-2-one derivative, isothiazolidine 1,1-dioxide, 2(1H-pyridinone, 3(2H)-pyridazinone, 2,3-piperazinedione and the like.

Representative ring of the W definition include, but are not limited to, the following structure and derivatives:

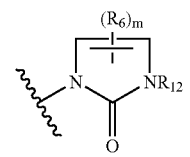
W1

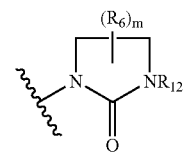
W2

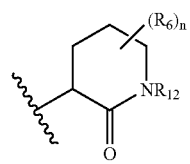
W3

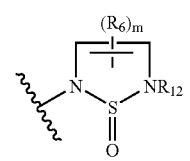
W4

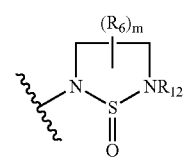
W5

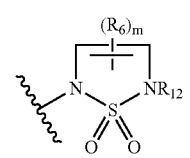
W6

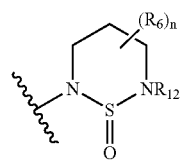
W7

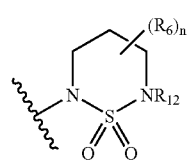
W8

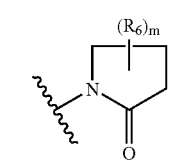
W9

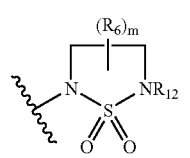
W10

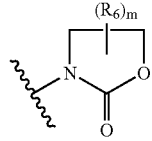
W11

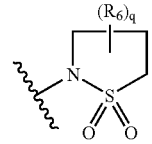
W12

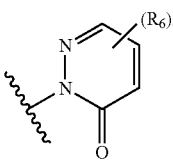
W13

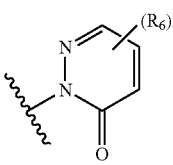
W14

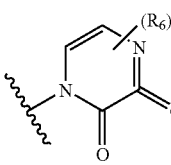
W15 in which:

W1 represents a 1,3-dihydro-2H-imidazol-2-one derivative;

W2 represents a imidazolidin-2-one derivative;

W3 represents a tetrahydropyrimidin-2(1H)-one derivative;

W4 represents a 2,5-dihydro-1,2,5-thiadiazole 1-oxide derivative;

W5 represents a 1,2,5-thiadiazolidine 1-oxide derivative;

W6 represents a 2,5-dihydro-1,2,5-thiadiazole 1,1-dioxide derivative;

W7 represents a 1,2,6-thiadiazinane 1-oxide derivative;

W8 represents a 1,2,6-thiadiazinane 1,1-dioxide derivative;

W9 represents a pyrrolidin-2-one derivative;

W10 represents a 2,5-dihydro-1,2,5-thiadiazolidine 1,1-dioxide derivative;

W11 represents a 1,3-oxazolidin-2-one derivative;

W12 represents a isothiazolidine 1,1-dioxide derivative;

W13 represents a 2(1H)-pyridinone derivative;

W14 represents a 3(2H)-pyridazinone;

W15 represents a 2,3-piperazinedione derivative;

and q is an integer from 0 to 4, n is an integer from 0 to 6, p is an integer from 0 to 3 and m, R6 and R12 are defined as above.

The compounds of formula (II) and (IIa) are representatives of the present invention.

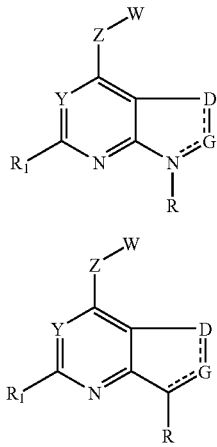 (II)

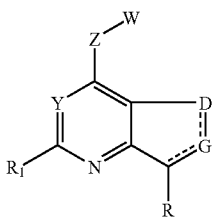 (IIa)

In particular they correspond to compounds (I) in which X is nitrogen or carbon and R, R1, Y, Z, W, D, and G have the meanings as previously defined.

The compounds of formula (II) are specific representatives of the present invention.

Particularly preferred are the compounds of formula (II), in which W is selected in the group consisting from: W1, W2, W3, W9, W10, W11, W12, W13, and W14.

Equally preferred are the compounds of formula (II), in which Z is selected in a group consisting from: pyrimidine, pyridine, thiazol, pyrazol, triazol and phenyl.

Equally preferred are the compounds of formula (II), in which W is selected in the group consisting from: W1, W2, W3, W9, W10, W11, W12, W13, and W14 and in which Z is selected in a group consisting from: pyrimidine, pyridine, thiazol, pyrazol, triazol and phenyl.

Examples of compounds of formula (II) are reported in the Experimental Part.

The compounds of formula (IIb), (IIc), (IId), (IIe), (IIf), (IIg), (IIh), (IIi), (IIl), (IIm), (IIn), (IIo), (IIp) and (IIq) are illustratives of the compounds of formula (II).

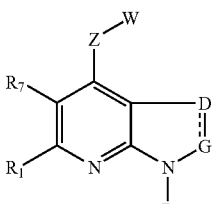 (IIb)

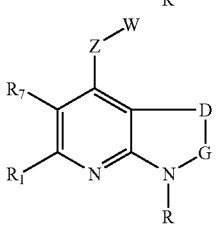 (IIc)

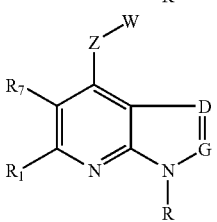 (IId)

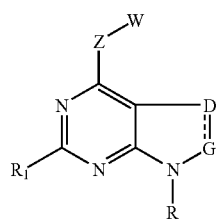 (IIe)

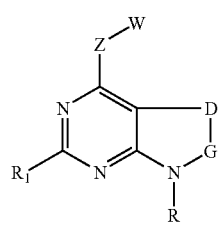 (IIf)

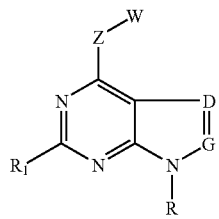 (IIg)

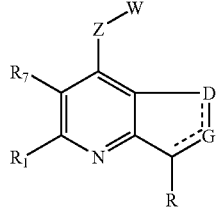 (IIh)

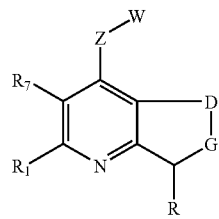 (IIi)

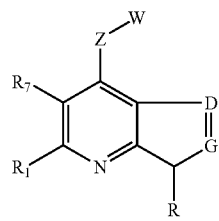 (IIl)

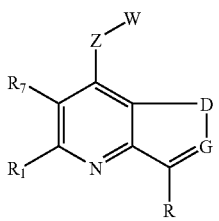 (IIm)

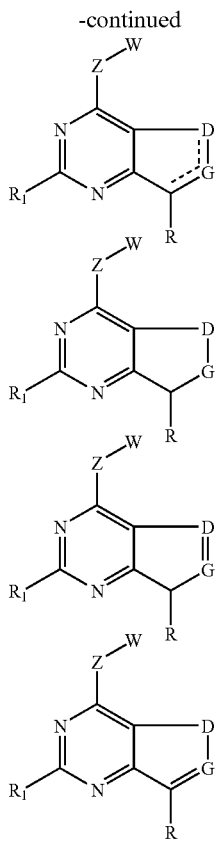

(IIn)

(IIo)

(IIp)

(IIq)

They correspond to the compounds of formula (II), depending on the meaning of X and Y, and where R, R1, R7, Z, W, D, and G have the meanings as previously defined.

Particularly preferred are the compounds of formula (IIb), (IIc), (IId), (IIe), (IIf), (IIg), (IIh), (IIi), (III), (IIm), (IIn), (IIo), (IIp) and (IIq) in which W is selected in the group consisting from: W1, W2, W3, W9, W10, W11, W12, W13, and W14.

Equally preferred are the compounds of formula (IIb), (IIc), (IId), (IIe), (IIf), (IIg), (IIh), (IIi), (III), (IIm), (IIn), (IIo), (IIp) and (IIq) in which Z is selected in a group consisting from: pyrimidine, pyridine, thiazol, pyrazol, triazol and phenyl.

Equally preferred are the compounds of formula (IIb), (IIc), (IId), (IIe), (IIf), (IIg), (IIh), (IIi), (III), (IIm), (IIn), (IIo), (IIp) and (IIq) in which W is selected in the group consisting from: W1, W2, W3, W9, W10, W11, W12, W13, and W14 and in which Z is selected in a group consisting from: pyrimidine, pyridine, thiazol, pyrazol, triazol and phenyl.

The compounds of formula (IIr), (IIs) and (IIt), which correspond to the compounds of formula (II) in which D and G are CH$_2$ are preferred.

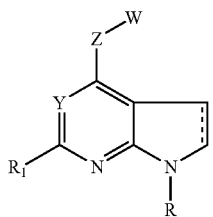

(IIr)

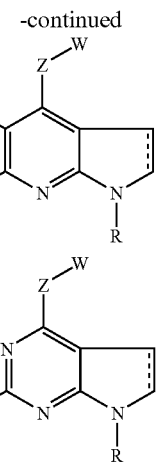

(IIs)

(IIt)

Particularly preferred are the compounds of formula (IIr), (IIs) and (IIt), in which W is selected in the group consisting from: W1, W2, W3, W9, W10, W11, W12, W13, and W14.

Equally preferred are the compounds of formula (IIr), in which Z is selected in a group consisting from: pyrimidine, pyridine, thiazol, pyrazol, triazol and phenyl.

Equally preferred are the compounds of formula (IIr), (IIs) and (IIt), in which W is selected in the group consisting from: W1, W2, W3, W9, W10, W11, W12, W13, and W14 and in which Z is selected in a group consisting from: pyrimidine, pyridine, thiazol, pyrazol, triazol and phenyl.

In particular, the compounds of formula (III) are representatives of the compounds of formula (II).

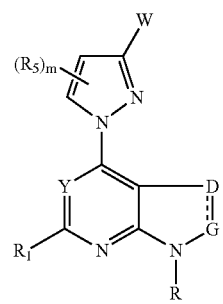

(III)

They correspond to the compounds of formula (II), in which Z is a pyrazolyl derivative and R, $R_1$, $R_5$, Y, W, D, m and G have the meanings as previously defined and the dashed line may represent a double bond.

The compounds of formula (IIIa), (IIIb), (IIIc) and (IIId) are specific representatives of the compounds of formula (III).

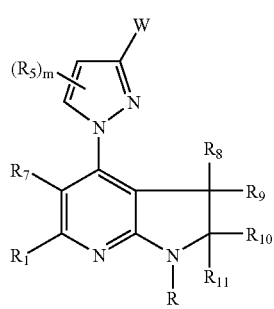

(IIIa)

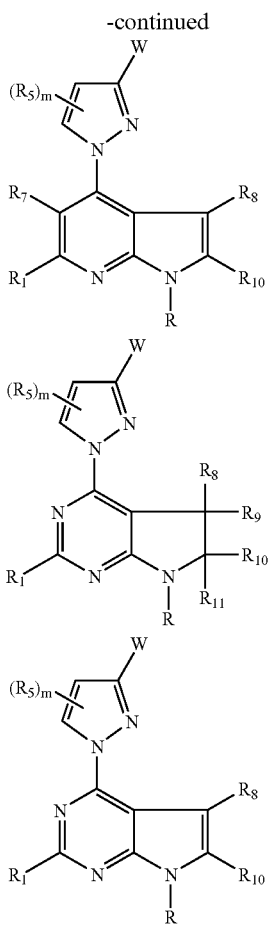

(IIIb)

(IIIc)

(IIId)

They correspond to the compounds of formula (III) depending on the meaning of Y, in which R, $R_1$, $R_5$, $R_7$, $R_8$, $R_9$, $R_{10}$, $R_{11}$, W, D, m and G have the meanings as previously defined.

Particularly preferred are the compounds of formula (IIIa), (IIIb), (IIIc) and (IIId), in which W is selected in the group consisting from: W1, W2, W3, W9, W10, W11, W12, W13, and W14 and R, $R_1$, $R_5$, $R_7$, $R_8$, $R_9$, $R_{10}$, $R_{11}$, m, have the meanings as previously defined.

In particular, the compounds of formula (IV) are representatives of the compounds of formula (III).

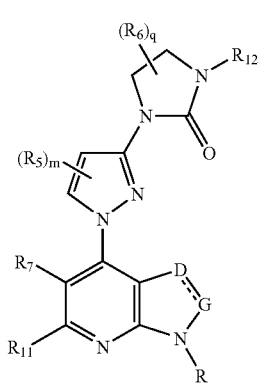

(IV)

They correspond to compounds of formula (III), in which W corresponds to a W2 derivative and R, $R_1$, $R_5$, $R_6$, $R_7$, $R_{12}$, m, q, D and G have the meanings as previously defined and the dashed line may represent a double bond.

The compounds of formula (IVa), (IVb) and (IVc) are specific representatives of the compound of formula (IV)

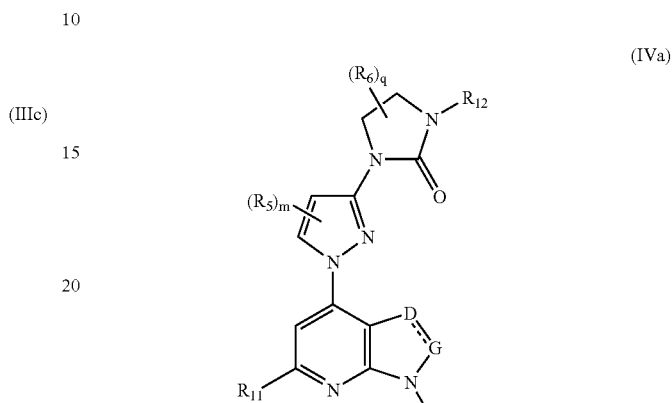

(IVa)

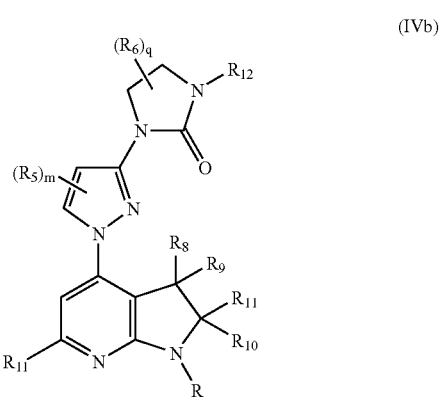

(IVb)

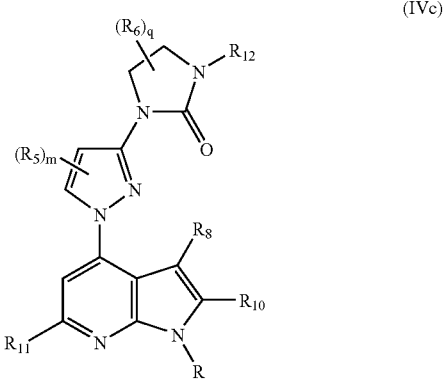

(IVc)

They correspond to the compounds of formula (IV), in which $R_7$ is hydrogen and R, $R_1$, $R_5$, $R_6$, $R_7$, $R_{12}$, m, q, D and G have the meanings as previously defined and the dashed line may represent a double bond.

The compounds of formula (V) are equally representatives of the compounds of formula (II).

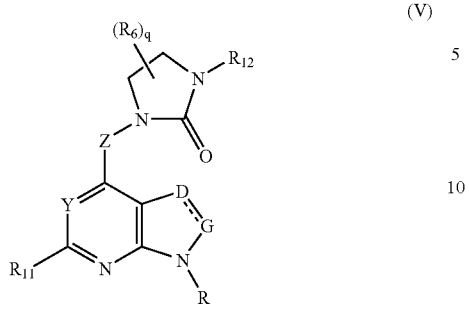

(V)

They correspond to the compounds of formula (II), in which W is a W2 derivative and Z, R, $R_1$, $R_6$, q, Y, W, D and G have the meanings as previously defined and the dashed line may represent a double bond.

The compounds of formula (VI) are specific representatives of the compounds of formula (V), in which Y is $CR_7$ and Z, R, $R_1$, $R_6$, $R_7$, q, Y, W, D and G have the meanings as previously and the dashed line may represent a double bond.

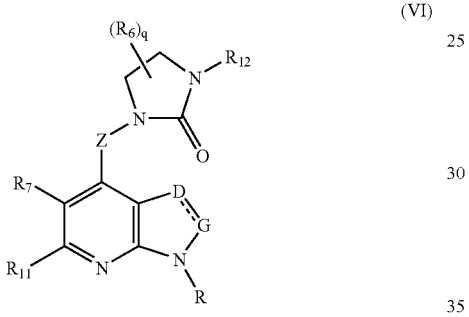

(VI)

The compounds of formula (VIa), (VIb) and (VIc) are specific representatives of the compound of formula (VI)

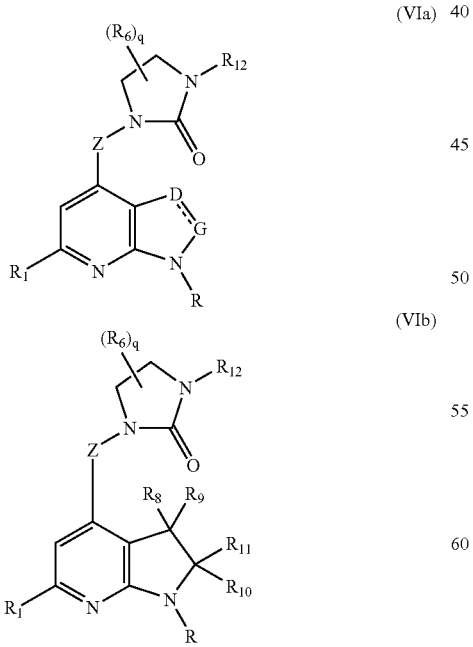

(VIa)

(VIb)

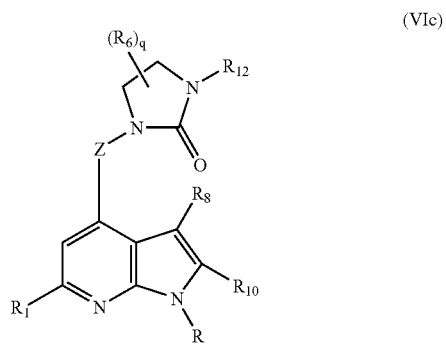

(VIc)

They correspond to the compounds of formula (VI) in which R7 is hydrogen and R, $R_1$, $R_6$, $R_8$, $R_9$, $R_{10}$, $R_{11}$, $R_{12}$, q, D and G have the meanings as previously defined and the dashed line may represent a double bond.

Particularly preferred are the compounds of formula (VIa), (VIb) and (VIc), in which Z is selected in a group consisting from: pyrimidine, pyridine, thiazol, pyrazol, triazol and phenyl and R, $R_1$, $R_6$, $R_8$, $R_9$, $R_{10}$, $R_{11}$, $R_{12}$, q, D and G have the meanings as previously defined.

Even more preferred embodiments of the invention include, but are not limited to, compounds of the formula (I), (IIb), (IIc), (IId), (IIe), (IIf), (IIg), (IIh), (IIi), (III), (IIm), (IIn), (IIo), (IIp), (IIq), (III), (IIIa), (IIIb), (IIIc), (IIId), (IV), (IVa), (IVb), (IVc), (V), (VI), (VIa), (VIb), (VIc) wherein:

$R_1$ is C1-C3 alkyl group or halo C1-C3 alkyl group, preferably methyl or trifluoromethyl;

$R_7$ is hydrogen;

$R_8$, ($R_9$), $R_{10}$ ($R_{11}$) are hydrogen;

R is an aryl group selected from: 2,4-dichlorophenyl, 2-chloro-4-methylphenyl, 2-chloro-4-trifluoromethylphenyl, 2-chloro-4-methoxyphenyl, 2,4,5-trimethylphenyl, 2,4-dimethylphenyl, 2-methyl-4-methoxyphenyl, 2-methyl-4-ethoxyphenyl, 2-methyl-4-isopropoxyphenyl, 2-methyl-4-hydroxyphenyl, 2-methyl-4-chlorophenyl, 2-methyl-4-trifluoromethylphenyl, 2,4-dimethoxyphenyl, 2-methoxy-4-trifluoromethylphenyl, 2-methoxy-4-chlorophenyl, 3-methoxy-4-chlorophenyl, 2,5-dimethoxy-4-chlorophenyl, 2-methoxy-4-isopropylphenyl, 2-methoxy-4-trifluoromethylphenyl, 2-methoxy-4-isopropylphenyl, 2-methoxy-4-methylphenyl, 2-trifluoromethyl-4-chlorophenyl, 2,4-bis-trifluoromethylphenyl, 2-trifluoromethyl-4-methylphenyl, 2-trifluoromethyl-4-methoxyphenyl, 2-difluoromethyl-4-methoxyphenyl, 2-bromo-4-isopropylphenyl, 2-methyl-4-cyanophenyl, 2-chloro-4-cyanophenyl, 2-trifluoromethyl-4-cyanophenyl, 2-trifluoromethoxy-4-cyanophenyl, 2-ethyl-4-cyanophenyl, 2-methyl-4-trifluoromethoxyphenyl, 4-methyl-6-dimethylaminopyridin-3-yl, 2,6-bismethoxy-pyridin-3-yl, 2-methyl-6-methoxy-pyridin-3-yl, 2-trifluoromethyl-6-methoxy-pyridin-3-yl 3-chloro-5-trichloromethyl-pyridin-2-yl, 2-methyl-4-(pyrazol-1-yl)-phenyl, 2-methoxy-4-

(pyrazol-1-yl)-phenyl, 2,4,6-trimethoxyphenyl, 2-methyl-4,5-benzodioxolyl, 2-methyl-3,4-benzodioxolyl.

Preferred compounds according to the invention are:

1-{-1-[1-(4-Methoxy-2-methylphenyl)-6-methyl-2,3-dihydro-1H-pyrrolo[2,3-b]pyridin-4-yl]-1H-pyrazol-3-yl}imidazolidin-2-one (compound 1-1);

1-{-[1-(4-Methoxy-2-methylphenyl)-6-methyl-2,3-dihydro-1H-pyrrolo[2,3-b]pyridin-4-yl]-1H-pyrazol-3-yl}-3-methylimidazolidin-2-one (compound 1-2);

1-{1-[1-(2,4-Dichlorophenyl)-6-methyl-2,3-dihydro-1H-pyrrolo[2,3-b]pyridin-4-yl]-1H-pyrazol-3-yl}imidazolidin-2-one (compound 1-3);

1-(1-{1-[2,4-Bis(trifluoromethyl)phenyl]-6-methyl-2,3-dihydro-1H-pyrrolo[2,3-b]pyridin-4-yl}-1H-pyrazol-3-yl)-2-imidazolidinone (compound 1-4);

1-{1-[1-(4-Hydroxy-2-methylphenyl)-6-methyl-2,3-dihydro-1H-pyrrolo[2,3-b]pyridin-4-yl]-1H-pyrazol-3-yl}-2-imidazolidinone (compound 1-5);

1-Acetyl-3-(1-{6-methyl-1-[2-methyl-4-(methyloxy)phenyl]-2,3-dihydro-1H-pyrrolo[2,3-b]pyridin-4-yl}-1H-pyrazol-3-yl)-2-imidazolidinone (compound 1-5);

1-Acetyl-3-(1-{6-methyl-1-[2-methyl-4-(methyloxy)phenyl]-2,3-dihydro-1H-pyrrolo-[2,3-b]pyridin-4-yl}-1H-pyrazol-3-yl)-2-imidazolidinone (compound 1-6);

1-(1-{1-[4-(Ethyloxy)-2-methylphenyl]-6-methyl-2,3-dihydro-1H-pyrrolo[2,3-b]pyridin-4-yl}-1H-pyrazol-3-yl)-2-imidazolidinone (compound 1-7);

1-[1-(6-Methyl-1-{2-methyl-4-[(1-methylethyl)oxy]phenyl}-2,3-dihydro-1H-pyrrolo[2,3-b]pyridin-4-yl)-1H-pyrazol-3-yl]-2-imidazolidinone (compound 1-8);

1-[1-(6-Methyl-1-{2-methyl-4-[(trifluoromethyl)oxy]phenyl}-2,3-dihydro-1H-pyrrolo[2,3-b]pyridin-4-yl)-1H-pyrazol-3-yl]-2-imidazolidinone (compound 1-9);

3-Methyl-4-{6-methyl-4-[3-(2-oxo-1-imidazolidinyl)-1H-pyrazol-1-yl]-2,3-dihydro-1H-pyrrolo[2,3-b]pyridin-1-yl}benzonitrile (compound 1-10);

1-(1-{6-Methyl-1-[2-methyl-4-(1H-pyrazol-1-yl)phenyl]-2,3-dihydro-1H-pyrrolo[2,3-b]pyridin-4-yl}-1H-pyrazol-3-yl)-2-imidazolidinone (compound 1-11);

4-{6-Methyl-4-[3-(2-oxo-1-imidazolidinyl)-1H-pyrazol-1-yl]-2,3-dihydro-1H-pyrrolo[2,3-b]pyridin-1-yl}-3-(trifluoromethyl)benzonitrile (compound 1-12);

1-(1-{1-[2-(Difluoromethyl)-4-(methyloxy)phenyl]-6-methyl-2,3-dihydro-1H-pyrrolo[2,3-b]pyridin-4-yl}-1H-pyrazol-3-yl)-2-imidazolidinone (compound 1-13);

4-{6-Methyl-4-[3-(2-oxo-1-imidazolidinyl)-1H-pyrazol-1-yl]-2,3-dihydro-1H-pyrrolo[2,3-b]pyridin-1-yl}-3-[(trifluoromethyl)oxy]benzonitrile (compound 1-14);

3-Ethyl-4-{6-methyl-4-[3-(2-oxo-1-imidazolidinyl)-1H-pyrazol-1-yl]-2,3-dihydro-1H-pyrrolo[2,3-b]pyridin-1-yl}benzonitrile (compound 1-15);

1-(1-{6-Methyl-1-[2-(methyloxy)-4-(1H-pyrazol-1-yl)phenyl]-2,3-dihydro-1H-pyrrolo[2,3-b]pyridin-4-yl}-1H-pyrazol-3-yl)-2-imidazolidinone (compound 1-16);

1-{1-[6-Methyl-1-(6-methyl-1,3-benzodioxol-5-yl)-2,3-dihydro-1H-pyrrolo[2,3-b]pyridin-4-yl]-1H-pyrazol-3-yl}-2-imidazolidinone (compound 1-17);

1-(1-{6-Methyl-1-[2,4,6-tris(methyloxy)phenyl]-2,3-dihydro-1H-pyrrolo[2,3-b]pyridin-4-yl}-1H-pyrazol-3-yl)-2-imidazolidinone (compound 1-18);

1-{1-[6-Methyl-1-(6-methyl-1,3-benzodioxol-5-yl)-2,3-dihydro-1H-pyrrolo[2,3-b]pyridin-4-yl]-1H-pyrazol-3-yl}-2-imidazolidinone (compound 1-19);

1-(6-{6-Methyl-1-[2-methyl-4-(methyloxy)phenyl]-2,3-dihydro-1H-pyrrolo[2,3-b]pyridin-4-yl}-2-pyridinyl)-2-imidazolidinone (compound 1-20);

1-(4-{6-Methyl-1-[2-methyl-4-(methyloxy)phenyl]-2,3-dihydro-1H-pyrrolo[2,3-b]pyridin-4-yl}-2-pyrimidinyl)-2-imidazolidinone (compound 1-21);

1-(2-{6-Methyl-1-[2-methyl-4-(methyloxy)phenyl]-2,3-dihydro-1H-pyrrolo[2,3-b]pyridin-4-yl}-4-pyrimidinyl)-2-imidazolidinone (compound 1-22);

1-(1-{6-Methyl-1-[2-methyl-4-(methyloxy)phenyl]-2,3-dihydro-1H-pyrrolo[2,3-b]pyridin-4-yl}-1H-pyrazol-3-yl)-2-imidazolidinone (compound 1-23);

1-(1-{2,6-Dimethyl-1-[2-methyl-4-(methyloxy)phenyl]-2,3-dihydro-1H-pyrrolo[2,3-b]pyridin-4-yl}-1H-pyrazol-3-yl)-2-imidazolidinone (compound 1-24);

1-(3-{6-Methyl-1-[2-methyl-4-(methyloxy)phenyl]-2,3-dihydro-1H-pyrrolo[2,3-b]pyridin-4-yl}phenyl)-2-imidazolidinone (compound 1-25);

1-(5-Methyl-1-{6-methyl-1-[2-methyl-4-(methyloxy)phenyl]-2,3-dihydro-1H-pyrrolo[2,3-b]pyridin-4-yl}-1H-pyrazol-3-yl)-2-imidazolidinone (compound 1-26);

1-[1-(1-{4-[(difluoromethyl)oxy]-2-methylphenyl}-6-methyl-2,3-dihydro-1H-pyrrolo[2,3-b]pyridin-4-yl)-1H-pyrazol-3-yl]-2-imidazolidinone (compound 1-27);

1-{1-[1-(4-Methoxy-2-methylphenyl)-6-methyl-2,3-dihydro-1H-pyrrolo[2,3-b]pyridin-4-yl]-1H-pyrazol-3-yl}pyrrolidin-2-one (compound 2-1);

1-{1-[1-(4-Methoxy-2-methylphenyl)-6-methyl-2,3-dihydro-1H-pyrrolo[2,3-b]pyridin-4-yl]-1H-pyrazol-3-yl}tetrahydropyrimidin-2(1H)-one (compound 3-1);

3-(1-{6-Methyl-1-[2-methyl-4-(methyloxy)phenyl]-2,3-dihydro-1H-pyrrolo[2,3-b]pyridin-4-yl}-1H-pyrazol-3-yl)-1,3-oxazolidin-2-one (compound 4-1);

Methyl 5-(1-{6-methyl-1-[2-methyl-4-(methyloxy)phenyl]-2,3-dihydro-1H-pyrrolo[2,3-b]-pyridin-4-yl}-1H-pyrazol-3-yl)-1,2,5-thiadiazolidine-2-carboxylate 1,1-dioxide) (compound 5-1);

4-[3-(1,1-Dioxido-1,2,5-thiadiazolidin-2-yl]-1H-pyrazol-1-yl-6-methyl-1-[2-methyl-4-(methyloxy)phenyl]-2,3-dihydro-1H-pyrrolo[2,3-b]pyridine (compound 5-2).

4-[3-(1,1-Dioxido-2-isothiazolidinyl)-1H-pyrazol-1-yl]-6-methyl-1-[2-methyl-4-(methyloxy)phenyl]-2,3-dihydro-1H-pyrrolo[2,3-b]pyridine (compound 6-1);

3-Methyl-1-(1-{6-methyl-1-[2-methyl-4-(methyloxy)phenyl]-2,3-dihydro-1H-pyrrolo[2,3-b]pyridin-4-yl}-1H-pyrazol-3-yl)-2(1H)-pyridinone (compound 7-1);

2-(1-{6-Methyl-1-[2-methyl-4-(methyloxy)phenyl]-2,3-dihydro-1H-pyrrolo[2,3-b]pyridin-4-yl}-1H-pyrazol-3-yl)-3(2H)-pyridazinone (compound 8-1);

1-(1-{6-Methyl-1-[2-methyl-4-(methyloxy)phenyl]-2,3-dihydro-1H-pyrrolo[2,3-b]pyridin-4-yl}-1H-pyrazol-3-yl)-1,3-dihydro-2H-imidazol-2-one (compound 9-1);

1-(1-{6-Methyl-1-[2-methyl-4-(methyloxy)phenyl]-1H-pyrrolo[2,3-b]pyridin-4-yl}-1H-pyrazol-3-yl)-2-imidazolidinone (compound 10-1);

1-(6-{6-Methyl-1-[2-methyl-4-(methyloxy)phenyl]-2,3-dihydro-1H-pyrrolo[2,3-b]pyridin-4-yl}-3-pyridinyl)-2-imidazolidinone (compound 11-1);

1-{1-[7-(2,4-Dichlorophenyl)-2-methyl-6,7-dihydro-5H-pyrrolo[2,3-d]pyrimidin-4-yl]-1H-pyrazol-3-yl}-2-pyrrolidinone (compound 11-2).

In general, the compounds of structure (I) may be made according to the organic synthesis techniques known to those skilled in this field, as well as by the representative methods set forth in the Examples.

Compounds of formula (I), and salts and solvates thereof, may be prepared by the general methods outlined hereinafter.

In the following description, the groups R, $R_1$, $R_2$, $R_3$, $R_4$, $R_5$, $R_6$, $R_7$, $R_8$, $R_9$, $R_{10}$, $R_{11}$, $R_{12}$, m, n, q, D, G, Z, W, X, Y have the meanings as previously defined for compounds of formula (I) unless otherwise stated.

Compounds of formula (II) may be conveniently prepared, starting from compounds of formula (VII), according to the following Scheme 1:

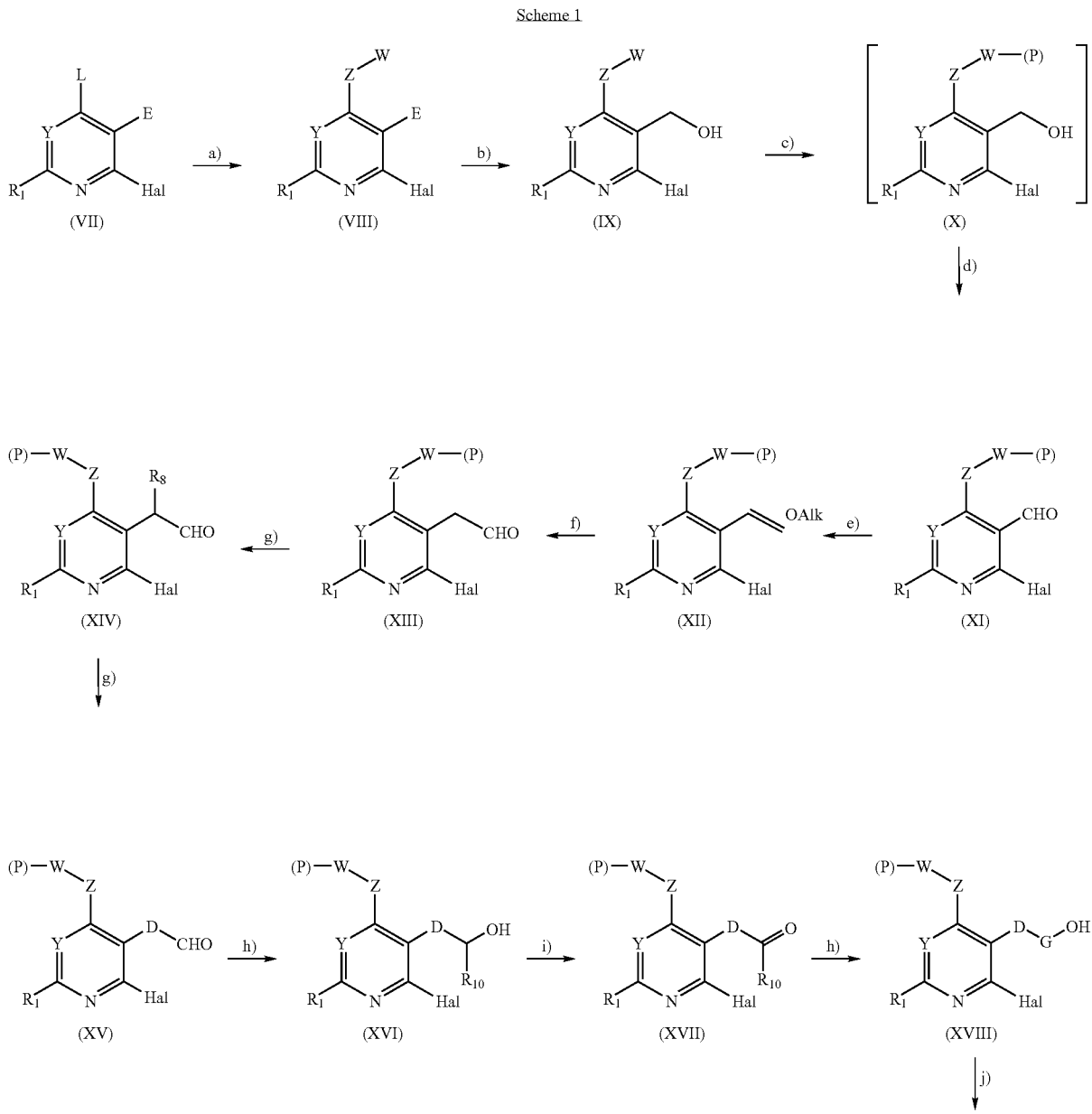

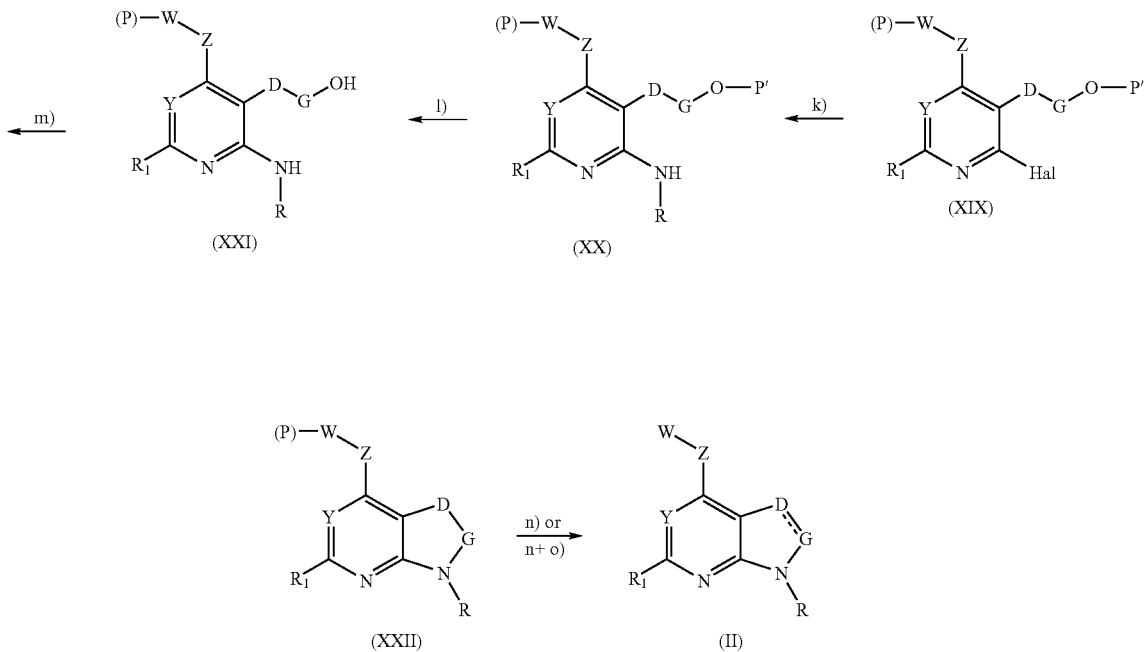

in which step a  stands for conversion of the leaving group L, selected in a group consisting from: halogen or reactive residue of sulphonic acid (e.g. mesylate, tosylate), preferably chloride, in the compounds (VIII), by reaction with the suitable Z-W derivative;

step b  stands for reduction of the ester group (E) with a suitable reducing agent (such as DIBAl-H) to hydroxy group of compounds (IX);

step c  stands for suitable protection of the NH group eventually present in W group with a P group, such as a p-methoxybenzyl group;

step d  stands for oxidation of the hydroxy group with a suitable oxidizing agent (such as Dess-Martin periodinane) to the aldehyde group of compounds (XI);

step e+f  stands for formation of the aldehyde group of compounds (XIII) by Wittig reaction in the usual conditions, through formation of enol ether followed by acid hyrolysis (step f);

step g  stands for the optional alkylation of the α position of the aldehyde by deprotonation with a suitable base (such as LiN(SiMe3)2), followed by the addition of a suitable alkylating agent (such as MeI) to form the alkylated aldehyde of compounds (XIV), (XV);

step h  stands for the conversion of the aldehyde group by a Grignard reagent (such as MeMgBr) into an alcohol group of compounds (XVI) and (XVIII);

step i  stands for oxidation of the hydroxy group with a suitable oxidizing agent such as (Dess-Martin periodinane) to the ketone group of compounds (XVII);

step j  stands for conversion of the hydroxy group in the suitable protecting group of compounds (XIX) (such as TBS: tertbutyldimethylsilyl);

step k  stands for a Buchwald coupling reaction witht he suitable amine RNH2 to give the compounds of formula (XX);

step l  stands for the deprotection reaction to give th hydroxy group of compounds (XXI);

step m  stands for intramolecular cyclisation after conversion of the hydroxy group of compounds (XXI) in a suitable leaving group (such as bromide, by reaction with CBr4 and PPh3) to give the cyclized compounds (XXI);

step n  stands for the deprotection reaction of the protected NH group eventually present in W group, to give final compounds (II);

step o  stands for oxidation by a suitable oxidating agent (such as DDQ) in order to give formation of the double bond of compounds (II), when D is CHR8 and G is CHR10.

Compounds of formula (VII) are known compounds or may be prepared according to known method in the literature.

Alternatively, compounds of formula (IIr) may be conveniently prepared, starting from compounds of formula (XXIII), in which R, $R_1$ Z and W are defined as above, according to the following Scheme 2:

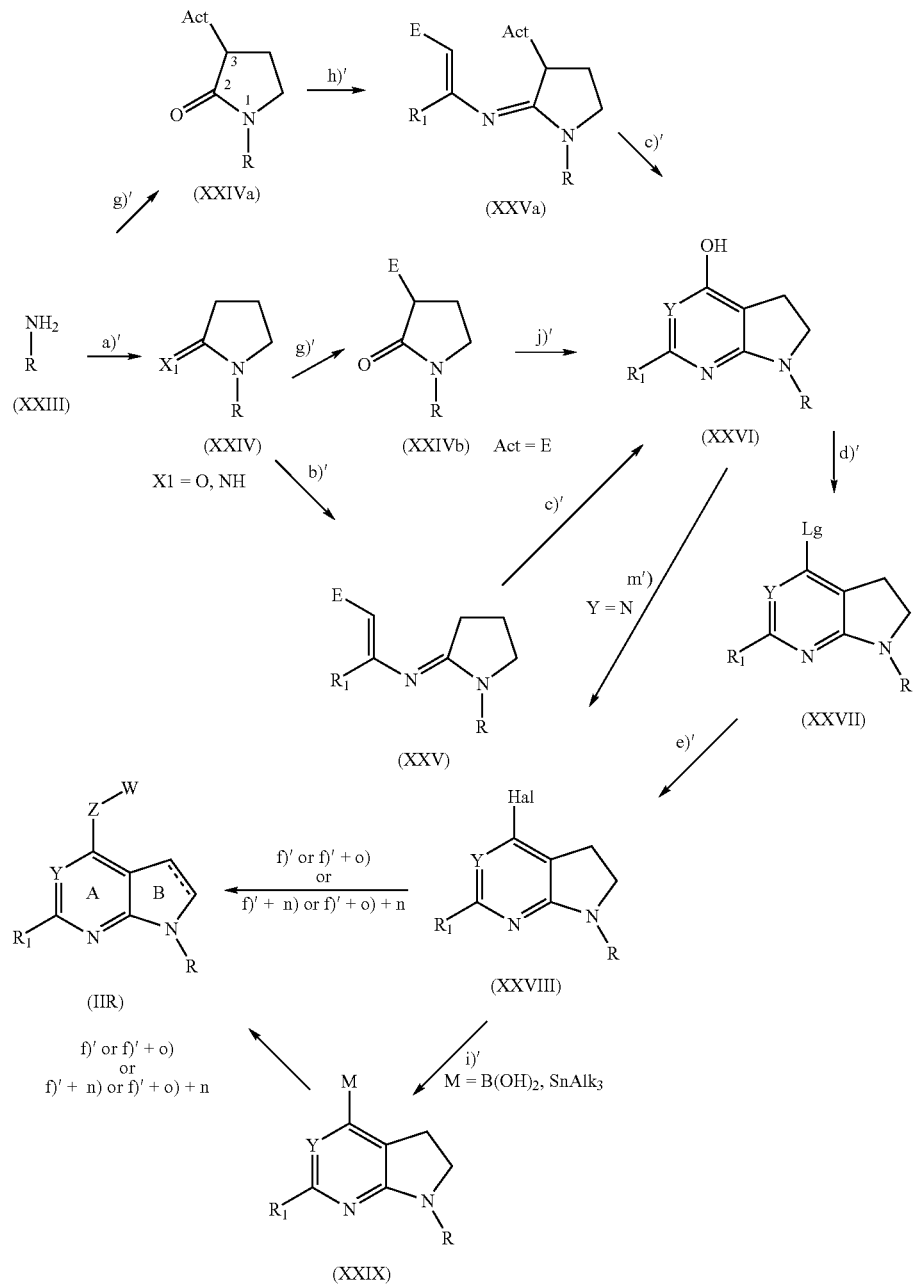
Scheme 2

-continued in which:
- step a'  stands for the formation of the pyrrolidinone moiety of compounds (XXIV), which will form the cycle B present in the final compounds (IIr), by reacting the compounds (XXIII) with a reactive derivative of the butyric acid, such as 4-chlorobutyryl chloride; followed by a cyclisation reaction in basic conditions (e.g. KotBu);
- step b'  stands for the amidine formation by reacting the compounds (XXIV) with a 3-aminocrotonate derivative and POCl₃ when $X_1$ is oxygen; or stands for alkylation of the amidine formation by reacting the compound (XXIV) with a butynoate derivative, when $X_1$ is NH;
- step c'  stands for the cyclisation of the compounds (XXV) or (XXVa) in basic conditions (e.g. tBuOK) to give the hydroxy pyridine precursor of cycle A in the final compounds (IIR);
- step d'  stands for the formation of a reactive derivative (i.e. a leaving group, Lg) of the hydroxy pyridine (for example selected in a group consisting of triflate, halogen, and mesylate) of compounds (XXVI) by reaction with, for example, triflic anhydride;
- step e'  stands for nucleophilic displacement of the leaving group of compounds (XXVII) to give the halogenated compounds (XXVIII), preferably iodinated or brominated compounds;
- step f'  stands for the arylation reaction with the suitable —Z—W derivative by a metal catalysed coupling reaction (for example a Buchwald reaction or a Suzuki coupling) procedure to give the final compounds (IIr); such —Z—W derivative may be suitably protected with a P group, as defined in Scheme 1,
- step g'  stands for activation of carbon 3 by the addition of an electron-withdrawing group (e.g. acylation to give an ester group such as acylation with diethyl carbonate to give the ethyl ester derivativ, E);
- step h'  corresponds to step b)' when X1 is oxygen.
- step i'  stands for a metal-halogen exchange reaction (with a suitable base, such as n-BuLi) followed by a trans-metalation reaction with a suitable metalating agent (such as a trialkylborate or a trialkylstannyl chloride);
- step j'  stands for the cyclisation of the β-amidoester of formula (XXIVb) with a salt (e.g. hydrochloride) of a substituted amidine (such as acetamidine hydrochloride) in order to form the pyrimidine cycle A, when Y is N;
- step m'  stands for conversion of the hydroxy group into an halogen by the halogenation reaction carried out using, for example, treatment with PO(Hal)₃, wherein Hal is preferably chlorine.

In general, the starting compounds of formula (XXIII) are known compounds or may be prepared according to known methods in the literature.

The process of Scheme 2 is particularly convenient for the preparation of compounds of general formula (IV), (V), (VI).

The compounds of general formula (XXIV), (XXIVb), (XXVI), (XXVII), (XXVIII), (XXIX) are novel intermediates useful for the preparation of the CRF antagonists object of the present invention or other CRF antagonists, which may be conveniently prepared using such intermediates. Representative CRF antagonists which may be prepared using the above intermediates include, but are not limited to, those disclosed in the above cited Patent Applications: WO 95/10506, WO 95/33750, WO 02/08895 and WO 03/008412.

The above cited publications, including but not limited to patents and patent applications, are herein incorporated by reference as if each individual publication were specifically and individually indicated to be incorporated by reference herein as though fully set forth.

In particular, the compounds of formula (XXVIA), corresponding to the compounds of formula (XXVI) when Y corresponds to a carbon atom, may exist in the tautomeric form (XXVIB).

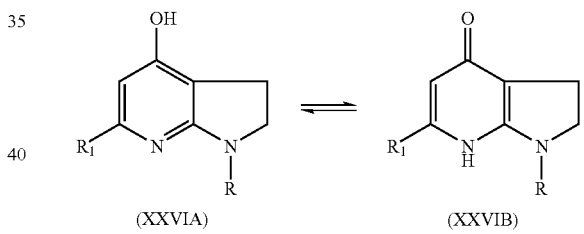

(XXVIA)  (XXVIB)

The compounds of general formula (IIt) may be prepared in an alternative way according to the method described in the International Patent Application WO 02/088095, as illustrated in the following Scheme 3.

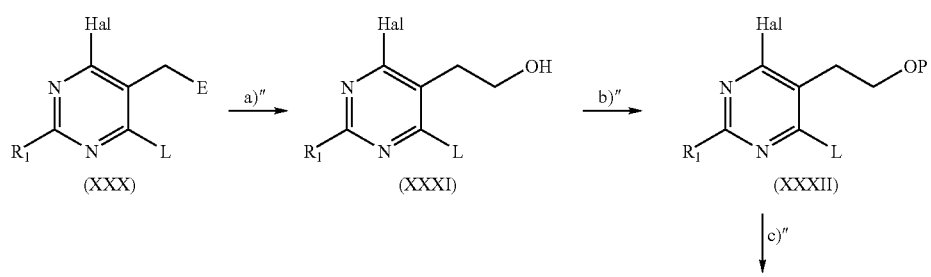

(XXX)  (XXXI)  (XXXII)

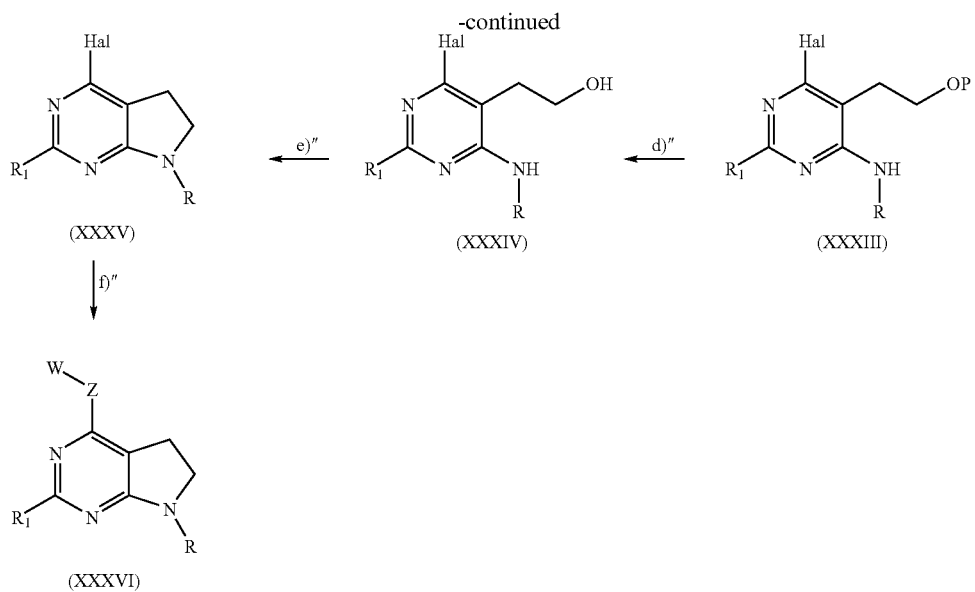

in which
- step a″ stands for reduction of the ester with a suitable reducing agent (such as DIBAl-H) to give compounds (XXXI);
- step b″ stands for conversion of the hydroxy group in the suitable protecting group of compounds (XXII)(such as TBS: tert-butyldimethylsilyl);
- step c″ stands for a nucleophilic displacement reaction with the suitable amine $RNH_2$ to give the compounds of formula (XXXIII);
- step d″ stands for the deprotection reaction to give the hydroxy group of compounds (XXXIV);
- step e″ stands for intramolecular cyclisation after conversion of the hydroxy group of compounds (XXXIV) in a suitable leaving group (such as mesylate, by reaction with $Et_3N$ and ($CH_3SO_2Cl$) to give the cyclized compounds (XXXV);
- step f″ stands for a metal mediated coupling reaction with a suitable Z-W derivative to give compounds The starting material is already known in literature, as acid derivative (see Snider, Barry B.; Ahn, Yong; Foxman, Bruce M. Synthesis of the tricyclic triamine core of martinelline and martinellic acid. *Tetrahedron Letters* (1999), 40(17), 3339-3342).

When the -Z-W moiety of compounds of formula (I) is not a known compound already described in the literature, it may be prepared in analogy to the following Schemes.

The Schemes represent the preparation of specific derivatives of -Z-W moieties, sometimes without the presence of further substituents as defined above, in order to simplify the understanding of the chemical processes.

This does not limit at all the availability of such processes for the preparations of derivatives containing more substituents or linked to different moieties.

Examples of the following preparations can be found in the Experimental section.

Scheme for the synthesis of a derivative suitable for the preparation of the compounds of formula (II) in which Z corresponds to a pyrazolyl derivative and W is a W2 derivative, for example 1-(1H-pyrazol-3-yl)imidazolidin-2-one (intermediate 8):

Scheme 4

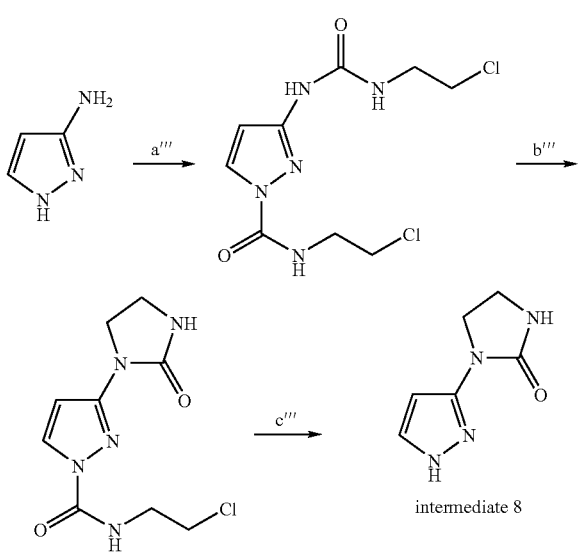

in which
- step a‴ stands for the reaction of 3-aminopyrazole with chloroethyl isocyanate in DMF at 0° C;
- step b‴ stands for cyclisation reaction with KOt-Bu in THF at r.t;
- step c‴ stands for deprotection reaction by LiOH in MeOH/$H_2O$ AT 80° C.

Scheme for the synthesis of a derivative suitable for the preparation of the compounds of formula (II) in which Z corresponds to a pyrazolyl derivative and W is a W9 derivative, for example of 1-(1H-pyrazol-3-yl)pyrrolidin-2-one (intermediate 10):

Scheme 5

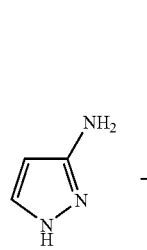

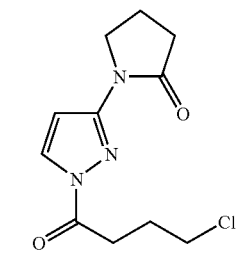

intermediate 10 in which
step a^iv stands for reaction of 3-aminopyrazole with 4-chloro butyryl chloride in presence of K₂HPO₄, and in CH₂Cl₂;
step b^iv stands for cyclisation reaction with NaH, in DMF, at r.t.;
step c^iv stands for deprotection reaction by MeONa/MeOH, at r.t..

Scheme for the synthesis of a derivative suitable for the preparation of the compounds of formula (II), in which Z corresponds to a pyrazolyl derivative and W is a W3 derivative, for example of 1-(1H-pyrazol-3-yl)tetrahydropyrimidin-2(1H)-one (intermediate 13)

Scheme 6

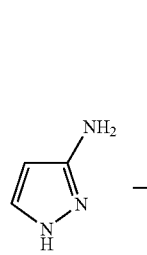

-continued

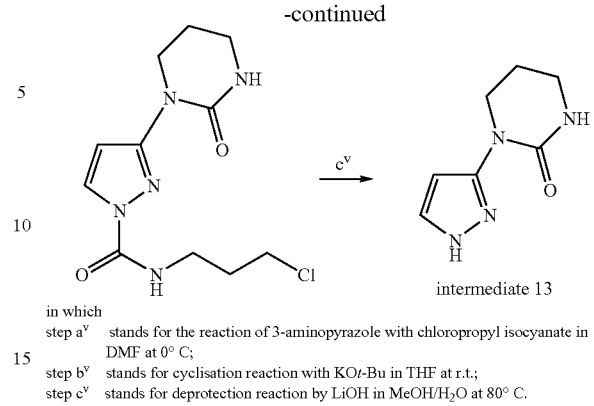

intermediate 13 in which
step a^v stands for the reaction of 3-aminopyrazole with chloropropyl isocyanate in DMF at 0° C;
step b^v stands for cyclisation reaction with KOt-Bu in THF at r.t.;
step c^v stands for deprotection reaction by LiOH in MeOH/H₂O at 80° C.

Scheme for the synthesis of a derivative suitable for the preparation of the compounds of formula (II), in which Z corresponds to a pyridyl derivative and W is a W2 derivative, for example, protected 1-(6-bromo-2-pyridinyl)-2-imidazolidinone (intermediate 96).

Scheme 7

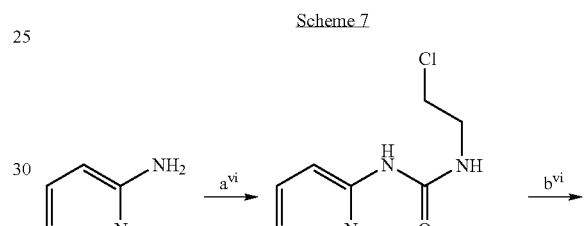

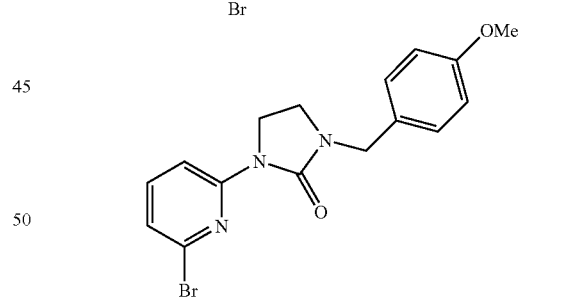

intermediate 96 in which
step a^vi stands for the condensation of 1-chloro-2-isocyanatoethane with 6 bromo-2-pyridinamine to give the urea;
step b^vi stands for the cyclisation reaction in basic conditions (t-BuOK in THF);
step c^vi stands for protection of the urea NH group with a suitable protecting group (such as a para-methoxybenzyl group.)

Scheme for the synthesis of derivatives suitable for the preparation of the compounds of formula (II), in which Z corresponds to a pyrimidinyl derivative and W is a W2 derivative, for example, protected 1-(4-bromo-2-pyrimidinyl)-2-imidazolidinone (intermediate 102) and protected 1-(2-bromo-4-pyrimidinyl)-2-imidazolidinone (intermediate 104).

Scheme 8

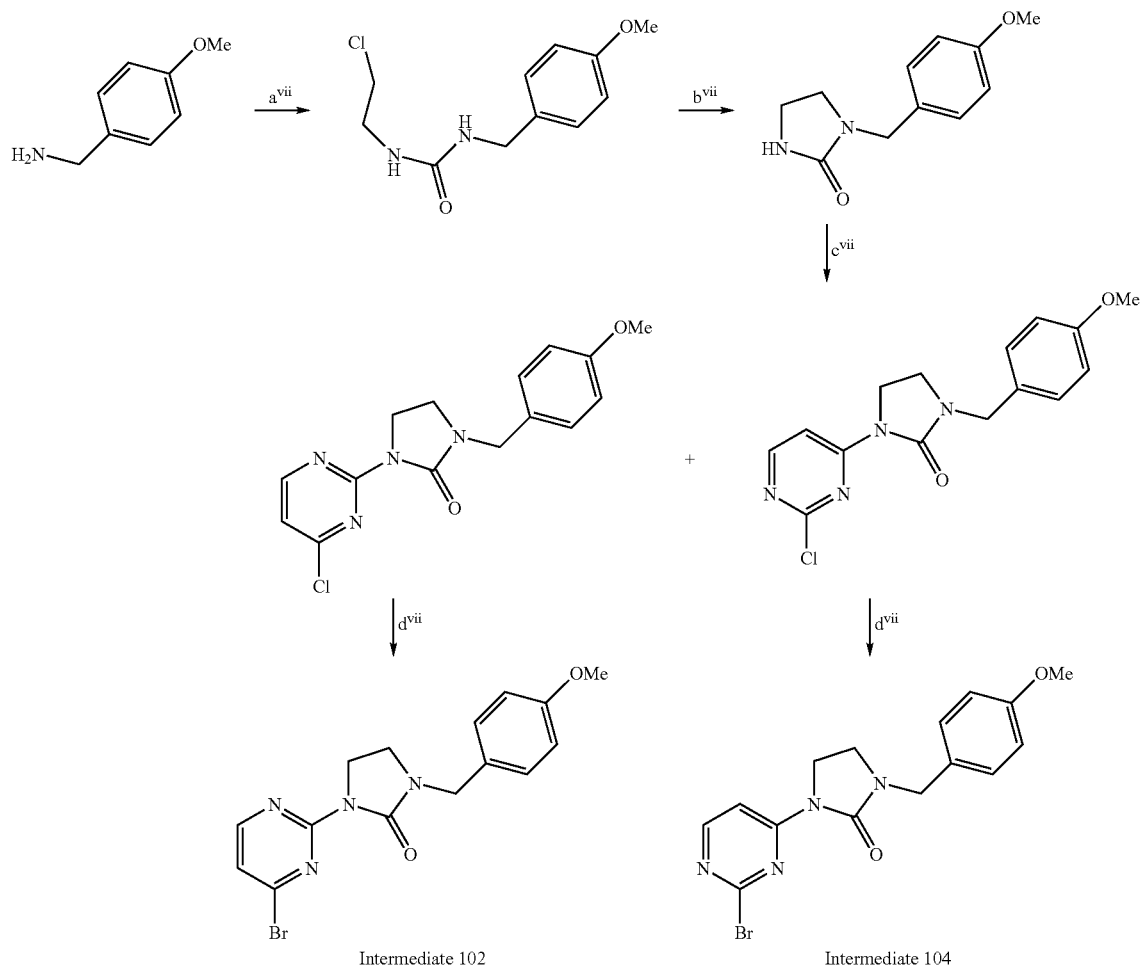

in which
step a^vii stands for the condensation of 1-chloro-2-isocyanatoethane with 4-methoxybenyl amine to give the urea derivative;
step b^vii stands for the cyclisation reaction in basic conditions (t-BuOK in THF);
step c^vii stands for the nucleophilic substitution of the cyclic urea on 2,4-dichloropyrimidine in basic conditions (such as NaH in DMF);
step d^vii stands for exchange of the chloride group into a bromide group by reaction with TMSBr (trimethylsilyl bromide).

Scheme for the synthesis of the compounds of formula (II), in which Z is a triazolyl or pyrazolyl derivative. In particular the synthesis of the compounds (IIr) in which Z is triazolyl or pyrazolyl derivative and W is a W2 derivative, 1-(1H-1,2,4-triazol-3-yl)-2-imidazolidinone substituent ($R_5$=H, X=N) and 1-(5-methyl-1H-pyrazol-3-yl)-2-imidazolidinone substituent ($R_5$=Me, X=C)

Scheme 9

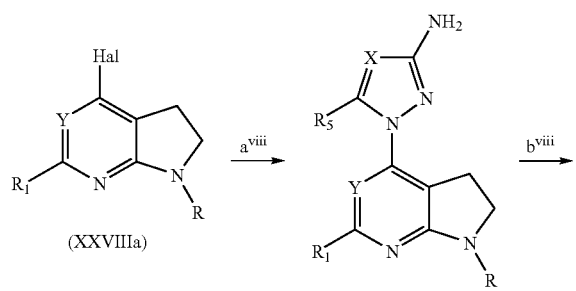

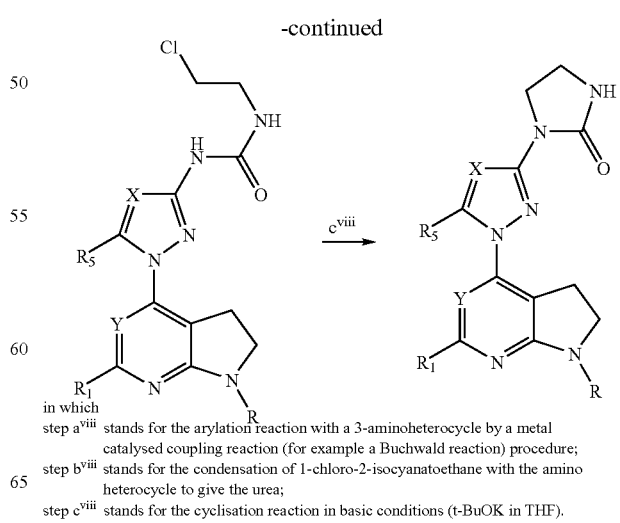

in which
step a^viii stands for the arylation reaction with a 3-aminoheterocycle by a metal catalysed coupling reaction (for example a Buchwald reaction) procedure;
step b^viii stands for the condensation of 1-chloro-2-isocyanatoethane with the amino heterocycle to give the urea;
step c^viii stands for the cyclisation reaction in basic conditions (t-BuOK in THF).

Scheme for the synthesis of a derivative suitable for the preparation of the compounds of formula (II), in which Z corresponds to a phenyl derivative and W is a W2 derivative, for example, 1-phenyl-2-imidazolidinone substituent.

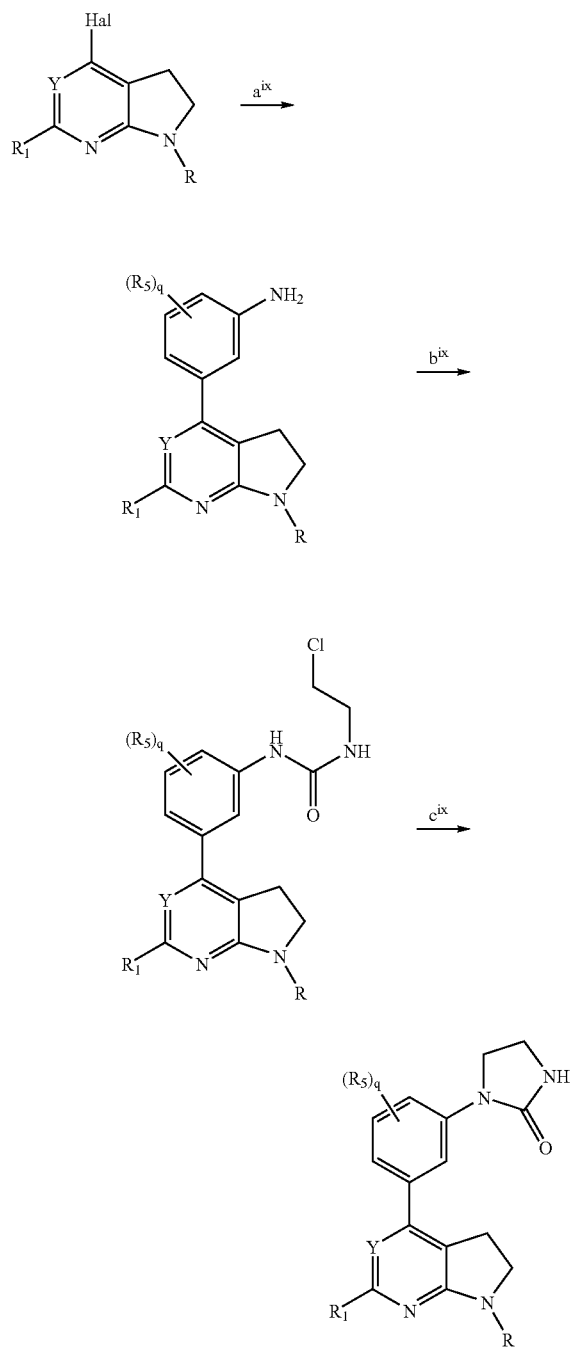

in which
step a$^{ix}$ stands for step f)' as defined in Scheme 2 (Suzuki coupling with the boronic acid derivative);
step b$^{ix}$ stands for the condensation of 1-chloro-2-isocyanatoethane with 6-bromo-2-pyridinamine to give the urea;
step c$^{ix}$ stands for the cyclisation reaction in basic conditions (t-BuOK in THF).

Scheme for the synthesis of a derivative suitable for the preparation of the compounds of formula (II), in which Z corresponds to a pyrazolyl derivative and W is a W11, W13, or a W14 derivative, for example, 3-(1H-pyrazol-3-yl)-1,3-oxazolidin-2-one (intermediate 16), 3-methyl-1-(1H-pyrazol-3-yl)-2(1H)-pyridinone (intermediate 26) and 2-(1H-pyrazol-3-yl)-3(2H)-pyridazinone (intermediate 28).

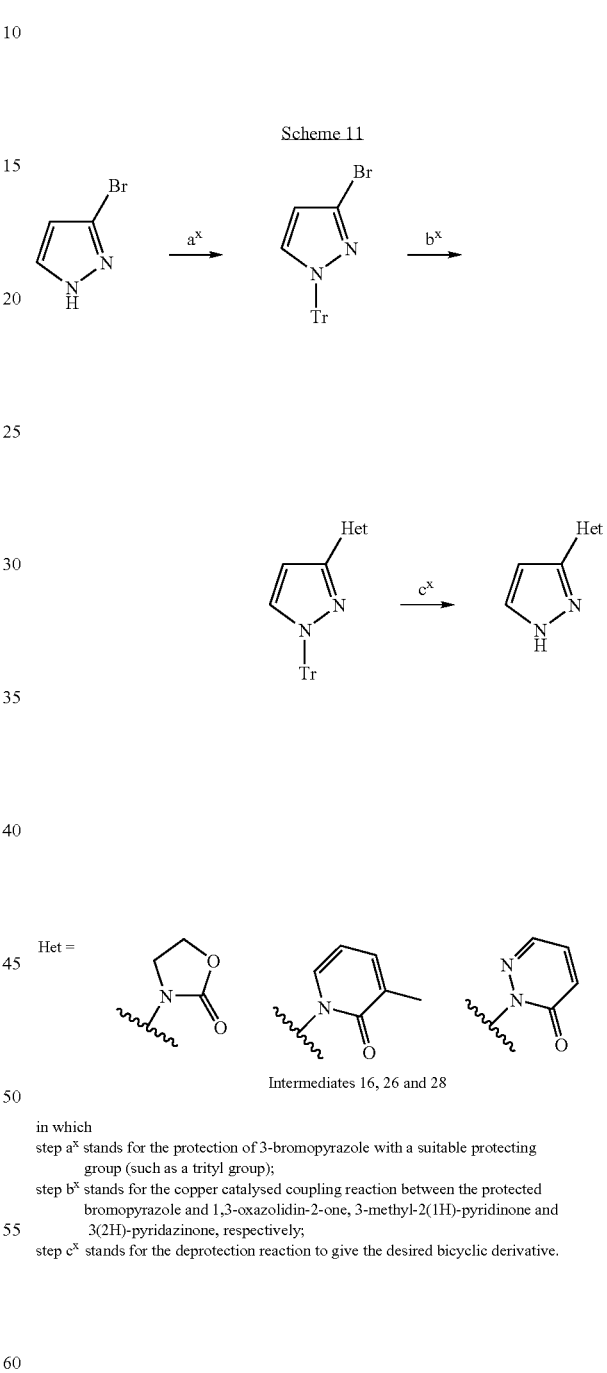

Intermediates 16, 26 and 28 in which
step a$^x$ stands for the protection of 3-bromopyrazole with a suitable protecting group (such as a trityl group);
step b$^x$ stands for the copper catalysed coupling reaction between the protected bromopyrazole and 1,3-oxazolidin-2-one, 3-methyl-2(1H)-pyridinone and 3(2H)-pyridazinone, respectively;
step c$^x$ stands for the deprotection reaction to give the desired bicyclic derivative.

Scheme for the synthesis of a derivative suitable for the preparation of the compounds of formula (IIr), in which Z corresponds to a pyrazolyl derivative and W is a W10 derivative, for example, 2-(1H-pyrazol-3-yl)-1,2,5-thiadiazolidine 1,1-dioxide substituent.

Scheme 12

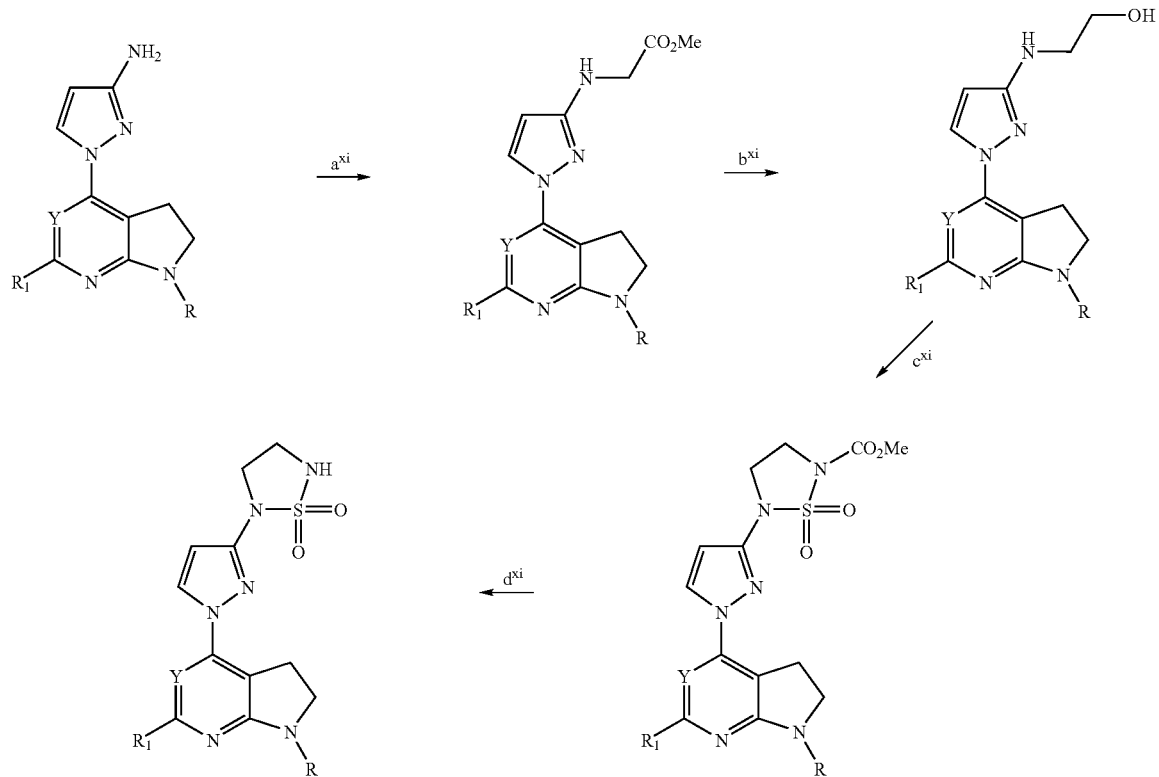

in which
step $a^{xi}$ stands for alkylation of the amino group using ethyl 2-bromoacetate as an alkylating agent;
step $b^{xi}$ stands for reduction of the ester group into the alcohol, using a suitable reducing agent (such as LiAlH$_4$);
step $c^{xi}$ stands for cyclisation of the amino alcohol using Burgess' reagent ((methoxycarbonylsulfamoyl)triethylammonium hydroxide inner salt) to give the cyclic sulfonylurea;
step $d^{xi}$ stands for the deprotection of the sulfonylurea using basic conditions (such as NaOH in a CH$_2$Cl$_2$/MeOH mixture).

Scheme for the synthesis of a derivative suitable for the preparation of the compounds of formula (II), in which Z corresponds to a pyrazolyl derivative and W is a W12 derivative, for example, 2-(1H-pyrazol-3-yl)isothiazolidine 1,1-dioxide substituent.

Scheme 13

-continued

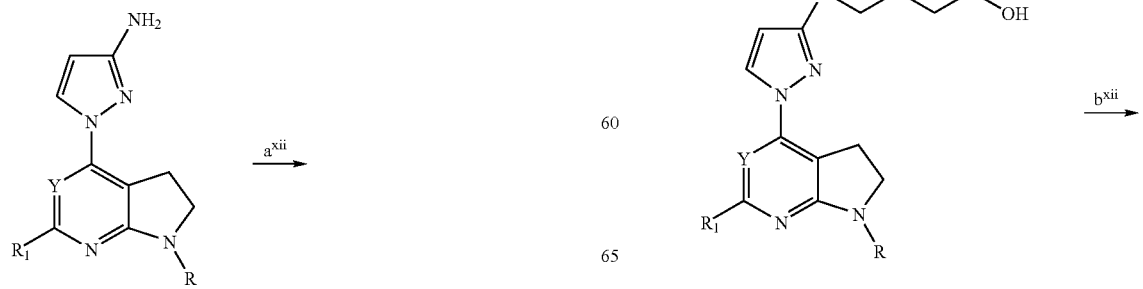

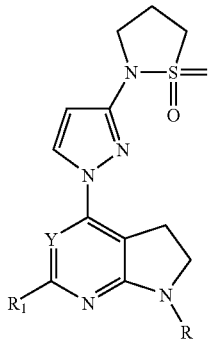

in which
step a$^{xii}$ stands for alkylation of the amino group using 1,2-oxathiolane 2,2-dioxide as an alkylating agent;
step b$^{xii}$ stands for the cyclisation step mediated by the addition of POCl$_3$.

Scheme for the synthesis of a derivative suitable for the preparation of the compounds of formula (IIr), in which Z corresponds to a pyrazolyl derivative and W is a W1 derivative, for example, 1-(1H-pyrazol-3-yl)-1,3-dihydro-2H-imidazol-2-one substituent.

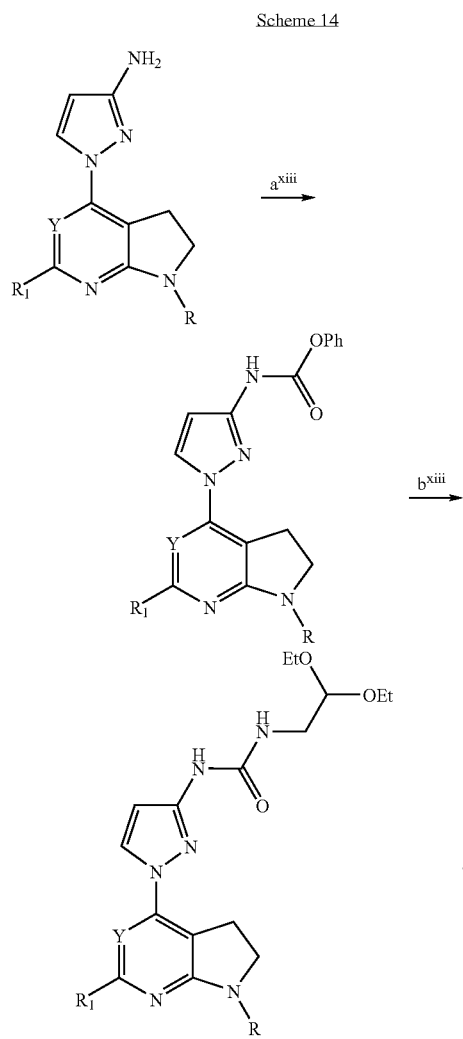

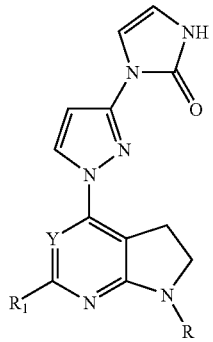

in which
step a$^{xiii}$ stands for the preparation of the phenyl carbamate using phenyl chloroformate;
step b$^{xiii}$ stands for the addition of aminoacetaldehyde dimethyl acetal to the activated carbamate group;
step c$^{xiii}$ stands for the cyclisation reaction in the presence of an acid (such as HCl) to give the 2H-imidazol-2-one substituent.

The R group present in compounds of formula (I) is generally a known compound.

When such R group is not a compound already described in the literature, it may be prepared in analogy to the following Schemes.

The Schemes represent the preparation of specific derivatives of R groups, sometimes without the presence of further substituents J as defined above, in order to simplify the understanding of the chemical processes.

This does not limit at all the availability of such processes for the preparations of R groups containing more J substituents.

Examples of the following preparations can be found in the Experimental section.

Scheme for the synthesis of 2-(difluoromethyl)-4-(methyloxy)aniline.

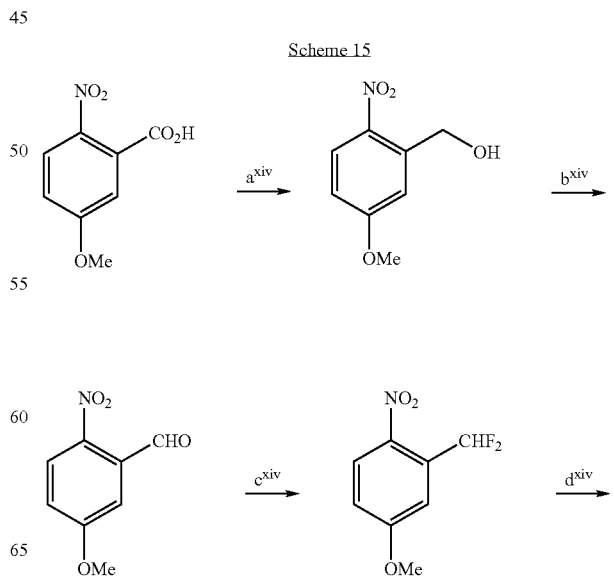

-continued

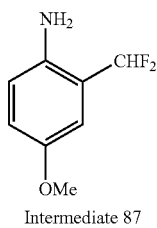
Intermediate 87 in which
step a$^{xiv}$ stands for reduction of the acid group with a suitable reducing agent (such as cyanuric chloride/NMM/NaBH$_4$);
step b$^{xiv}$ stands for oxydation of the alcohol to the aldehyde with a suitable oxidizing agent (such as Dess-Martin periodinane);
step c$^{xiv}$ stands for difluorination of the aldehyde using a suitalbe fluorinating agent (such as DAST: (diethylamino)sulfur trifluoride);
step d$^{xiv}$ stands for the reduction of the nitro group with a suitable reducing agent (such as H$_2$, catalysed with palladium on activated charcoal).

Scheme for the preparation of 2-(Methyloxy)-4-(1H-pyrazol-1-yl)aniline (intermediate 88).

Scheme 16

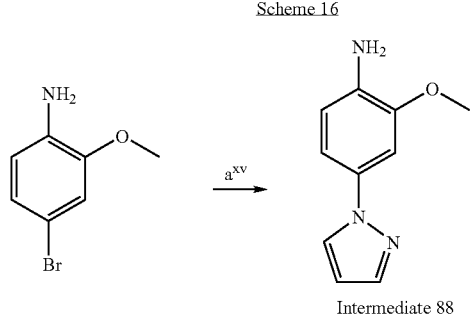
Intermediate 88

In which
step a$^{xv}$ stands for the copper catalysed coupling reaction between 4-bromo-2-(methyloxy)aniline and pyrazole.

Compounds of formula (IIn) may be conveniently prepared according to the following Scheme 4 and where the starting material was prepared according to WO 02/088095 A1

Scheme 17

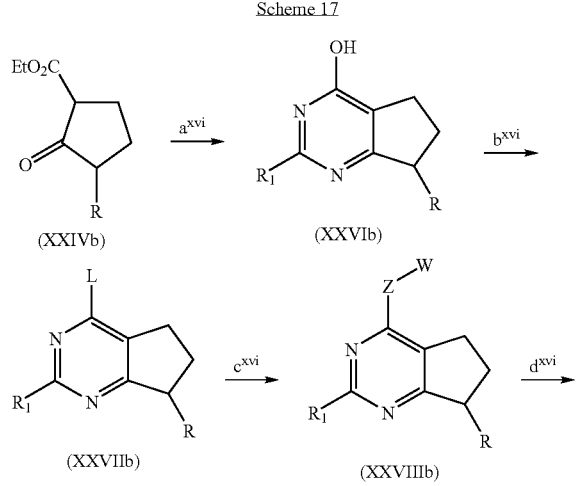

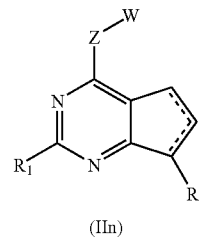
(IIn)

in which
step a$^{xvi}$ stands for the cyclisation of the β-ketoester of formula (XXIVb) with a salt (e.g. hydrochloride) of a substituted amidine (such as acetamidine hydrochloride);
step b$^{xvi}$ stands for the transformation of the hydroxy group of formula (XXVIb) into a suitable leaving group, selected in a group consisting from halogen or reactive residue of sulphonic acid (e.g. mesylate, tosylate), preferably chloride;
step c$^{xvi}$ stands for conversion of the leaving group L in the compounds (XXVIIIb), by reaction with the suitable ——Z—W derivative;
step d$^{xvi}$ corresponds to previous step o in Scheme 1.

In particular, when J is a group OCHF$_2$, this can be introduced directly in the R group by methods already known in the literature or, eventually, the group OCH$_3$ may be deprotected using one of the methods listed in the Greene's reference cited below. Then, the hydroxyl group may be alkylated by using a suitable fluoroalkylating agent, such as CF$_2$Br$_2$, as exemplified for Intermediate 125.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

Pharmaceutical acceptable salts may also be prepared from other salts, including other pharmaceutically acceptable salts, of the compound of formula (I) using conventional methods.

The compounds of formula (I) may readily be isolated in association with solvent molecules by crystallisation or evaporation of an appropriate solvent to give the corresponding solvates.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{36}$Cl, $^{123}$I and $^{125}$I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3$H, $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C and $^{18}$F isotopes are particularly useful in PET (positron emission tomography), and $^{125}$I isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

The CRF receptor antagonists of the present invention demonstrate activity at the CRF receptor site and may be used in the treatment of conditions mediated by CRF or CRF receptors.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (J. Neuroscience 7: 88, 1987) and Battaglia et al. (Synapse 1: 572, 1987).

The CRF receptors-binding assay was performed by using the homogeneous technique of scintillation proximity (SPA). The ligand binds to recombinant membrane preparation expressing the CRF receptors which in turn bind to wheatgerm agglutinin coated SPA beads. In the Experimental Part will be disclosed the details of the experiments.

With reference to CRF receptor binding affinities, CRF receptor antagonists of this invention have a Ki less than 10 µm.

Compounds of the invention are useful in the treatment of central nervous system disorders where CRF receptors are involved. In particular in the treatment or prevention of major depressive disorders including bipolar depression, unipolar depression, single or recurrent major depressive episodes with or without psychotic features, catatonic features, melancholic features, atypical features or postpartum onset, the treatment of anxiety and the treatment of panic disorders. Other mood disorders encompassed within the term major depressive disorders include dysthymic disorder with early or late onset and with or without atypical features, neurotic depression, post traumatic stress disorders, post operative stress and social phobia; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood. Major depressive disorders may also result from a general medical condition including, but not limited to, myocardial infarction, diabetes, miscarriage or abortion, etc.

Compounds of the invention are also useful in the treatment or prevention of schizophrenic disorders including paranoid schizophrenia, disorganised schizophrenia, catatonic schizophrenia, undifferentiated schizophrenia, residual schizophrenia.

Compounds of the invention are useful as analgesics. In particular they are useful in the treatment of traumatic pain such as postoperative pain; traumatic avulsion pain such as brachial plexus; chronic pain such as arthritic pain such as occurring in osteo-, rheumatoid or psoriatic arthritis; neuropathic pain such as post-herpetic neuralgia, trigeminal neuralgia, segmental or intercostal neuralgia, fibromyalgia, causalgia, peripheral neuropathy, diabetic neuropathy, chemotherapy-induced neuropathy, AIDS related neuropathy, occipital neuralgia, geniculate neuralgia, glossopharyngeal neuralgia, reflex sympathetic dystrophy, phantom limb pain; various forms of headache such as migraine, acute or chronic tension headache, temporomandibular pain, maxillary sinus pain, cluster headache; odontalgia; cancer pain; pain of visceral origin; gastrointestinal pain; nerve entrapment pain; sport's injury pain; dysmennorrhoea; menstrual pain; meningitis; arachnoiditis; musculoskeletal pain; low back pain e.g. spinal stenosis; prolapsed disc; sciatica; angina; ankylosing spondyolitis; gout; burns; scar pain; itch; and thalamic pain such as post stroke thalamic pain.

Compounds of the invention are also useful for the treatment of dysfunction of appetite and food intake and in circumstances such as anorexia, anorexia nervosa and bulimia.

Compounds of the invention are also useful in the treatment of sleep disorders including dysomnia, insomnia, sleep apnea, narcolepsy, and circadian rhythmic disorders.

Compounds of the invention are also useful in the treatment or prevention of cognitive disorders. Cognitive disorders include dementia, amnestic disorders and cognitive disorders not otherwise specified.

Furthermore compounds of the invention are also useful as memory and/or cognition enhancers in healthy humans with no cognitive and/or memory deficit.

Compounds of the invention are also useful in the treatment of tolerance to and dependence on a number of substances. For example, they are useful in the treatment of dependence on nicotine, alcohol, caffeine, phencyclidine (phencyclidine like compounds), or in the treatment of tolerance to and dependence on opiates (e.g. cannabis, heroin, morphine) or benzodiazepines; in the treatment of cocaine, sedative ipnotic, amphetamine or amphetamine-related drugs (e.g. dextroamphetamine, methylamphetamine) addiction or a combination thereof.

Compounds of the invention are also useful as anti-inflammatory agents. In particular they are useful in the treatment of inflammation in asthma, influenza, chronic bronchitis and rheumatoid arthritis; in the treatment of inflammatory diseases of the gastrointestinal tract such as Crohn's disease, ulcerative colitis, postoperative gastric ileus (POI), inflammatory bowel disease (IBD) and non-steroidal anti-inflammatory drug induced damage; inflammatory diseases of the skin such as herpes and eczema; inflammatory diseases of the bladder such as cystitis and urge incontinence; and eye and dental inflammation.

Compounds of the invention are also useful in the treatment of allergic disorders, in particular allergic disorders of the skin such as urticaria, and allergic disorders of the airways such as rhinitis.

Compounds of the invention are also useful in the treatment of emesis, i.e. nausea, retching and vomiting. Emesis includes acute emesis, delayed emesis and anticipatory emesis. The compounds of the invention are useful in the treatment of emesis however induced. For example, emesis may be induced by drugs such as cancer chemotherapeutic agents such as alkylating agents, e.g. cyclophosphamide, carmustine, lomustine and chlorambucil; cytotoxic antibiotics, e.g. dactinomycin, doxorubicin, mitomycin-C and bleomycin; anti-metabolites, e.g. cytarabine, methotrexate and 5-fluorouracil; vinca alkaloids, e.g. etoposide, vinblastine and vincristine; and others such as cisplatin, dacarbazine, procarbazine and hydroxyurea; and combinations thereof; radiation sickness; radiation therapy, e.g. irradiation of the thorax or abdomen, such as in the treatment of cancer; poisons; toxins such as toxins caused by metabolic disorders or by infection, e.g. gastritis, or released during bacterial or viral gastrointestinal infection; pregnancy; vestibular disorders, such as motion sickness, vertigo, dizziness and Meniere's disease; post-operative sickness; gastrointestinal obstruction; reduced gastrointestinal motility; visceral pain, e.g. myocardial infarction or peritonitis; migraine; increased intracranial pressure; decreased intercranial pressure (e.g. altitude sickness); opioid analgesics, such as morphine; and gastro-oesophageal reflux disease, acid indigestion, over-indulgence of food or drink, acid stomach, sour stomach, waterbrash/regurgitation, heartburn, such as episodic heartburn, nocturnal heartburn, and meal-induced heartburn and dyspepsia.

Compounds of the invention are of particular use in the treatment of gastrointestinal disorders such as irritable bowel syndrome (IBS); skin disorders such as psoriasis, pruritis and sunburn; vasospastic diseases such as angina, vascular headache and Reynaud's disease; cerebral ischeamia such as cerebral vasospasm following subarachnoid haemorrhage; fibrosing and collagen diseases such as scleroderma and eosinophilic fascioliasis; disorders related to immune enhancement or suppression such as systemic lupus erythematosus and rheumatic diseases such as fibrositis; and cough.

Compounds of the invention are useful for the treatment of neurotoxic injury which follows cerebral stroke, thromboembolic stroke, hemorrhagic stroke, cerebral ischemia, cerebral vasospam, hypoglycemia, hypoxia, anoxia, perinatal asphyxia cardiac arrest.

The invention therefore provides a compound of formula (I) or a pharmaceutically acceptable salt or solvate thereof for use in therapy, in particular in human medicine.

There is also provided as a further aspect of the invention the use of a compound of formula (I) or a pharmaceutically acceptable salt or solvate thereof in the preparation of a medicament for use in the treatment of conditions mediated by CRF.

In an alternative or further aspect there is provided a method for the treatment of a mammal, including man, in particular in the treatment of condition mediated by CRF, comprising administration of an effective amount of a compound of formula (I) or a pharmaceutically acceptable salt or a solvate thereof.

While it is possible that, for use in therapy, a compound of the present invention may be administered as the raw chemical, it is preferable to present the active ingredient as a pharmaceutical formulation e.g. when the agent is in admixture with a suitable pharmaceutical excipient, diluent or carrier selected with regard to the intended route of administration and standard pharmaceutical practice.

In a further aspect, the invention provides a pharmaceutical composition comprising at least one compound of the invention or a pharmaceutically acceptable derivative thereof in association with a pharmaceutically acceptable carrier and/or excipient. The carrier and/or excipient must be "acceptable" in the sense of being compatible with the other ingredients of the formulation and not deletrious to the recipient thereof.

Accordingly, the present invention further provides a pharmaceutical formulation comprising at least one compound of the invention or a pharmaceutically acceptable derivative thereof, in association with a pharmaceutically acceptable carrier and/or excipient. The carrier and/or excipient must be "acceptable" in the sense of being compatible with the other ingredients of the formulation and not deletrious to the receipient thereof.

There is further provided by the present invention a process of preparing a pharmaceutical composition, which process comprises mixing at least one compound of the invention or a pharmaceutically acceptable derivative thereof, together with a pharmaceutically acceptable carrier and/or excipient.

The pharmaceutical compositions may be for human or animal usage in human and veterinary medicine and will typically comprise any one or more of a pharmaceutically acceptable diluent, carrier or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as or in addition to the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some embodiments, the agents of the present invention may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta and gamma-cyclodextrins are most commonly used and suitable examples are described in WO-A-91/11172, WO-A-94/02518 and WO-A-98/55148.

In a preferred embodiment, the agents of the present invention are delivered systemically (such as orally, buccally, sublingually), more preferably orally.

Hence, preferably the agent is in a form that is suitable for oral delivery.

It is to be understood that not all of the compounds need be administered by the same route. Likewise, if the composition comprises more than one active component, then those components may be administered by different routes.

The compounds of the invention may be milled using known milling procedures such as wet milling to obtain a particle size appropriate for tablet formation and for other formulation types. Finely divided (nanoparticulate) preparations of the compounds of the invention may be prepared by processes known in the art, for example see International Patent Application No. WO 02/00196 (SmithKline Beecham).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may be formulated for topical administration in the form of ointments, creams, gels, lotions, pessaries, aerosols or drops (e.g. eye, ear or nose drops). Ointments and creams may, for example, be formulated with an aqueous or oily base with the addition of suitable thickening and/or gelling agents. Ointments for administration to the eye may be manufactured in a sterile manner using sterilised components.

Lotions may be formulated with an aqueous or oily base and will in general also contain one or more emulsifying agents, stabilising agents, dispersing agents, suspending agents, thickening agents, or colouring agents. Drops may be formulated with an aqueous or non-aqueous base also comprising one or more dispersing agents, stabilising agents, solubilising agents or suspending agents. They may also contain a preservative.

The compounds of the invention may also be formulated in rectal compositions such as suppositories or retention enemas, e.g. containing conventional suppository bases such as cocoa butter or other glycerides.

The compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For intranasal administration, the compounds of the invention may be formulated as solutions for administration via a suitable metered or unitary dose device or alternatively as a powder mix with a suitable carrier for administration using a suitable delivery device.

A proposed dose of the compounds of the invention is 1 to about 1000 mg per day. It will be appreciated that it may be necessary to make routine variations to the dosage, depending on the age and condition of the patient and the precise dosage will be ultimately at the discretion of the attendant physician or veterinarian. The dosage will also depend on the route of administration and the particular compound selected.

Thus for parenteral administration a daily dose will typically be in the range of 1 to about 100 mg, preferably 1 to 80 mg per day. For oral administration a daily dose will typically be within the range 1 to 300 mg e.g. 1 to 100 mg.

EXAMPLES

In the Intermediates and Examples unless otherwise stated:

All temperatures refer to ° C. Infrared spectra were measured on a FT-IR instrument. Compounds were analysed by direct infusion of the sample dissolved in acetonitrile into a mass spectra operated in positive electro spray (ES$^+$) ionisation mode. Proton Magnetic Resonance ($^1$H-NMR) spectra were recorded at 400 MHz, chemical shifts are reported in ppm downfield (d) from Me$_4$Si, used as internal standard, and are assigned as singlets (s), broad singlets (bs), doublets (d), doublets of doublets (dd), triplets (t), quartets (q) or multiplets (m). A strategy comprising of NOE (Nuclear Overhauser Effect) correlation and/or 1H,15N long range scalar correlations measurements has been implemented in order to allow elucidation of possible regio-isomers structure of compounds of the present invention. Proposed structures were verified by measurement of the vicinity in the space of key hydrogens, thus 1D Nuclear Overhauser difference spectra were used to measure 1H,1H-dipole-dipole correlations.

In cases where NOE measurements were not conclusive, 1H,15N long range scalar correlations were measured via 1H,15N-HMBC experiments. A delay corresponding to an average long range scalar coupling 2,3J(1H,15N) of 6 Hz was set for optimal result.

Column chromatography was carried out over silica gel (Merck AG Darmstaadt, Germany). The following abbreviations are used in the text: EtOAc=ethyl acetate, cHex=cyclohexane, $CH_2Cl_2$=dichloromethane, $Et_2O$=dietyl ether, DMF=N,N'-dimethylformamide, DIPEA=N,N-diisopropylethylamine, DME=ethylene glycol dimethyl ether, MeOH=methanol, $Et_3N$=triethylamine, TFA=trifluoroacetic acid, THF=tetrahydrofuran, DIBAl-H=diisobutylaluminium hydride, DMAP=dimethylaminopyridine, LHMDS=lithiumhexamethyldisilazane, KOtBu=potassium tert-butoxide, NMP=M-methyl-2-pyrrolidinone, MTBE=methyl-tert-butyl ether, IPA=isopropanol, DAST=(diethylamino)sulfur trifluoride, TMSBr=trimethylsilyl bromide, DDQ=2,3-dichloro-5,6-dicyano-1,4-benzoquinone, SCX=strong cation exchanger, Tlc refers to thin layer chromatography on silica plates, and dried refers to a solution dried over anhydrous sodium sulphate, r.t. (RT) refers to room temperature.

Intermediate 1

1-(4-Methoxy-2-methylphenyl)pyrrolidin-2-one

To a solution of $Et_3N$ (156 mL, 1 eq) and 4-methoxy-2-methylaniline (150 g, 1.09 mole) in anh. THF (2.4 L), in a 10 L reaction vessel, at 0° C., under $N_2$, was added dropwise a solution of 4-chlorobutyryl chloride (126 mL, 1 eq) in anh. THF (480 mL). The internal temperature was maintained at circa 10° C. and the reaction mixture was stirred for 1.5 hr. It was cooled down to 0° C. and KOt-Bu 1M/THF (2.64 L, 2.4 eq) was added dropwise over a period of 1.5 hr, keeping the internal temperature <10° C. The reaction mixture was stirred at that temperature for 30 min. Water (1.5 L) was then added slowly (20 min) and the phases were separated. The organic layer was treated with conc. HCl (250 mL) and water (1.26 L) and the phases were separated. The combined aqueous layers were extracted with EtOAc (2.6 L) and the combined organic layers were washed with brine (2 L). The solvent was evaporated and the residue purified by flash chromatography (Biotage 150, EtOAc/cHex 8:2) to give the title compound as a pale brown solid (206 g, 92%).

NMR ($^1$H, $CDCl_3$): δ 7.05 (d, 1H), 6.79-6.72 (m, 2H), 3.75 (s, 3H), 3.64 (t, 2H), 2.18 (s, 6H). MS (m/z): 206 $[MH]^+$.

Intermediate 2

Ethyl 3-{[1-(4-methoxy-2-methylphenyl)pyrrolidin-2-ylidene]amino}but-2-enoate

To a solution of intermediate 1 (8.3 g, 40.49 mmol) in anh. 1,2-dichloroethane (100 mL), at r.t, under $N_2$, was added $POCl_3$ (7.5 mL, 2 eq) dropwise followed by ethyl 3-aminocrotonate (5.17 mL, 1 eq). The reaction mixture was heated at 60° C. for 3.5 hr. It was then cooled down to r.t. and neutralized to pH 7 by the careful addition of sat.aq. $NaHCO_3$. The neutralized solution was extracted with $CH_2Cl_2$ (3×50 mL). The combined organic extracts were washed with sat.aq. NaCl and dried over anh. $Na_2SO_4$. The solids were filtered and the solvent evaporated. The crude product was used as such in the next step (17.8 g).

Alternatively, to a solution of intermediate 91 (3 g, 14.7 mmol) in anh. THF (18 mL), at r.t., under $N_2$, was added ethyl-2-butynoate (2.23 mL, 1.3 eq). The reaction mixture was heated to reflux for 14 hr and was then cooled down to r.t. The reaction mixture was evaporated to dryness. The crude oil was used as such in the next step (5.05 g).

MS (m/z): 317 $[MH]^+$.

Intermediate 3

1-(4-Methoxy-2-methylphenyl)-6-methyl-1,2,3,7-tetrahydro-4H-pyrrolo[2,3-b]pyridin-4-one A solution of intermediate 2 (17.8 g, 55 mmol) in anh. DMF (50 mL) was added dropwise to a suspension of NaH 60%/oil (4.5 g, 2 eq) in anh. DMF. The reaction mixture was heated at 100° C. for 8 hr. More NaH 60%/oil (2.25 g, 1 eq) was added and the reaction mixture was heated for an additional 4 hr. It was cooled down to r.t. and carefully poured in sat.aq. $NH_4Cl$. The aqueous solution was extracted with $CH_2Cl_2$ (5×50 mL) and the combined organic extracts were dried over anh. $Na_2SO_4$. The solids were filtered and the solvent was evaporated. The crude compound was purified by flash chromatography (Biotage 75, $CH_2Cl_2$/MeOH 95:5→80:20). The title compound was obtained as a brown oil (952 mg, 9%, two steps)

Alternatively, to a solution of intermediate 2 (2.46 g, 7.77 mmol) in anh. THF (10 mL), at r.t., under $N_2$, was added 1M t-BuOK/THF (15.6 mL, 2 eq). The reaction mixture was heated to reflux and stirred for 6 hr. The solution was allowed to cool down to r.t., evaporated to circa 10 mL and diluted with MTBE (10 mL). The organic layer was extracted with water (10 mL), the organic phase discarded while the aqueous one was diluted with sat.aq. $NH_4Cl$ (10 mL). The aqueous layer was extracted with $CH_2Cl_2$ (10 mL). The combined organic extracts were evaporated to dryness and the crude product thus obtained was used as such in the next step (1.32 g).

NMR ($^1$H, DMSO-$d_6$): δ 9.8 (b, 1H), 7.08 (d, 1H), 6.80 (d, 1H), 6.75 (dd, 1H), 5.92 (s, 1H), 3.72 (s, 3H), 3.68 (t, 2H), 2.89 (t, 2H), 2.12 (s, 3H), 2.02 (s, 3H). MS (m/z): 271 $[MH]^+$.

Intermediate 4

1-(4-Methoxy-2-methylphenyl)-6-methyl-2,3-dihydro-1H-pyrrolo[2,3-b]pyridin-4-yl trifluoromethanesulfonate To a solution of intermediate 3 (9.0 g, 33.3 mmol) in anh. $CH_2Cl_2$ (64 mL), at r t, under $N_2$, was added pyridine (5.08 mL, 1.8 eq). The solution was cooled down to −20° C. and triflic anhydride (5.9 mL, 1.1 eq) was added dropwise over 50 min. The temperature never exceeded −10° C. The reaction mixture was allowed to warm up to ambient and stirred for 30 min. Sat.aq $NaHCO_3$ (31.2 mL) was added and the phases separated. The organic layer was further washed with water (31.2 mL) and concentrated to an oil, which was passed through a pad of silica gel (12.7 g, EtOAc/cHex 1/9). The crude product thus obtained was diluted with MTBE (38.1 mL) and washed twice with 10% HCl (63.5 mL). The combined aqueous layers were treated with conc. $NH_4OH$ (38.1 mL) and extracted with $CH_2Cl_2$ (25.4 mL). The organic layer was further washed with 10% NaCl (12.7 mL) and evaporated to an oil. The oil was dissolved with IPA (38.1 mL) and seeded with authentic intermediate 4 (0.02 g). The suspension was stirred for 30 min. Water (38 mL) was added over 30 min and the mixture left standing for 1.5 hr. The suspension was filtered, the cake washed with a 1:1 mixture of IPA/water(12.7 mL), collected and dried in the oven at 40° C. under high vacuum for 14 hr. The title compound was obtained as a pale yellow solid (3.8 g, 42%).

NMR ($^1$H, DMSO-d$_6$): δ 7.17 (d, 1H), 6.85 (d, 1H), 6.77 (dd, 1H), 6.40 (s, 1H), 3.89 (t, 2H), 3.73 (s, 3H), 3.16 (t, 2H), 2.17-2.11 (2s, 6H) M/S (m/z): 403 [MH]$^+$

Intermediate 5

4-Iodo-6-methyl-1-[2-methyl-4-(methyloxy)phenyl]-2,3-dihydro-1H-pyrrolo[2,3-b]pyridine To a solution of intermediate 4 (913 mg, 2.27 mmol) in anh. NMP (7 mL) was added KI (1.13 g, 3 eq) and the reaction mixture was stirred at 150° C. for 18 hr. It was then cooled down to r.t. and diluted in water/sat.aq. NaCl. The aqueous phase was extracted with EtOAc (3×30 mL) and the combined organic extracts were dried over anh. Na$_2$SO$_4$. The solids were filtered and the solvent evaporated. The crude product was purified by flash chromatography (silica gel, cHex/EtOAc 9:1) to give the title compound as a clear oil, which solidified upon standing (681 mg, 79%).

NMR ($^1$H, CDCl$_3$): δ 7.14 (d, 1H), 6.81-6.74 (m, 2H), 6.70 (s, 1H), 3.84 (t, 2H), 3.81 (s, 3H), 3.03 (t, 2H), 2.22 (s, 6H). MS (m/z): 381 [MH]$^+$.

Intermediate 6

N-(2-Chloroethyl)-3-({[(2-chloroethyl)amino]carbonyl}amino)-1H-pyrazole-1-carboxamide To a solution of 3-aminopyrazole (500 mg, 6 mmol) in anh. DMF (3 mL), at 0° C., under N$_2$, was added 3-chloroethyl isocyanate (1.53 mL, 3 eq) and the reaction mixture was stirred at r.t. for 2 hr, after which the solvent was evaporated. The crude product was purified by flash chromatography (silica gel, cHex/EtOAc 1:1) to give the title compound (1.593 g, 89%).

NMR ($^1$H, DMSO): δ 9.20 (s, 1H), 8.26 (m, 1H), 8.10 (d, 1H), 7.25 (bs, 1H), 6.37 (d, 1H), 3.74 (m, 2H), 3.66 (m, 2H), 3.58 (m, 2H), 3.46 (m, 2H). MS (m/z): 296 [MH]$^+$.

Intermediate 7

N-(2-Chloroethyl)-3-(2-oxoimidazolidin-1-yl)-1H-pyrazole-1-carboxamide

To a solution of intermediate 6 (100 mg, 0.34 mmol) in anh. THF (4 mL), at r.t., under N$_2$, was added KOt-Bu (42 mg, 1.1 eq) and the reaction mixture was stirred for 2 hr. Water (0.5 mL) was added and the solvent was evaporated. The aqueous phase was diluted with H$_2$O and extracted with EtOAc (3×20 mL). The combined organic extracts were dried over anh. Na$_2$SO$_4$. The solids were filtered and the solvent evaporated. The crude product was purified by flash chromatography (silica gel, EtOAc/cHex 8:2, then 9:1) to give the title compound as a white solid (39 mg, 44%)

NMR ($^1$H, DMSO): δ 8.18 (bt, 1H), 8.11 (d, 1H), 7.14 (bs, 1H), 6.75 (d, 1H), 3.89 (m, 2H), 3.73 (m, 2H), 3.56 (m, 2H), 3.40 (m, 2H). MS (m/z): 258 [MH]$^+$.

Intermediate 8

1-(1H-Pyrazol-3-yl)imidazolidin-2-one

To a solution of intermediate 7 (190 mg, 0.74 mmol) in a 2:1 mixture of MeOH/H$_2$O (15 mL), at r.t., under N$_2$, was added LiOH (177 mg, 10 eq) and the reaction mixture was heated at 80° C. for 3 hr. It was cooled down to r.t. and neutralized to pH 7 with 2M HCl. Silica gel was then added and the solvents were evaporated. The adsorbed crude product was purified by flash chromatography (silica gel, EtOAc/MeOH 9:1) to give the title compound as a white solid (80 mg, 71%)

NMR ($^1$H, DMSO): δ 12.10 (bs, 1H), 7.6 (s, 1H), 6.7 (s, 1H), 6.4 (s, 1H), 3.8 (t, 2H), 3.4 (t, 2H). MS (m/z): 152 [MH]$^+$.

Intermediate 9

4-Chloro-N-[1-(4-chlorobutanoyl)-1H-pyrazol-3-yl]butanamide

To a solution of 3-aminopyrazole (300 mg, 3.61 mmol) in anh. CH$_2$Cl$_2$ (6 mL), at r.t., under N$_2$, was added K$_2$HPO$_4$ (1.26 g, 2 eq) and the reaction mixture was stirred at r.t. for 15 min. 4-Chloro-butyryl chloride (406 μL, 3.6 mmol) was then added and the reaction mixture was stirred for 24 hr. It was then poured into water and the phases were separated. The aqueous layer was extracted with EtOAc (2×20 mL) and the combined organic extracts were dried over anh. Na$_2$SO$_4$. The solids were filtered and the solvent evaporated. The crude product was purified by flash chromatography (silica gel, cHex/EtOAc 7:3) to give the title compound as a white solid (354 mg, 34%)

NMR ($^1$H, CDCl$_3$): δ 8.09 (d, 1H), 7.83 (bs, 1H), 6.98 (s, 1H), 3.64 (m, 2H), 3.17 (m, 1H), 2.57 (m, 1H), 2.21 (m, 2H). MS (m/z): 292 [M]$^+$.

Intermediate 10

1-(1H-Pyrazol-3-yl)pyrrolidin-2-one

To a suspension of NaH 80%/oil (31 mg, 1.1 eq) in anh. DMF (1.5 mL), at r.t., under N$_2$, was added a solution of intermediate 9 (340 mg, 1.16 mmol) in anh. DMF (1 mL). The reaction mixture was stirred at r.t. for 1 hr, after which it was quenched carefully with water. The aqueous phase was extracted with EtOAc (3×20 mL) and the combined organic extracts were washed with sat.aq. NaCl and dried over anh. Na$_2$SO$_4$. The solids were filtered and the solvent evaporated. The crude product (70 mg, 0.27 mmol) was dissolved in anh. MeOH (3 mL), at r.t., under N$_2$, and 1M MeONa/MeOH was added until pH 9 was reached. The reaction mixture was stirred at r.t. for 30 min and water was added. The aqueous phase was extracted with EtOAc (3×20 mL) and the combined organic extracts were washed with sat.aq. NaCl and dried over anh. Na$_2$SO$_4$. The solids were filtered and the solvent evaporated. The crude product was purified by flash chromatography (silica gel, cHex/EtOAc 7:3) to give the title compound as a white solid (35 mg, 20%).

NMR ($^1$H, CDCl$_3$): δ 7.46 (s, 1H), 6.55 (s, 1H), 3.90 (t, 2H), 2.59 (t, 2H), 2.18 (m, 2H), MS (m/z): 152 [M]$^+$.

Intermediate 11

N-(3-Chloropropyl)-3-({[(3-chloropropyl)amino]carbonyl}amino)-1H-pyrazole-1-carboxamide To a solution of 3-aminopyrazole (500 mg, 6 mmol), in anh. DMF (10 mL), at r.t., under N$_2$, was added 3-chloropropyl isocyanate (1.2 mL, 2 eq) and the reaction was stirred for 24 hr. The reaction was not complete and more isocyanate (1.2 mL, 2 eq) was added. The reaction mixture was stirred for an additional 48 hr. It was then poured into $CH_2Cl_2$/sat.aq. NaCl and the phases were separated. The aqueous layer was extracted with $CH_2Cl_2$ (2×20 mL) and the combined organic extracts were dried over anh. $Na_2SO_4$. The solids were filtered and the solvent evaporated. The crude product was purified by flash chromatography (Biotage 40, cHex/EtOAc 7:3) to give the title compound as a white solid (620 mg, 32%).

NMR ($^1$H, DMSO): δ 9.05 (s, 1H), 8.25 (t, 1H), 8.08 (d, 1H), 7.17 (t, 1H), 6.30 (d, 1H), 4.7-4.6 (m, 4H), 3.37 (q, 2H), 3.26 (q, 2H), 2.05-1.87 (m, 4H). MS (m/z): 322 [MH]$^+$.

Intermediate 12

N-(3-Chloropropyl)-3-(2-oxotetrahydropyrimidin-1 (2H)-yl)-1H-pyrazole-1-carboxamide To a solution of intermediate 11 (620 mg, 1.93 mmol) in anh. THF (20 mL), at r.t., under $N_2$, was added KOt-Bu (237 mg, 1.1 eq). The reaction mixture was stirred at r.t. for 2 hr. Water was then added and the solvent was evaporated. The aqueous phase was extracted with EtOAc (3×20 mL) and the combined organic extracts were dried over anh. $Na_2SO_4$. The solids were filtered and the solvent evaporated. The crude product was purified by flash chromatography (Flash Master, 10 g $SiO_2$, cHex/EtOAc 7:3, then 100% EtOAc) to give the title compound as a white solid (200 mg, 37%)

NMR ($^1$H, DMSO): δ 8.23 (t, 1H), 8.06 (d, 1H), 6.93 (bs, 1H), 6.82 (d, 1H), 3.86 (t, 2H), 3.57 (t, 2H), 3.34 (m, 2H), 3.19 (m, 2H), 1.98 (m, 2H), 1.91 (m, 2H). MS (m/z): 286 [MH]$^+$.

Intermediate 13

1-(1H-Pyrazol-3-yl)tetrahydropyrimidin-2(1H)-one

A solution of intermediate 12 (180 mg, 0.63 mmol) and LiOH (265 mg, 10 eq) in a 2:1 mixture of MeOH/$H_2O$ (7.5 mL), in a sealed vial, was subjected to microwave irradiation (80° C.) for 10 min. The reaction mixture was then cooled down to r.t., and the solvent was evaporated to dryness. The residue was purified on an SCX cartridge (EtOAc/MeOH 8:2, then 100% MeOH) to give the title compound as a white solid (102 mg, 98%)

NMR ($^1$H, DMSO): δ 12.13 (bs, 1H), 7.50 (s, 1H), 6.60 (bs, 1H), 6.46 (s, 1H), 3.73 (m, 2H), 3.15 (m, 2H), 1.88 (m, 2H). MS (m/z): 167 [MH]$^+$.

Intermediate 14

3-Bromo-1-(triphenylmethyl)-1H-pyrazole

To a solution of 3-bromo-pyrazole (2.0 g, 13.6 mmol) in anh. $CH_2Cl_2$ (40 mL), at r.t., under $N_2$, were added triphenylmethyl chloride (4.17 g, 1.1 eq) and $Et_3N$ (2.1 mL, 1.1 eq). The reaction mixture was stirred at r.t. for 4 hr. It was poured into water/$CH_2Cl_2$. The phases were separated and the aqueous layer was further extracted with $CH_2Cl_2$ (2×30 mL). The combined organic extracts were dried over anh. $Na_2SO_4$, the solids were filtered and the solvent evaporated. The residue was purified by flash chromatography (silica gel, 100% $CH_2Cl_2$) to give the title compound as a white solid (3.39 g, 64%).

NMR ($^1$H, DMSO-d$_6$): δ 7.34 (m, 10H), 7.01 (m, 6H), 6.45 (d, 1H). MS (m/z): 412 [M+Na]$^+$.

Intermediate 15

3-[1-(Triphenylmethyl)-1H-pyrazol-3-yl]-1,3-oxazolidin-2-one

A mixture of intermediate 14 (389 mg, 1 mmol), 1,3-oxazolidin-2-one (87 mg, 1 mmol), CuI (20 mg, 10 mol %), (1R,2R)-diaminomethylcyclohexane (43 mg, 30 mol %) and $K_2CO_3$ (414 mg, 3 mmol) in anh. NMP (2 mL) in a seaded vial was stirred at 130° C. for 4 hr. It was poured into water/EtOAc. The phases were separated and the aqueous layer was further extracted with EtOAc (2×10 mL). The combined organic extracts were dried over anh. $Na_2SO_4$, the solids were filtered and the solvent evaporated. The residue was purified by flash chromatography (silica gel, EtOAc/cHex 2:8) to give the title compound as a white solid (210 mg, 53%).

NMR ($^1$H, CDCl$_3$): δ 7.28 (m, 9H), 7.21 (d, 1H), 7.13 (m, 6H), 6.64 (d, 1H), 4.40 (t, 2H), 3.98 (t, 2H). MS (m/z): 418 [M+Na]$^+$.

Intermediate 16

3-(1H-Pyrazol-3-yl)-1,3-oxazolidin-2-one

To a solution of intermediate 15 (210 mg, 0.53 mmol) in anh. MeOH (4 mL), under $N_2$, was added trifluroacetic acid (0.2 mL, 2.66 mmol). The reaction mixture was subjected to microwave irradiation (100° C.) for 15 min. The solvent was evaporated and the residue was purified on an SCX cartridge (100% $CH_2Cl_2$, then 0.5M $NH_3$/MeOH) to give the title compound as a white solid (30 mg, 37%).

NMR ($^1$H, DMSO-d$_6$): δ 7.64 (d, 1H), 6.40 (d, 1H), 4.41 (t, 2H), 3.97 (t, 2H). MS (m/z): 155 [MH]$^+$.

Intermediate 17

N-1H-Pyrazol-3-ylacetamide

To a solution of 3-aminopyrazole (20 g, 0.24 mol) in $H_2O$ (36 mL), at 5-10° C., was slowly added NaHCO$_3$ (9.1 g, mol, 3 eq) and then Ac$_2$O (6.79 ml, 2 eq). The reaction mixture was refluxed for 8 hr. It was cooled down to r.t. and was left standing at this temperature for 12 hr to allow crystallization. The white solid was filtered (12.9 g) and the mother liquor volume was reduced. A second batch of white solid (3.4 g) was obtained after crystallization. The two batches were combined to give the title compound (16.3 g, 54%).

NMR ($^1$H, DMSO-d$_6$): δ 12.22 (bs, 1H), 10.28 (bs, 1H), 7.53 (bs, 1H), 6.43 (bs, 1H), 1.96 (s, 1H). MS (m/z): 126 [MH]$^+$, 148 [M+Na]$^+$.

Intermediate 18

N-(1-{6-Methyl-1-[2-methyl-4-(methyloxy)phenyl]-2,3-dihydro-1H-pyrrolo[2,3-b]pyridin-4-yl}-1H-pyrazol-3-yl)acetamide A mixture of intermediate 5 (500 mg, 1.32 mmol), intermediate 17 (329 mg, 2 eq.), CuI (50 mg, 0.2 eq.), $K_2CO_3$ (382 mg, 2.1 eq.), dodecane (60 μL, 0.2 eq.) and (+/−)-trans-1,2-diaminocyclohexane (45 μL, 0.3 eq.) in anh. NMP (5 mL), in a sealed vial, was heated at 150° C. for 4 hr. It was cooled down to r.t. and poured into sat.aq. NH$_4$Cl. EtOAc was added and the phases were separated. The aqueous layer was further extracted with EtOAc (2×10 mL). The combined organic extracts were dried over anh. $Na_2SO_4$, the solids were filtered and the solvent evaporated. The residue was purified on an SCX cartridge (silica gel, $CH_2Cl_2$, then MeOH, then conc. $NH_4OH$ in MeOH, 25:75) and then by flash chromatography (cHex/EtOAc 7:3) to give the title compound as a white solid (358 mg, 72%).

NMR ($^1$H, DMSO-$d_6$): δ 10.62 (bs, 1H), 8.24 (d, 1H), 7.15 (d, 1H), 6.84 (d, 1H), 6.78-6.73 (m, 3H), 3.83 (t, 2H), 3.74 (s, 3H), 3.4 (t, 2H), 2.16 (s, 3H), 2.14 (s, 3H), 2.04 (s, 3H). MS (m/z): 378 [MH]$^+$.

Intermediate 19

1-{6-Methyl-1-[2-methyl-4-(methyloxy)phenyl]-2,3-dihydro-1H-pyrrolo[2,3-b]pyridin-4-yl}-1H-pyrazol-3-amine To a dispersion of intermediate 18 (358 mg, 0.95 mmol) in EtOH (7 mL), at r.t., was added 25% NaOH (2.5 mL) and the reaction mixture was subjected to microwave irradiation (130° C.) for 20 min. The EtOH was evaporated and the crude product was partitioned between EtOAc and sat.aq. NaCl. The phases were separated and the aqueous layer was further extracted with EtOAc (2×10 mL). The combined organic extracts were dried over anh. $Na_2SO_4$, the solids were filtered and the solvent evaporated to give the title compound (282 mg, 89%) which was used in the next step without any further purification.

NMR ($^1$H. DMSO-$d_6$): δ 7.98 (d, 1H), 7.12 (d, 1H), 6.83 (d, 1H), 6.75 (dd, 1H), 6.67 (s, 1H), 5.77 (d, 1H), 5.10 (bs, 2H), 3.78 (t, 2H), 3.74 (s, 3H), 3.35 (t, 2H), 2.13 (s, 3H), 2.12 (s, 3H). MS (m/z): 336 [MH]$^+$.

Intermediate 20

Ethyl N-(1-{6-methyl-1-[2-methyl-4-(methyloxy)phenyl]-2,3-dihydro-1H-pyrrolo[2,3-b]pyridin-4-yl}-1H-pyrazol-3-yl)glycinate To a solution of intermediate 19 (200 mg, 0.6 mmol) in anh. DMF (5 mL), at r.t., under $N_2$, was added NaH 60%/oil (26 mg, 1.1 eq). The reaction mixture was stirred at r.t. for 20 min, ethyl 2-bromoacetate (73 μL, 1.1 eq) was then added dropwise and the reaction mixture was heated at 80° C. Continuous additions of the alkyl bromide were done at 80° C. over a period of 7.2 h (5×36 μL, 5×0.55 eq). The reaction mixture was cooled down to r.t. and poured into $H_2O$. EtOAc was added and the phases were separated. The aqueous layer was further extracted with EtOAc (2×10 mL). The combined organic extracts were dried over anh. $Na_2SO_4$, the solids were filtered and the solvent evaporated. The residue was purified by flash chromatography (silica gel, cHex/EtOAc 7:3) to give the title compound as a yellow oil (155 mg, 62%).

NMR ($^1$H, DMSO-$d_6$): δ 8.09 (d, 1H), 7.13 (d, 1H), 6.83 (d, 1H), 6.76 (dd, 1H), 6.37 (s, 1H), 6.17 (t, 1H), 5.86 (d, 1H), 5.73 (s, 1H), 4.09 (q, 2H), 3.89 (d, 2H), 3.77 (t, 2H), 3.74 (s, 3H), 3.36 (t, 2H), 2.13 (bs, 6H), 1.17 (t, 3H). MS (m/z): 422 [MH]$^+$.

Intermediate 21

2-[(1-{6-Methyl-1-[2-methyl-4-(methyloxy)phenyl]-2,3-dihydro-1H-pyrrolo[2,3-b]pyridin-4-yl}-1H-pyrazol-3-yl)amino]ethanol To a cold (−78° C.) solution of 1N $LiAlH_4$/THF (0.5 mL, 2.7 eq), under $N_2$, was added dropwise a solution of intermediate 20 (77.5 mg, 0.184 mmol) in anh. THF (5 mL). The reaction mixture was stirred at −78° C. for 20 min. Continuous additions of 1N $LiAlH_4$/THF were done at this temperature over a period of 40 min (3×200 μL, 3×1.09 eq). To the reaction mixture was added water (42 μL), 1N NaOH (42 μL) and water (125 μL) and a precipitate was formed. The solid was filtered and washed with EtOAc (2×) and $CH_2Cl_2$ (2×). The combined organic extracts were concentrated and the residue was purified by flash chromatography (silica gel, cHex/EtOAc 7:3) to give the title compound as a yellow solid (25 mg, 36%).

NMR ($^1$H, DMSO-$d_6$): δ 8.04 (d, 1H), 7.13 (d, 1H), 6.83 (d, 1H), 6.76 (dd, 1H), 6.66 (s, 1H), 5.82 (d, 1H), 5.58 (t, 1H), 4.59 (t, 1H), 3.78 (t, 2H), 3.74 (s, 3H), 3.55 (q, 2H), 3.40 (t, 2H), 3.20 (q, 2H), 2.13 (bs, 6H). MS (m/z): 380 [MH]$^+$.

Intermediate 22

3-[(1-{6-Methyl-1-[2-methyl-4-(methyloxy)phenyl]-2,3-dihydro-1H-pyrrolo[2,3-b]pyridin-4-yl}-1H-pyrazol-3-yl)amino]-1-propanesulfonic acid To a suspension of intermediate 19 (25 mg, 0.0746 mmol) in n-BuOH (1 mL), at r.t., under $N_2$, was added 1,2-oxathiolane 2,2-dioxide (30 μL, 3 eq). The reaction mixture was subjected to microwave irradiation (20+60+60 min, T=150/180° C.). The solvent was evaporated and the residue was purified by flash-chromatography (silica gel, 100% EtOAc→7:3 EtOAc/sol. $NH_3$ in MeOH (0.5 M)) and SCX cartridge (Eluents: MeOH and a sol. of $NH_3$ in MeOH (0.5 M)) to give the title compound as a yellow oil (10 mg, 30%).

NMR ($^1$H, CDCl$_3$): δ 7.54 (bs, 1H), 7.05 (d, 1H), 6.72 (m, 1H), 6.66 (m, 1H), 6.48 (bs, 1H), 5.78 (bs, 1H), 3.72 (m, 5H), 3.3 (m, 4H), 2.97 (m, 2H), 2.03-2.2 (m, 8H). MS (m/z): 458 [MH]$^+$.

Intermediate 23

Phenyl (1-{6-methyl-1-[2-methyl-4-(methyloxy)phenyl]-2,3-dihydro-1H-pyrrolo[2,3-b]pyridin-4-yl}-1H-pyrazol-3-yl)carbamate To a suspension of intermediate 19 (391 mg, 1.17 mmol) in anh. $CH_2Cl_2$ (8 mL), at 0° C., under $N_2$, were added pyridine (103 μL, 1.1 eq) and phenyl chloroformate (161 μL, 1.1 eq). The reaction mixture was stirred at r.t. for 1 hr. The solvent was evaporated in vacuo, sat.aq. NaCl (50 mL) was then added and the solution extracted with EtOAc (3×15 mL). The combined organic extracts were dried over anh. $Na_2SO_4$, the solids were filtered and the solvents evaporated in vacuo. The crude compound thus obtained was purified by flash chromatography (silica gel, MeOH-Ammonia solution in MeOH 0.5 M) to give 284 mg (53%) of the title compound as a white solid.

NMR ($^1$H, CDCl$_3$): δ 10.8 (bs, 1H) 8.28 (d, 1H), 7.39 (m, 2H), 7.18 (m, 4H), 6.73 (dd, 1H), 6.64 (s, 1H), 3.81 (t, 2H), 3.72 (s, 3H), 3.32 (t, 2H), 2.14 (s, 3H), 2.12 (s, 3H). MS (m/z): 456 [MH]$^+$.

Intermediate 24

Phenyl (1-{6-methyl-1-[2-methyl-4-(methyloxy)phenyl]-2,3-dihydro-1H-pyrrolo[2,3-b]pyridin-4-yl}-1H-pyrazol-3-yl)carbamate A mixture of intermediate 23 (284 mg, 0.62 mmol), pyridine (50 μL, 1.2 eq) and 2,2-bis(ethyloxy)ethanamine (108 μL, 1.2 eq) was heated for 3 hr at 60° C. $H_2O$ (50 mL) was then added and the solution extracted with $CH_2Cl_2$ (3×15 mL). The combined organic extracts were dried over anh. $Na_2SO_4$, the solids were filtered and the solvent evaporated in vacuo. The crude compound thus obtained was purified by flash chromatography (silica gel, cHex/EtOAc 1:1) to give 214 mg (84%) of the title compound as a white solid.

NMR (¹H, CDCl₃): δ 9.21 (s, 1H), 8.24 (d, 1H), 7.15 (d, 1H), 6.95 (bs, 1H), 6.95 (d, 1H), 6.78 (dd, 1H), 6.72 (s, 1H), 6.42 (s, 1H), 4.5 (m, 1H), 3.82 (t, 2H), 3.60 (m, 1H), 3.48 (m, 1H), 3.65 (s, 3H), 3.3 (s, 6H), 3.23 (t, 2H), 3.16 (s, 3H), 2.14 (s, 3H). MS (m/z): 495 [MH]⁺.

Intermediate 25

3-Methyl-1-[1-(triphenylmethyl)-1H-pyrazol-3-yl]-2 (1H)-pyridinone

A solution of intermediate 14 (300 mg, 0.77 mmol), 3-methylpyridinone (168 mg, 1 eq), CuI (146 mg, 1 eq), K₂CO₃ (223 mg, 2.1 eq), N N'-dimethyl trans-cyclohexanediamine (109 mg, 0.5 eq) in anh. NMP (4 mL) was heated at 150° C. for 24 hr. Sat.aq. NH₄Cl (100 mL) was then added and the mixture extracted with CH₂Cl₂ (250 mL). The organic layer was dried over anh. Na₂SO₄, the solids were filtered and the solvent evaporated in vacuo. The crude compound thus obtained was purified by flash chromatography (silica gel, cHex/EtOAc 95:5) to give 80 mg (25%) of the title compound as white solid.

NMR (¹H, CDCl₃): δ 7.76(d, 1H), 7.30(m, 1H), 7.15 (m, 6H), 6.98(d, 1H), 6.06 (t, 1H), 2.15 (s, 3H). MS (m/z): 440 [M+Na].

Intermediate 26

3-Methyl-1-(1H-pyrazol-3-yl)-2(1H)-pyridinone

CF₃COOH (3 mL) was added to a solution of intermediate 25 (80 mg, 0.19 mmol) in an anh. mixture of MeOH/CH₂Cl₂ 2:1 (3 mL) at r.t., under N₂. The solution was heated at 80° C. for 18 hr. The solvents were evaporated in vacuo. The crude compound thus obtained was purified on an SCX cartridge (1 g, preconditioned with CH₂Cl₂) to give 13 mg (39%) of the title compound as a white solid.

NMR (¹H, CDCl₃): δ 7.61(d, 1H), 7.55(s, 1H), 7.24 (m, 1H), 7.1(d, 1H), 6.76 (d, 1H), 6.16 (t, 1H), 2.15 (s, 3H). MS (m/z): 176 [MH]⁺.

Intermediate 27

2-[1-(Triphenylmethyl)-1H-pyrazol-3-yl]-3(2H)-pyridazinone

A solution of intermediate 14 (200 mg, 0.52 mmol), pyridazinone (50 mg, 1 eq), CuI (100 mg, 1 eq), K₂CO₃ (148 mg, 2 eq) and N N'-dimethyl trans-cyclohexanediamine (73 mg, 0.5 eq.) in anh. NMP (4 mL) was heated at 150° C. for 8 hr. Sat.aq. NH₄Cl (100 mL) was then added and the solution extracted with CH₂Cl₂ (250 mL). The organic layer was dried over anh. Na₂SO₄, the solids were filtered and the solvents evaporated in vacuo. The crude compound thus obtained was purified by flash chromatography (silica gel, cHex/EtOAc 1:9) to give a solution of the title compound in NMP, which was used in the next step without further purification.

MS (m/z): 443 [M+K], 427 [M+Na].

Intermediate 28

2-(1H-Pyrazol-3-yl)-3(2H)-pyridazinone

The solution of intermediate 27 obtained above was dissolved in a mixture of MeOH/CH₂Cl₂ 2:1 (3 mL) and CF₃COOH (2.5 mL) was added, at r.t., under N₂. The reaction mixture was heated at 80° C. for 4 hr. The solvents were evaporated in vacuo. The crude compound thus obtained was purified on an SCX cartridge (1 g, preconditioned with CH₂Cl₂) to give 20 mg (24%, two steps) of the title compound as a white solid.

NMR (¹H, CDCl₃): δ 7.91 (d, 1H), 7.59(m, 1H), 7.24 (m, 1H), 7.07(m, 1H), 6.76 (d, 1H). MS (m/z): 163 [MH]⁺.

Intermediate 29

1-Acetyl-3-{1-[1-(4-hydroxy-2-methylphenyl)-6-methyl-2,3-dihydro-1H-pyrrolo[2,3-b]pyridin-4-yl]-1H-pyrazol-3-yl}-2-imidazolidinone To a solution of example 1-6 (80 mg, 0.179 mmol) in anh. CH₂Cl₂ (1.8 mL), at r.t., under N₂, was added BBr₃ 1.0M/CH₂Cl₂ (0.72 mL, 5 eq) dropwise. The reaction mixture was stirred at r.t. for 90 min. MeOH (1 mL) was added and the solvent was evaporated. The residue was taken up in EtOAc/sat.aq. NaHCO₃ and the phases were separated. The aqueous layer was extracted with CH₂Cl₂ (2×10 mL) and the combined organic extracts were dried over anh. Na₂SO₄. The solids were filtered and the solvent evaporated. The crude compound was further purified by flash chromatography (silica gel, 100% EtOAc→5% MeOH/EtOAc) to give the title compound as a white solid (29 mg, 37%).

NMR (¹H, DMSO-d₆): δ 9.3 (s, 1H), 8.40 (d, 1H), 7.00 (d, 1H), 6.85 (d, 1H), 6.75 (s, 1H), 6.65 (d, 1H), 6.60 (dd, 1H), 4.00-3.70 (m, 6H), 3.40 (t, 2H), 2.45 (s, 3H), 2.15 (s, 3H), 2.05 (s, 3H). MS (m/z): 433 [MH]⁺.

Intermediate 30

1-Acetyl-3-(1-{1-[4-(ethyloxy)-2-methylphenyl]-6-methyl-2,3-dihydro-1H-pyrrolo[2,3-b]pyridin-4-yl}-1H-pyrazol-3-yl)-2-imidazolidinone To a solution of intermediate 29 (13.6 mg, 0.0315 mmol) in anh. DMF (1 mL), at r.t., under N₂, was added NaH 60%/oil (2.5 mg, 2 eq) and the reaction mixture was stirred at r.t. for 20 min. Iodoethane (10 μL, 4 eq) was added and the reaction mixture was stirred at r.t. for 1 hr. It was poured into EtOAc/sat.aq. NaCl and the phases were separated. The organic layer was washed with sat.aq. NaCl (2×10 mL) and dried over anh. Na₂SO₄. The solids were filtered and the solvent was evaporated. The crude compound was purified by flash chromatography (silica gel, cHex/EtOAc 1:1). The mixed fraction were re-purified by flash chromatography (silica gel, cHex/EtOAc 7:3). The title compound was obtained as a white solid (5 mg, 34%)

NMR (¹H,): δ 7.87 (d, 1H), 7.13 (d, 1H), 6.95 (d, 1H), 6.79 (d, 1H), 6.74 (d, 1H), 6.53 (s, 1H), 4.11-3.97 (m, 6H), 3.86 (t, 2H), 3.43 (t, 2H), 2.58 (s, 3H), 2.31 (s, 3H), 2.09 (s, 3H), 1.39 (t, 3H). MS (m/z): 461 [MH]⁺.

Intermediate 31

1-Acetyl-3-[1-(6-methyl-1-{2-methyl-4-[(1-methylethyl)oxy]phenyl}-2,3-dihydro-1H-pyrrolo[2,3-b]pyridin-4-yl)-1H-pyrazol-3-yl]-2-imidazolidinone To a solution of intermediate 29 (14 mg, 0.032 mmol) in anh. DMF (1 mL), at r.t., under N₂, was added NaH 60%/oil (3 mg, 2 eq) and the reaction mixture was stirred at r.t. for 20 min. 2-Iodopropane (13 μL, 4 eq) was added and the reaction mixture was stirred at r.t. for 1 hr. It was poured into EtOAc/sat.aq. NaCl and the phases were separated. The organic layer was washed with sat.aq. NaCl (2×10 mL) and dried over anh.

Na$_2$SO$_4$. The solids were filtered and the solvent was evaporated. The crude compound was purified by flash chromatography (silica gel, cHex/EtOAc 2:8). The title compound was obtained as a clear oil (11 mg, 79%) in an inseparable 2:1 mixture with 1-(1-methylethyl)-3-[1-(6-methyl-1-{2-methyl-4-[(1-methylethyl)oxy]phenyl}-2,3-dihydro-1H-pyrrolo[2,3-b]pyridinyl)-1H-pyrazol-3-yl]-2-imidazolidinone.
MS (m/z): 475 [MH]$^+$.

Intermediate 32

1-(2,4-Dichlorophenyl)-2-pyrrolidinone

As in intermediate 1, except that 2,4-dichloroaniline was used instead of 4-methoxy-2-methylaniline.
NMR ($^1$H, CDCl$_3$): δ 7.18-7.35 (m, 3H), 3.72 (t, 2H), 2.53 (t, 2H), 2.22 (t, 2H). MS (m/z): 230 [MH]$^+$.

Intermediate 33

Ethyl 1-(2,4-dichlorophenyl)-2-oxo-3-pyrrolidinecarboxylate

To a solution of intermediate 32 (3.6 g, 15.65 mmol) in (EtO)$_2$CO (25.2 mL, 13.2 eq), at r.t., under N$_2$, was added t-BuOK 1M/THF (47 mL, 3 eq) dropwise. The stirred reaction mixture was heated at 80° C. for 2 hr, then it was cooled to r.t. and poured on ice. The mixture was then acidified with 6N HCl, extracted with CH$_2$Cl$_2$ (300 mL), washed with sat.aq. NaHCO$_3$ (100 mL), sat.aq. NaCl (100 mL) and water (100 mL). The organic layer was dried over anh. Na$_2$SO$_4$, the solids were filtered and the solvent evaporated. The crude product was purified by flash chromatography (silica gel, cHex/EtOAc 6:4) to give the title compound as a yellow oil (3.2 g, 67%).
NMR ($^1$H, DMSO-d$_6$): δ 7.61 (s, 1H), 7.44 (m, 2H), 4.16 (q, 2H), 3.80 (m, 2H), 3.61 (t, 1H), 2.51 (m, 2H), 1.24 (t, 3H). MS (m/z): 302 [MH]$^+$.

Intermediate 34

Ethyl 1-(2,4-chlorophenyl)-2-{[3-(ethyloxy)-1-methyl-3-oxo-1-propen-1-yl]imino}-3-pyrrolidinecarboxylate To a mixture of intermediate 33 (0.5 g, 1 eq) and ethyl(2Z)-3-amino-2-butenoate (0.43 g, 2 eq), was added POCl$_3$ (4 mL, 26 eq) and the resulting reaction mixture was stirred at 100° C. for 4 hr. The reaction mixture was then cooled to r.t., evaporated, poured on ice, neutralized with sat.aq. NaHCO$_3$ and extracted with EtOAc (200 mL). The organic layer was dried over anh. Na$_2$SO$_4$, the solids were filtered and the solvent evaporated. The crude product was used in the next step without further purification.
MS (m/z): 413 [M]$^+$.

Intermediate 35

1-(2,4-Dichlorophenyl)-6-methyl-1,2,3,7-tetrahydro-4H-pyrrolo[2,3-b]pyridin-4-one A solution of crude intermediate 34 in anh. DMF (10 mL) was added to a suspension of NaH 60%/oil (111 mg, 2 eq) in anh. DMF (10 mL), at r.t., under N$_2$. The reaction mixture was heated at 100° C. for 6 hr. The mixture was then cooled to r.t. and the pH adjusted to 5 with sat.aq. NH$_4$Cl. The reaction mixture was then partitioned between EtOAc/sat.aq. NH$_4$Cl (200 mL/100 mL). The phases were separated and the organic layer was dried over anh. Na$_2$SO$_4$, the solids were filtered, the solvent evaporated and the crude product was purified by flash chromatography (silica gel, cHex/EtOAc 1:1→EtOAc/MeOH 1:1) to give the title compound as a brown oil (0.038 g, 7%, two steps).
NMR ($^1$H, CDCl$_3$): δ 7.33 (m, 2H), 7.17 (m, 1H), 6.00 (s, 1H), 2.88 (t, 2H), 2.98 (t, 2H), 2.22 (s, 3H). MS (m/z): 295 [M]$^+$.

Intermediate 36

1-(2,4-Dichlorophenyl)-6-methyl-2,3-dihydro-1H-pyrrolo[2,3-b]pyridin-4-yl trifluoromethanesulfonate As in intermediate 4.
NMR ($^1$H, CDCl$_3$): δ 7.48 (s, 1H), 7.34 (d, 1H), 7.26 (d, 1H), 6.35 (s, 1H), 4.01 (t, 2H), 3.25 (t, 2H), 2.32 (s, 3H). MS (m/z): 427 [M]$^+$.

Intermediate 37

1-(2,4-Dichlorophenyl)-4-iodo-6-methyl-2,3-dihydro-1H-pyrrolo[2,3-b]pyridine

As in intermediate 5.
NMR ($^1$H, CDCl$_3$): δ 7.42 (m, 3H), 6.81 (s, 1H), 3.96 (t, 2H), 3.04 (t, 2H), 2.24 (s, 3H). MS (m/z): 405 [M]$^+$.

Intermediate 38

Ethyl 2-chloro-6-methyl-4-[3-(2-oxoimidazolidin-1-yl)-1H-pyrazol-1-yl]nicotinate To a solution of intermediate 8 (9.73 g, 1.5 eq) in anh. DMF (150 mL), at r.t., under N$_2$, was added NaH 60%/oil (1.7 g, 1 eq) and the reaction mixture was stirred at r.t. for 20 min. A solution of ethyl 2,4-dichloro-6-methyl-3-pyridinecarboxylate (10 g, 42.9 mmol) was then added dropwise and the reaction mixture was stirred at 80° C. for 4 hr. It was then cooled down to r.t. and quenched with ice water. The addition of EtOAc caused a precipitate to form. The white solid was collected by filtration, washed with water and dried in vacuo (5.2 g). The filtrate was transferred into a separatory funnel and the aqueous layer was extracted with EtOAc (2×100 mL). The combined organic layers were washed with sat.aq. NaCl, dried over anh. Na$_2$SO$_4$, the solids were filtered and the solvent evaporated. The crude product was treated with EtOAc and left at r.t. overnight. The precipitate was filtrated, dried in vacuo and combined with the previous batch to give the title compound as a white solid (7.2 g, 48%).
NMR ($^1$H, DMSO-d$_6$): δ 8.53 (d, 1H), 7.77 (s, 1H), 7.18 (bs, 1H), 6.89 (d, 1H), 4.32 (q, 2H), 3.75 (t, 2H), 3.42 (t, 2H), 3.31 (s, 3H), 1.26 (t, 3H). MS (m/z): 350 [MH]$^+$.

Intermediate 39

1-{1-[2-Chloro-3-(hydroxymethyl)-6-methyl-4-pyridinyl]-1H-pyrazol-3-yl}-2-imidazolidinone To a suspension of intermediate 38 (7.2 g, 20.6 mmol) in anh. CH$_2$Cl$_2$ (120 mL), at 0° C., under N$_2$, was added dropwise DIBAl-H 1M/CH$_2$Cl$_2$, (41.2 mL, 2 eq). At the end of the addition the resulting solution was allowed to warm to r.t. and stirred for 2 hr. More DIBAl-H was added until the reaction was complete (3×20.5 mL), each time cooling at 0° C. and then stirring at r.t. for 1 hr. The reaction mixture was then cooled to 0° C., quenched by the slow addition of a Rochelle salt solution (50 mL) and stirred at r.t. overnight. The white lattice was treated with 4 L of Roschell's salt solution and 3 L of $CH_2Cl_2$ and stirred at r.t. for 20 hr. The two phases were separated and the aqueous layer was extracted with $CH_2Cl_2$ (5×500 mL). The combined organic extracts were washed with sat.aq. NaCl, dried over anh. $Na_2SO_4$, the solids were filtered and the solvent evaporated to give the title compound as a white solid (4 g, 63%).

NMR ($^1$H, DMSO-$d_6$): δ 8.36 (d, 1H), 7.49 (s, 1H), 7.12 (bs, 1H), 6.86 (d, 1H), 5.47 (t, 1H), 4.61 (d, 2H), 3.88 (t, 2H), 3.44 (t, 2H), 3.30 (s, 3H). MS (m/z): 308 [MH]$^+$.

Intermediate 40

1-{1-[2-Chloro-3-(hydroxymethyl)-6-methyl-4-pyridinyl]-1H-pyrazol-3-yl}-3-{[4-(methyloxy)phenyl]methyl}-2-imidazolidinone To a suspension of intermediate 39 (100 mg, 0.325 mmol) in anh. DMF (6.5 mL), at r.t., under $N_2$, was added NaH 60%/oil (13 mg, 1 eq.). The reaction mixture was stirred at r.t. until a pale yellow solution was obtained (circa 10 min). After cooling to 0° C., 1-(chloromethyl)-4-(methyloxy)benzene (44 μL, 1 eq) was added and the reaction mixture was stirred for 1.5 hr. It was partitioned between EtOAc/sat.aq. NaCl, the phases were separated and the organic layer was dried over anh. $Na_2SO_4$. The solids were filtered and the solvent evaporated. The crude product was purified by flash chromatography (silica gel, EtOAc/cHex 6:4→7:3) to give the title compound as a white solid (45.5 mg, 33%).

NMR ($^1$H, CDCl$_3$): δ 7.85 (d, 1H), 7.20 (dd, 2H), 7.15 (d, 1H), 7.10 (s, 1H), 6.89 (dd, 2H), 4.85 (s, 2H), 4.40 (s, 2H), 3.84 (t, 2H), 3.80 (s, 3H), 3.43 (t, 2H), 2.6 (s, 3H). MS (m/z): 428 [MH]$^+$, 450 [M+23]$^+$

Intermediate 41

2-Chloro-6-methyl-4-[3-(3-{[4-(methyloxy)phenyl]methyl}-2-oxo-1-imidazolidinyl)-1H-pyrazol-1-yl]-3-pyridinecarbaldehyde To a solution of intermediate 40 (925 mg, 2.16 mmol) in $CH_2Cl_2$ (90 mL), was added Dess Martin periodinane (1.38 g, 1.5 eq) in three portions and the reaction mixture was stirred at r.t. for 2 hr. More Dess Martin periodinane (750 mg, 0.2 eq) was added and the reaction mixture was stirred for an additional 30 min. $Na_2S_2O_3$ (5 eq) in a sat.aq. $NaHCO_3$ (100 mL) was added and the phases were separated. The aqueous layer was extracted with $CH_2Cl_2$ (3×50 mL) and the combined organic extracts were dried over anh. $Na_2SO_4$, the solids were filtered and the solvent evaporated. The crude product was purified by flash chromatography (silica gel, EtOAc/cHex 6:4→7:3) to give the title compound as a white solid (520 mg, 57%).

NMR ($^1$H, CDCl$_3$): δ 10.26 (s, 1H), 7.85 (d, 1H), 7.23 (dd, 2H), 7.20 (s, 1H), 7.13 (d, 1H), 6.89 (dd, 2H), 4.41 (s, 2H), 3.84 (t, 2H), 3.80 (s, 3H), 3.39 (t, 2H), 2.6 (s, 3H). MS (m/z): 426 [MH]$^+$.

Intermediate 42

1-(1-{2-Chloro-6-methyl-3-[(E)-2-(methyloxy)ethenyl]-4-pyridinyl}-1H-pyrazol-3-yl)-3-{[4-(methyloxy)phenyl]methyl}-2-imidazolidinone n-BuLi 1.6M/Hexane (0.44 mL, 3 eq) was added dropwise to a suspension of (methoxymethyl)-triphenylphosphonium chloride (224 mg, 3 eq) in THF (5 mL) at 0° C., under $N_2$. At the end of the addition the reaction mixture was allowed to warm to r.t. and stirred for 20 min. A solution of intermediate 41 (100 mg, 0.235 mmol) in THF (8 mL) was added and the reaction mixture stirred at r.t. for an additional 1.5 hr. The mixture was treated with water, EtOAc was added and the phases were separated. The organic layer was dried over anh. $Na_2SO_4$, the solids were filtered and the solvent evaporated in vacuo to a residue which was purified on an SCX cartridge (100% cHex→cHex/EtOAc 7:3) to give the title compound as a white solid (68 mg, 63%) as a 7:3 mixture of trans:cis isomers.

NMR ($^1$H, CDCl$_3$): δ 7.36 (d, 1H), 7.24 (m, 3H), 6.99 (d, 1H), 6.87 (d, 2H), 6.58 (d, 2H), 5.59 (d, 2H), 4.40 (s, 2H), 3.89 (m, 2H), 3.78 (s, 3H), 3.64 (s, 3H), 3.37 (m, 2H), 2.50 (s, 3H). MS (m/z): 454 [MH]$^+$.

Intermediate 43

{2-Chloro-6-methyl-4-[3-(3-{[4-(methyloxy)phenyl]methyl}-2-oxo-1-imidazolidinyl)-1H-pyrazol-1-yl]-3-pyridinyl}acetaldehyde To a solution of intermediate 42 (5.5 g, 12.5 mmol) in THF (120 mL), at r.t., was added 6.0M HCl (60 mL, 28.4 eq.) and the reaction mixture was stirred for 18 hr. The reaction mixture was quenched with sat.aq. $NaHCO_3$ until neutral pH, the solvent partially removed and the crude mixture partitioned between EtOAc/water. The phases were separated and the organic layer was washed with sat.aq. NaCl (2×10 mL). It was dried over anh. $Na_2SO_4$, the solids were filtered and the solvent evaporated. The crude product was purified by flash chromatography (silica gel, cHex/EtOAc 4:6) to give the title compound as a white solid (4.6 g, 86%).

NMR ($^1$H, CDCl$_3$): δ 9.73 (s, 1H), 7.70 (d, 1H), 7.23 (d, 2H), 7.06 (m, 2H), 6.88 (d, 2H), 4.40 (s, 2H), 4.01 (s, 2H), 3.80 (s, 3H), 3.76 (t, 2H), 3.37 (t, 2H), 2.58 (s, 3H). MS (m/z): 440 [MH]$^+$.

Intermediate 44

1-{1-[2-Chloro-3-(2-hydroxyethyl)-6-methyl-4-pyridinyl]-1H-pyrazol-3-yl}-3-{[4-(methyloxy)phenyl]methyl}-2-imidazolidinone To a solution of intermediate 43 (4.4 g, 9.96 mmol) in anh. MeOH (100 mL) at 0° C., under $N_2$, was added NaBH$_4$ (397 mg, 1.0 eq) in small portions and the reaction mixture was warmed up to r.t. and stirred for 30 min. The reaction mixture was quenched with water, the solvent partially removed and partitioned between EtOAc/water. The phases were separated and the organic layer was washed with sat.aq. NaCl (2×10 mL). It was dried over anh. $Na_2SO_4$, the solids were filtered and the solvent evaporated. The crude product was purified by flash chromatography (silica gel, cHex/EtOAc 1:1) to give the title compound as a white solid (4.26 g, 96%).

NMR ($^1$H, CDCl$_3$): δ 7.65 (d, 1H), 7.24 (d, 2H), 7.09 (d, 1H), 6.97 (s, 1H), 6.89 (d, 2H), 4.45 (s, 2H), 3.96 (m, 4H), 3.83 (s, 3H), 3.41 (t, 2H), 3.14 (t, 2H), 2.55 (s, 3H). MS (m/z): 442 [MH]$^+$.

Intermediate 45

1-{1-[2-Chloro-3-(2-{[(1,1-dimethylethyl)(dimethyl)silyl]oxy}ethyl)-6-methyl-4-pyridinyl]1H-pyrazol-3-yl}-3-{[4-(methyloxy)phenyl]methyl}-2-imidazolidinone To a solution of intermediate 44 (4.26 g, 7.66 mmol) in anh. DMF (100 mL), at 0° C., under $N_2$, were added imidazole (7.19 g, 11 eq), DMAP (122 mg, 0.1 eq), TBDMSCl (4.07 g, 2.8 eq) and the reaction mixture was warmed up to r.t. and stirred for 1 hr. It was then partitioned between EtOAc/sat.aq. NH₄Cl. The phases were separated and the organic layer was washed with sat.aq. NaCl (2×10 mL). It was dried over anh. Na₂SO₄, the solids were filtered and the solvent evaporated. The crude product was purified by flash chromatography (silica gel, cHex/EtOAc 7:3) to give the title compound as a yellow oil (4.92 g, 92%).

NMR ($^1$H, CDCl₃): δ 8.05 (d, 1H), 7.28 (d, 2H), 7.15 (s, 1H), 7.05 (d, 1H), 6.91 (d, 2H), 4.45 (s, 2H), 3.96 (m, 4H), 3.83 (s, 3H), 3.40 (t, 2H), 3.14 (t, 2H), 2.55 (s, 3H), 0.83 (s, 9H), 0.00 (s, 6H). MS (m/z): 556 [MH]$^+$.

Intermediate 46

1-{1-[3-(2-{[(1,1-Dimethylethyl)(dimethyl)silyl]oxy}ethyl)-6-methyl-2-({2-methyl-4-[(trifluoromethyl)oxy]phenyl}amino)-4-pyridinyl]-1H-pyrazol-3-yl}-3-{[4-(methyloxy)phenyl]methyl}-2-imidazolidinone To a solution of intermediate 45 (500 mg, 0.703 mmol) in anh. DME (10 mL), at r.t., under N₂, were added Pd₂(dba)₃ (82 mg, 0.1 eq), dicyclohexyl(2'-methyl-2-biphenylyl)phosphane (98 mg, 0.3 eq), K₃PO₄ (573 mg, 3 eq) and 2-methyl-4-[(trifluoromethyl)oxy]aniline (258 mg, 1.5 eq) and the reaction mixture was stirred and heated at reflux for 3 hr. It was then partitioned between EtOAc/sat.aq. NH₄Cl. The phases were separated and the organic layer was washed with sat.aq. NaCl (2×10 mL). It was dried over anh. Na₂SO₄, the solids were filtered and the solvent evaporated. The crude product was purified by flash chromatography (silica gel, cHex/EtOAc 7:3) to give the title compound as a white solid (555 mg, 86%).

NMR ($^1$H, CDCl₃): δ 7.97 (m 1H), 7.63 (m, 2H), 7.44 (m, 1H), 7.28 (d, 2H), 7.01 (m, 2H), 6.91 (m, 2H), 6.62 (s, 1H), 4.45 (s, 2H), 4.18 (t, 2H), 3.88 (t, 2H), 3.83 (s, 3H), 3.41 (t, 2H), 2.87 (t, 2H), 2.47 (s, 3H), 2.31 (s, 3H), 0.84 (s, 9H), 0.00 (s, 6H). MS (m/z): 711 [MH]$^+$.

Intermediate 47

1-{1-[3-(2-Hydroxyethyl)-6-methyl-2-({2-methyl-4-[(trifluoromethyl)oxy]phenyl}amino)-4-pyridinyl]-1H-pyrazol-3-yl}-3-{[4-(methyloxy)phenyl]methyl}-2-imidazolidinone To a solution of intermediate 46 (555 mg, 0.930 mmol) in anh. THF (5 mL), at r.t., under N₂, was added Et₃N.3HF (637 μL, 5 eq) and the reaction mixture was stirred at r.t. for 18 hr. It was then partitioned between EtOAc/water. The phases were separated and the organic layer was washed with sat.aq. NaCl (2×10 mL). It was dried over anh. Na₂SO₄, the solids were filtered and the solvent evaporated. The crude product was purified by flash chromatography (silica gel, cHex/EtOAc 1:1) to give the title compound as a white solid (281 mg, 60%).

NMR ($^1$H, CDCl₃): δ 7.92 (d, 1H), 7.61 (d, 1H), 7.35 (s, 1H), 7.25 (d, 2H), 7.01 (m, 2H), 6.89 (d, 2H), 6.58 (s, 1H), 4.41 (s, 2H), 4.14 (m, 2H), 3.86 (t, 2H), 3.80 (s, 3H), 3.38 (t, 2H), 2.88 (t, 2H), 2.44 (s, 3H), 2.28 (s, 3H). MS (m/z): 597 [MH]$^+$.

Intermediate 48

1-[1-(6-Methyl-1-{2-methyl-4-[(trifluoromethyl)oxy]phenyl}2,3-dihydro-1H-pyrrolo[2,3-b]pyridin-4-yl)-1H-pyrazol-3-yl]-3-{[4-(methyloxy)phenyl]methyl}-2-imidazolidinone To a solution of intermediate 47 (281 mg, 0.486 mmol) in CH₂Cl₂ (10 mL), under N₂, were added I₂ (240 mg, 2 eq), PPh₃ (247 mg, 2 eq) and Et₃N (131 μL, 2 eq) and the reaction mixture was stirred at r.t. for 2 hr. The solvent was then evaporated and the crude product was purified on an SCX cartridge (100% CH₂Cl₂→2.0M Et₃N in MeOH) and flash chromatography (silica gel, cHex/EtOAc 1:1) to give the title compound as a white solid (168 mg, 62%).

NMR ($^1$H, CDCl₃): δ 7.84 (d, 1H), 7.29 (d, 1H), 7.26 (d, 2H), 7.08 (m, 3H), 6.89 (d, 2H), 6.62 (s, 1H), 4.42 (s, 2H), 3.91 (m, 4H), 3.81 (s, 3H), 3.48 (t, 2H), 3.40 (t, 2H), 2.36 (s, 3H), 2.29 (s, 3H). MS (m/z): 579 [MH]$^+$.

Intermediate 49

4-({3-(2{[(1,1-Dimethylethyl)(dimethyl)silyl]oxy}ethyl)-6-methyl-4-[3-(3-{[4-(methyloxy)phenyl]methyl}-2-oxo-1-imidazolidinyl)-1H-pyrazol-1-yl]-2-pyridinyl}amino)-3-methylbenzonitrile As in intermediate 46, except that 4-amino-3-methylbenzonitrile was used instead of 2-methyl-4-[(trifluoromethyl)oxy]aniline.

NMR ($^1$H, CDCl₃): δ 8.21 (d, 1H), 7.89 (s, 1H), 7.6 (d, 1H), 7.42 (dd, 1H), 7.36 (bs, 1H), 7.23 (d, 2H), 6.99 (d, 1H), 6.87 (d, 2H), 6.71 (s, 1H), 4.41 (s, 2H), 4.19 (m, 2H), 4.04 (broad, 2H), 3.79 (s, 3H), 3.36 (t, 2H), 2.85 (t, 2H), 2.5 (s, 3H), 2.3 (s, 3H), 0.77 (s, 9H), −0.08 (s, 6H). MS (m/z): 652 [MH]$^+$.

Intermediate 50

4-({3-(2-Hydroxyethyl)-6-methyl-4-[3-(3-{[4-(methyloxy)phenyl]methyl}-2-oxo-1-imidazolidinyl)-1H-pyrazol-1-yl]-2-pyridinyl}amino)-3-methylbenzonitrile As in intermediate 47.

NMR ($^1$H, CDCl₃): δ 8.14 (d, 1H), 7.92 (s, 1H), 7.61 (d, 1H), 7.46 (dd, 1H), 7.4 (bs, 1H), 7.23 (d, 2H), 7.02 (d, 1H), 6.87 (d, 2H), 6.69 (s, 1H), 4.4 (s, 2H), 4.2 (m, 2H), 3.84 (t, 2H), 3.79 (s, 3H), 3.37 (t, 2H), 3.15 (bs, 1H), 2.86 (m, 2H), 2.48 (s, 3H), 2.28 (s, 3H). MS (m/z): 538 [MH]$^+$.

Intermediate 51

3-Methyl-4-{6-methyl-4-[3-(3-{[4-(methyloxy)phenyl]methyl}-2-oxo-1-imidazolidinyl)-1H-pyrazol-1-yl]-2,3-dihydro-1H-pyrrolo[2,3-b]pyridin-1-yl}benzonitrile As in intermediate 48.

NMR ($^1$H, CDCl₃): δ 7.83 (d, 1H), 7.54 (bs, 1H), 7.48 (dd, 1H), 7.35 (d, 1H), 7.23 (d, 2H), 7.02 (d, 1H), 6.87 (d, 2H), 6.67 (s, 1H), 4.41 (s, 2H), 3.94 (m, 4H), 3.79 (s, 3H), 3.48 (t, 2H), 3.38 (t, 2H), 2.34 (s, 3H), 2.29 (s, 3H). MS (m/z): 520 [MH]$^+$.

Intermediate 52

1-[1-(3-(2-{[(1,1-Dimethylethyl)(dimethyl)silyl]oxy}ethyl)-6-methyl-2-{[2-methyl-4-(1H-pyrazol-1-yl)phenyl]amino}-4-pyridinyl)-1H-pyrazol-3-yl]-3-{[4-(methyloxy)phenyl]methyl}-2-imidazolidinone As in intermediate 46, except that intermediate 83 (2-methyl-4-(1H-pyrazol-1-yl)aniline) was used instead of 2-methyl-4-[(trifluoromethyl)oxy]aniline.

NMR ($^1$H, CDCl₃): δ 8.07 (d, 1H), 7.88 (d, 1H), 7.70 (s, 1H), 7.57 (m, 3H), 7.46 (dd, 1H), 7.25 (d, 2H), 7.03 (d, 1H), 6.91 (d, 2H), 6.60 (s, 1H), 6.45 (t, 1H), 4.44 (s, 2H), 4.18 (t, 2H), 3.92 (t, 2H), 3.88 (s, 3H), 3.40 (s, 2H), 2.87 (t, 2H), 2.46 (s, 3H), 2.36 (s, 3), 0.84 (s, 9H), 0.00 (s, 6H). MS (m/z): 693 [MH]$^+$.

Intermediate 53

1-[1-(3-(2-Hydroxyethyl)-6-methyl-2-{[2-methyl-4-(1H-pyrazol-1-yl)phenyl]amino}-4-pyridinyl)-1H-pyrazol-3-yl]-3-{[4-(methyloxy)phenyl]methyl}-2-imidazolidinone As in intermediate 47.
NMR ($^1$H, CDCl$_3$): δ 7.94 (d, 1H), 7.81 (d, 1H), 7.65 (d, 1H), 7.57 (m, 2H), 7.48 (d, 1H), 7.38 (dd, 1H), 7.22 (d, 2H), 6.97 (d, 1H), 6.86 (d, 2H), 6.54 (s, 1H), 6.37 (t, 1H), 4.38 (t, 2H), 4.10 (m, 2H), 3.82 (t, 2H), 3.78 (s, 3H), 3.32 (t, 2H), 2.83 (t, 2H), 2.40 (s, 3H), 2.27 (s, 3H). MS (m/z): 579 [MH]$^+$.

Intermediate 54

1-(1-{6-Methyl-1-[2-methyl-4-(1H-pyrazol-1-yl)phenyl]-2,3-dihydro-1H-pyrrolo[2,3-b]pyridin-4-yl}-1H-pyrazol-3-yl)-3-{[4-(methyloxy)phenyl]methyl}-2-imidazolidinone As in intermediate 48.
NMR ($^1$H, CDCl$_3$): δ 7.90 (d, 1H), 7.85 (d, 1H), 7.71 (m, 1H), 7.67 (m, 1H), 7.63 (m, 1H), 7.36 (d, 1H), 7.24 (d, 2H), 7.03 (d, 1H), 6.90 (d, 2H), 6.62 (s, 1H), 6.45 (t, 1H), 4.43 (s, 2H), 3.96 (m, 4H), 3.81 (s, 3H), 3.49 (t, 2H), 3.40 (t, 2H), 2.34 (s, 3H), 2.29 (s, 6H). MS (m/z): 561 [MH]$^+$.

Intermediate 55

4-({3-(2-{[(1,1-Dimethylethyl)(dimethyl)silyl]oxy}ethyl)-6-methyl-4-[3-(3-{[4-methyloxy)phenyl]methyl}-2-oxo-1-imidazolidinyl)-1H-pyrazol-1-yl]-2-pyridinyl}amino)-3-(trifluoromethyl)benzonitrile As in intermediate 46, except that 4-amino-3-(trifluoromethyl)benzonitrile was used instead of 2-methyl-4-[(trifluoromethyl)oxy]aniline.
NMR ($^1$H, CDCl$_3$): δ 8.41 (d, 1H), 8.32 (s, 1H), 7.92 (d, 1H), 7.74 (m, 2H), 7.35 (m, 3H), 7.12 (d, 1H), 6.96 (d, 2H), 4.52 (s, 2H), 4.18 (t, 2H), 4.00 (m, 2H), 3.90 (s, 3H), 3.48 (t, 2H), 3.21 (t, 2H), 2.63 (s, 3H), 0.91 (s, 9H), 0.07 (s, 6H). MS (m/z): 706 [MH]$^+$.

Intermediate 56

4-({3-(2-Hydroxyethyl)-6-methyl-4-[3-(3-{[4-(methyloxy)phenyl]methyl}-2-oxo-1-imidazolidinyl)-1H-pyrazol-1-yl]-2-pyridinyl}amino)-3-(trifluoromethyl)benzonitrile As in intermediate 47.
NMR ($^1$H, CDCl$_3$): δ 8.28 (d, 1H), 8.20 (s, 1H), 7.77 (d, 1H), 7.61 (dd, 1H), 7.56 (d, 1H), 7.16 (d, 2H), 6.98 (d, 1H), 6.81 (d, 2H), 6.72 (s, 1H), 6.14 (t, 1H), 4.35 (s, 2H), 4.06 (t, 2H), 3.78 (t, 2H), 3.73 (s, 3H), 3.32 (t, 2H), 2.84 (t, 2H), 2.43 (s, 3H). MS (m/z): 592 [MH]$^+$.

Intermediate 57

4-{6-Methyl-4-[3-(3-{[4-(methyloxy)phenyl]methyl}-2-oxo-1-imidazolidinyl)-1H-pyrazol-1-yl]-2,3-dihydro-1H-pyrrolo[2,3-b]pyridin-1-yl}-3-(trifluoromethyl)benzonitrile As in intermediate 48.
NMR ($^1$H, CDCl$_3$): δ 8.00 (d, 1H), 7.85 (d, 1H), 7.81 (dd, 1H), 7.68 (d, 1H), 7.25 (d, 2H), 7.05 (d, 1H), 6.89 (d, 2H), 6.75 (s, 1H), 4.42 (s, 2H), 3.93 (m, 4H), 3.52 (t, 2H), 3.48 (s, 3H), 3.40 (t, 2H), 2.35 (s, 3H). MS (m/z): 574 [MH]$^+$.

Intermediate 58

1-{1-[2-{[2-(Difluoromethyl)-4-(methyloxy)phenyl]amino}-3-(2-{[(1,1-dimethylethyl)(dimethyl)silyl]oxy}ethyl)-6-methyl-4-pyridinyl]-1H-pyrazol-3-yl}-3-{[4-(methyloxy)phenyl]methyl}-2-imidazolidinone As in intermediate 46, except that intermediate 87 (2-(difluoromethyl)-4-(methyloxy)aniline) was used instead of 2-methyl-4-[(trifluoromethyl)oxy]aniline.
NMR ($^1$H, CDCl$_3$): δ 7.62 (d, 1H), 7.56 (d, 1H), 7.50 (s, 1H), 7.26 (d, 2H), 7.13 (d, 1H), 7.01-6.98 (m, 2H), 6.87-6.92 (m, 2H), 6.73 (t, 1H, J$_{(H-F)}$=56.1 Hz), 6.55 (s, 1H), 4.44 (s, 2H), 4.11 (t, 2H), 3.86 (t, 2H), 3.84 (s, 3H), 3.82 (s, 3H), 3.39 (t, 2H), 2.84 (t, 2H), 2.35 (s, 3H), 0.82 (s, 9H), 0.00 (s, 6H). MS (m/z): 693 [MH]$^+$.

Intermediate 59

1-{1-[2-{[2-(Difluoromethyl)-4-(methyloxy)phenyl]amino}-3-(2-hydroxyethyl)-6-methyl-4-pyridinyl]-1H-pyrazol-3-yl}-3-{[4-(methyloxy)phenyl]methyl}-2-imidazolidinone As in intermediate 47.
NMR ($^1$H, DMSO-d$_6$): δ 8.32 (bs, 1H), 8.02 (d, 1H), 7.34-7.30 (m, 1H), 7.21 (d, 2H), 7.05-7.07 (m, 2H), 6.9 (d, 2H), 6.86 (t, 1H, J$_{H-F}$=54.9 Hz), 6.76 (d, 1H), 6.63 (s, 1H), 5.29 (t, 1H), 4.31 (s, 2H), 3.73-3.84 (m, 10H), 3.34 (t, 2H), 2.77 (t, 2H), 2.19 (s, 3H). MS (m/z): 579 [MH]$^+$.

Intermediate 60

1-(1-{1-[2-(Difluoromethyl)-4-(methyloxy)phenyl]-6-methyl-2,3-dihydro-1H-pyrrolo[2,3-b]pyridin-4-yl}-1H-pyrazol-3-yl)-3-{[4-(methyloxy)phenyl]methyl}-2-imidazolidinone As in intermediate 48.
NMR ($^1$H, CDCl$_3$): δ 7.84 (d, 1H), 7.21-7.26 (m, 4H), 7.02-7.06 (m, 2H), 6.87-6.89 (m, 2H), 6.87 (t, 1H, J$_{(H-F)}$=55.5 Hz), 6.64 (s, 1H), 4.23 (s, 2H), 3.81-3.97 (m, 10H), 3.37-3.49 (m, 4H), 2.32 (s, 3H). MS (m/z): 561 [MH]$^+$.

Intermediate 61

4-({3-(2-{[(1,1-Dimethylethyl)(dimethyl)silyl]oxy}ethyl)-6-methyl-4-[3-(3-{[4-(methyloxy)phenyl]methyl}-2-oxo-1-imidazolidinyl)-1H-pyrazol-1-yl]-2-pyridinyl}amino)-3-[(trifluoromethyl)oxy]benzonitrile As in intermediate 46, except that 4-amino-3-[(trifluoromethyl)oxy]benzonitrile was used instead of 2-methyl-4-[(trifluoromethyl)oxy]aniline.
MS (m/z): 722 [MH]$^+$.

Intermediate 62

4-({3-(2-Hydroxyethyl)-6-methyl-4-[3-(3-{[4-(methyloxy)phenyl]methyl}-2-oxo-1-imidazolidinyl)-1H-pyrazol-1-yl]-2-pyridinyl}amino)-3-[(trifluoromethyl)oxy]benzonitrile As in intermediate 47.
NMR ($^1$H, CDCl$_3$): δ 8.84 (d, 1H), 8.56 (d, 1H), 7.61 (d, 1H), 7.5 (dd, 1H), 7.48 (bs, 1H), 7.23 (d, 2H), 7.02 (d, 1H), 6.87 (d, 2H), 6.87 (d, 2H), 6.74 (s, 1H), 4.4 (s, 2H), 4.2 (m, 2H), 3.84 (t, 2H), 3.79 (s, 3H), 3.37 (t, 2H), 3.1 (bs, 1H), 2.86 (m, 2H), 2.5 (s, 3H). MS (m/z): 608 [MH]$^+$.

Intermediate 63

4-{6-Methyl-4-[3-(3-{[4-(methyloxy)phenyl]methyl}-2-oxo-1-imidazolidinyl)-1H-pyrazol-1-yl]-2,3-dihydro-1H-pyrrolo[2,3-b]pyridin-1-yl}-3-[(trifluoromethyl)oxy]benzonitrile As in intermediate 48.
NMR ($^1$H, CDCl$_3$): δ 8.05 (d, 1H), 7.84 (m, 1H), 7.54 (bs, 1H), 7.5 (m, 1H), 7.23 (m, 1H), 7.03 (m, 1H), 6.87 (d, 2H), 6.78 (s, 1H), 4.41 (s, 2H), 4.11 (m, 2H), 3.91 (m, 2H), 3.79 (s, 3H), 3.5 (t, 2H), 3.38 (t, 2H), 2.41 (s, 3H). MS (m/z): 590 [MH]$^+$.

Intermediate 64

4-({3-(2-{[(1,1-Dimethylethyl)(dimethyl)silyl]oxy}ethyl)-6-methyl-4-[3-(3-{[4-(methyloxy)phenyl]methyl}-2-oxo-1-imidazolidinyl)-1H-pyrazol-1-yl]-2-pyridinyl}amino)-3-ethylbenzonitrile As in intermediate 46, except that 4-amino-3-ethylbenzonitrile was used instead of 2-methyl-4-[(trifluoromethyl)oxy]aniline.
MS (m/z): 666 [MH]$^+$.

Intermediate 65

3-Ethyl-4-({3-(2-hydroxyethyl)-6-methyl-4-[3-(3-{[4-(methyloxy)phenyl]methyl}-2-oxo-1-imidazolidinyl)-1H-pyrazol-1-yl]-2-pyridinyl}amino)benzonitrile As in intermediate 47.
NMR ($^1$H, CDCl$_3$): δ 8.11 (d, 1H), 7.92 (s, 1H), 7.61 (d, 1H), 7.43 (dd, 1H), 7.42 (bs, 1H), 7.23 (d, 2H), 7.01 (d, 1H), 6.87 (d, 2H), 6.69 (s, 1H), 4.41 (s, 2H), 4.19 (m, 2H), 3.84 (t, 2H), 3.79 (s, 3H), 3.37 (t, 2H), 3.2 (bs, 1H), 2.86 (m, 2H), 2.64 (m, 2H), 2.47 (s, 3H), 1.27 (t, 3H). MS (m/z): 552 [MH]$^+$.

Intermediate 66

3-Ethyl-4-{6-methyl-4-[3-(3-{[4-(methyloxy)phenyl]methyl}-2-oxo-1-imidazolidinyl)-1H-pyrazol-1-yl]-2,3-dihydro-1H-pyrrolo[2,3-b]pyridin-1-yl}benzonitrile As in intermediate 48.
NMR ($^1$H, CDCl$_3$): δ 7.83 (d, 1H), 7.6 (bs, 1H), 7.48 (dd, 1H), 7.35 (d, 1H), 7.23 (d, 2H), 7.02 (d, 1H), 6.87 (d, 2H), 6.65 (s, 1H), 4.41 (s, 2H), 3.92 (m, 4H), 3.79 (s, 3H), 3.48 (t, 2H), 3.38 (t, 2H), 2.66 (q, 2H), 2.32 (s, 3H), 1.22 (t, 3H). MS (m/z): 534 [MH]$^+$.

Intermediate 67

1-[1-(3-(2-{[(1,1-Dimethylethyl)(dimethyl)silyl]oxy}ethyl)-6-methyl-2-{[2-(methyloxy)-4-(1H-pyrazol-1-yl)phenyl]amino}-4-pyridinyl)-1H-pyrazol-3-yl]-3-{[4(methyloxy)phenyl]methyl}-2-imidazolidinone As in intermediate 46, except that intermediate 88 (2-(methyloxy)-4-(1H-pyrazol-1-yl)aniline) was used instead of 2-methyl-4-[(trifluoromethyl)oxy]aniline.
NMR ($^1$H, CDCl$_3$): δ 7.88 (d, 1H), 7.76 (d, 1H), 7.65 (d, 1H), 7.5 (bs, 1H), 7.35 (d, 1H), 7.21 (m, 3H), 7.16 (dd, 1H), 7.02 (d, 1H), 6.88 (d, 2H), 6.69 (d, 1H), 6.54 (s, 1H), 6.44 (t, 1H), 4.41 (s, 2H), 4.11 (t, 2H), 3.95 (s, 3H), 3.86 (t, 2H), 3.79 (s, 3H), 3.36 (t, 2H), 2.85 (t, 2H), 2.51 (s, 3H), 0.79 (s, 9H), 0.07 (s, 6H). MS (m/z): 709 [MH]$^+$ Intermediate 68

1-[1-(3-(2-Hydroxyethyl)-6-methyl-2-{[2-(methyloxy)-4-(1H-pyrazol-1-yl)phenyl]amino}-4-pyridinyl)-1H-pyrazol-3-yl]-3-{[4-(methyloxy)phenyl]methyl}-2-imidazolidinone As in intermediate 47.
NMR ($^1$H, CDCl$_3$): δ 8.66 (m, 1H), 7.88 (d, 1H), 7.69 (d, 1H), 7.62 (d, 1H), 7.5 (bs, 1H), 7.38 (d, 1H), 7.21 (m, 3H), 7.16 (dd, 1H), 7.02 (d, 1H), 6.88 (d, 2H), 6.54 (s, 1H), 6.44 (t, 1H), 4.41 (s, 2H), 4.11 (t, 2H), 3.98 (s, 3H), 3.9 (t, 2H), 3.79 (s, 3H), 3.40 (t, 2H), 2.9 (t, 2H), 2.49 (s, 3H). MS (m/z): 595 [MH]$^+$.

Intermediate 69

1-(1-{6-Methyl-1-[2-(methyloxy)-4-(1H-pyrazol-1-yl)phenyl]-2,3-dihydro-1H-pyrrolo[2,3-b]pyridin-4-yl}-1H-pyrazol-3-yl)-3-{[4-(methyloxy)phenyl]methyl}-2-imidazolidinone As in intermediate 48.
NMR ($^1$H, CDCl$_3$): δ 7.88 (d, 1H), 7.83 (d, 1H), 7.70 (d, 1H), 7.59 (d, 1H), 7.42 (d, 1H), 7.22 (m, 3H), 7.00 (d, 1H), 6.88 (d, 2H), 6.63 (s, 1H), 6.43 (t, 1H), 4.41 (s, 2H), 3.98 (m, 4H), 3.90 (s, 3H), 3.78 (s, 3H), 3.40 (m, 4H), 2.34 (s, 3H).

Intermediate 70

1-(1-{3-(2-{[(1,1-Dimethylethyl)(dimethyl)silyl]oxy}ethyl)-6-methyl-2-[(6-methyl-1,3-benzodioxol-5-yl)amino]-4-pyridinyl}-1H-pyrazol-3-yl)-3-{[4-(methyloxy)phenyl]methyl}-2-imidazolidinone As in intermediate 46, except that intermediate 89 (6-methyl-1,3-benzodioxol-5-amine) was used instead of 2-methyl-4-[(trifluoromethyl)oxy]aniline.
NMR ($^1$H, CDCl$_3$): δ 7.57 (d, 1H), 7.43 (bs, 1H), 7.25 (bs, 1H), 7.21 (d, 2H), 6.94 (d, 1H), 6.86 (d, 2H), 6.64 (d, 1H), 6.48 (bs, 1H), 5.88 (s, 2H), 4.40 (s, 2H), 4.08 (m, 2H), 3.83 (m, 2H), 3.79 (s, 3H), 3.35 (t, 2H), 2.78 (t, 2H), 2.38 (bs, 3H), 2.16 (s, 3H), 0.80 (s, 9H), −0.04 (s, 6H). MS (m/z): 671 [MH]$^+$.

Intermediate 71

1-(1-{3-(2-Hydroxyethyl)-6-methyl-2-[(6-methyl-1,3-benzodioxol-5-yl)amino]-4-pyridinyl}-1H-pyrazol-3-yl)-3-{[4-(methyloxy)phenyl]methyl}-2-imidazolidinone As in intermediate 47.
NMR ($^1$H, CDCl$_3$): δ 7.59 (d, 1H), 7.39 (bs, 1H), 7.24 (m, 2H), 7.21, 6.99 (d, 1H), 6.87 (d, 2H), 6.70 (bs, 1H), 6.65 (s, 1H), 6.48 (s, 1H), 5.89 (s, 2H), 4.40 (s, 2H), 4.33 (t, 1H), 4.08 (m, 2H), 3.85 (t, 2H), 3.78 (s, 3H), 3.36 (t, 2H), 2.85 (t, 2H), 2.38 (s, 3H), 2.17 (s, 3H). MS (m/z): 557 [MH]$^+$.

Intermediate 72

1-{1-[6-Methyl-1-(6-methyl-1,3-benzodioxol-5-yl)-2,3-dihydro-1H-pyrrolo[2,3-b]pyridin-4-yl]-1H-pyrazol-3-yl}-3-{[4-(methyloxy)phenyl]methyl}-2-imidazolidinone As in intermediate 48.
NMR ($^1$H, CDCl$_3$): δ 7.81 (d, 1H), 7.23 (m, 2H), 6.99 (d, 1H), 6.87 (d, 2H), 6.73 (d, 2H), 6.56 (s, 1H), 5.90 (s, 2H), 4.40

(s, 2H), 3.92 (t, 2H), 3.78 (m, 5H), 3.39 (m, 4H), 2.31 (s, 3H), 2.15 (s, 3H). MS (m/z): 539 [MH]⁺.

Intermediate 73

1-[1-(3-(2-{[(1,1-Dimethylethyl)(dimethyl)silyl]oxy}ethyl)-6-methyl-2-{[2,4,6-tris(methyloxy)phenyl]amino}-4-pyridinyl)-1H-pyrazol-3-yl]-3-{[4-(methyloxy)phenyl]methyl}-2-imidazolidinone As in intermediate 46, except that 2,4,6-tris(methyloxy) aniline was used instead of 2-methyl-4-[(trifluoromethyl)oxy]aniline.
MS (m/z): 703 [MH]⁺.

Intermediate 74

1-[1-(3-(2-Hydroxyethyl)-6-methyl-2-{[2,4,6-tris(methyloxy)phenyl]amino}-4-pyridinyl)-1H-pyrazol-3-yl]-3-{[4-(methyloxy)phenyl]methyl}-2-imidazolidinone As in intermediate 47.
MS (m/z): 589 [MH]⁺.

Intermediate 75

1-{[4-(Methyloxy)phenyl]methyl}-3-(1-{6-methyl-1-[2,4,6-tris(methyloxy)phenyl]-2,3-dihydro-1H-pyrrolo[2,3-b]pyridin-4-yl}-1H-pyrazol-3-yl)-2-imidazolidinone As in intermediate 48.
NMR (¹H, DMSO-d₆): δ 8.84 (d, 1H), 7.24 (bs, 2H), 7.01 (bs, 1H), 6.88-6.83 (d-d, 2H), 6.54 (s, 1H), 6.20 (d, 1H), 6.18 (s, 1H), 4.44 (s, 2H), 3.92-3.84 (m, 2H), 3.81-3.72 (m, 14H), 3.48-3.36 (m, 4H), 2.40 (bs, 3H). MS (m/z): 451 [MH]⁺.

Intermediate 76

1-(1-{3-(2-{[(1,1-Dimethylethyl)(dimethyl)silyl]oxy}ethyl)-6-methyl-2-[(4-methyl-1,3-benzodioxol-5-yl)amino]-4-pyridinyl}-1H-pyrazol-3-yl)-3-{[4-(methyloxy)phenyl]methyl}-2-imidazolidinone As in intermediate 46, except that 4-methyl-1,3-benzodioxol-5-amine (prepared as described in the U.S. Pat. No. 5,965,595 A) was used instead of 2-methyl-4-[(trifluoromethyl)oxy]aniline.
NMR (¹H, CDCl₃): δ 7.57 (d, 1H), 7.41 (bs, 1H), 7.21 (m, 3H), 7.00 (d, 1H), 6.95 (d, 2H), 6.87 (d, 1H), 6.47 (s, 1H), 5.92 (s, 2H), 4.40 (s, 2H), 4.11 (m, 2H), 3.83 (s, 3H), 3.35 (t, 2H), 2.79 (t, 2H), 2.33 (s, 3H), 2.04 (s, 3H), 0.79 (s, 9H), −0.04 (s, 6H). MS (m/z): 671 [MH]⁺.

Intermediate 77

1-(1-{3-(2-Hydroxyethyl)-6-methyl-2-[(6-methyl-1,3-benzodioxol-5-yl)amino]-4-pyridinyl}-1H-pyrazol-3-yl)-3-{[4-(methyloxy)phenyl]methyl}-2-imidazolidinone As in intermediate 47.
NMR (¹H, CDCl₃): δ 7.59 (d, 1H), 7.20 (m, 3H), 7.10 (d, 1H), 6.99 (d, 1H), 6.87 (d, 2H), 6.70 (d, 1H), 6.47 (s, 1H), 5.93 (s, 2H), 4.40 (s, 2H), 4.08 (m, 2H), 3.85 (t, 2H), 3.78 (s, 3H), 3.36 (t, 2H), 2.85 (t, 2H), 2.35 (s, 3H), 2.09 (s, 3H). MS (m/z): 557 [MH]⁺.

Intermediate 78

1-{1-[6-Methyl-1-(6-methyl-1,3-benzodioxol-5-yl)-2,3-dihydro-1H-pyrrolo[2,3-b]pyridin-4-yl]-1H-pyrazol-3-yl}-3-{[4-(methyloxy)phenyl]methyl}-2-imidazolidinone As in intermediate 48.
NMR (¹H, CDCl₃): δ 7.81 (d, 1H), 7.23 (m, 2H), 6.99 (d, 1H), 6.88 (d, 2H), 6.72 (dd, 2H), 6.56 (s, 1H), 5.95 (s, 2H), 4.40 (s, 2H), 3.92 (t, 2H), 3.81 (t, 2H), 3.78 (s, 3H), 3.39 (m, 4H), 2.31 (s, 3H), 2.08 (s, 3H). MS (m/z): 539 [MH]⁺

Intermediate 79

1-{1-[2-{[2,4-Bis(trifluoromethyl)phenyl]amino}-3-(2-{[(1,1-dimethylethyl)(dimethyl)silyl]oxy}ethyl)-6-methyl-4-pyridinyl]-1H-pyrazol-3-yl}-3-{[4-(methyloxy)phenyl]methyl}-2-imidazolidinone As in intermediate 46, except that 2,4-bis(trifluoromethyl) aniline was used instead of 2-methyl-4-[(trifluoromethyl)oxy]aniline.
NMR (¹H, CDCl₃): δ 8.33 (d, 1H), 7.99 (bs, 1H), 7.78 (bs, 1H), 7.63 (m, 2H), 7.24 (m, 2H), 6.99 (m, 1H) 6.85 (d, 2H), 6.77 (bs, 1H), 4.40 (s, 2H), 4.05 (m, 2H), 3.83 (m, 2H), 3.78 (s, 3H), 3.36 (t, 2H), 2.90 (t, 2H), 2.49 (s, 3H), 0.73 (s, 9H), −0.11 (s, 6H). MS (m/z): 749 [MH]⁺.

Intermediate 80

1-{1-[2-{[2,4-Bis(trifluoromethyl)phenyl]amino}-3-(2-hydroxyethyl)-6-methyl-4-pyridinyl]-1H-pyrazol-3-yl}-3-{[4-(methyloxy)phenyl]methyl}-2-imidazolidinone As in intermediate 47.
NMR (¹H, CDCl₃): δ 8.37 (d, 1H), 7.90 (bs, 1H), 7.79 (bs, 1H), 7.67 (m, 2H), 7.61 (d, 1H), 7.51 (m, 1H) 7.03 (bs, 1H), 6.88 (d, 2H), 6.72 (s, 1H), 4.40 (s, 2H), 4.20 (t, 2H), 4.05 (bs, 1H), 3.85 (t, 2H), 3.78 (s, 3H), 3.37 (t, 2H), 2.89 (t, 2H), 2.47 (s, 3H). MS (m/z): 635 [MH]⁺.

Intermediate 81

1-(1-{1-[2,4-Bis(trifluoromethyl)phenyl]-6-methyl-2,3-dihydro-1H-pyrrolo[2,3-b]pyridin-4-yl}-1H-pyrazol-3-yl)-3-{[4-(methyloxy)phenyl]methyl}-2-imidazolidinone As in intermediate 48.
NMR (¹H, CDCl₃): δ 7.96 (s, 1H), 7.84 (d, 1H), 7.79 (bs, 1H), 7.58 (d, 1H), 7.22 (d, 2H), 7.02 (d, 1H), 6.88 (d, 2H) 6.70 (s, 1H), 4.41 (s, 2H), 3.92 (m, 4H), 3.79 (s, 3H), 3.49 (t, 2H), 3.37 (t, 2H), 2.31 (s, 3H). MS (m/z): 617 [MH]⁺.

Intermediate 82

1,1-Dimethylethyl (4-bromo-2-methylphenyl)carbamate

To a solution of 4-bromo-2-methylaniline (1 g, 5.37 mmol,) in 1,4-dioxane (11 mL) and H₂O (4 mL), at r.t., were added Et₃N (2.7 mL, 1.2 eq) and BOC₂O (4.2 g, 1.2 eq). The reaction mixture was stirred at r.t. for 96 hr. Sat.aq. NH₄Cl and EtOAc (20 mL) were added and the phases were separated. The aqueous layer was further extracted with EtOAc (2×20 mL). The combined organic extracts were dried over anh. Na₂SO₄, the solids were filtered and the solvent evaporated. The residue was purified on an SCX cartridge (CH₂Cl₂, MeOH and NH$_3$(0.5 M in MeOH)) to give the title compound as a white solid (1.22 g, 79%).

NMR ($^1$H, DMSO-d$_6$): δ 8.55 (s, 1H), 7.35 (m, 1H), 7.28 (m, 2H), 2.17 (s, 3H), 1.44 (s, 9H). MS (m/z): 230 [MH–tBu]$^+$, 186 [MH–BOC]$^+$.

Intermediate 83

2-Methyl-4-(1H-pyrazol-1-yl)aniline

A solution of intermediate 82 (200 mg, 0.7 mmol), 1H-pyrazole (95 mg, 2 eq), CuI (133 mg, 1 eq), K$_2$CO$_3$ (290 mg, 2.1 eq) and (1R,2R)-diaminomethylcyclohexane (100 mg, 1 eq) in anh. NMP (1 mL), under N$_2$, was heated at 150° C. for 6 hr. It was cooled down to r.t. and poured into water. EtOAc was added and the phases were separated. The aqueous layer was further extracted with EtOAc (2×10 mL). The combined organic extracts were dried over anh. Na$_2$SO$_4$, the solids were filtered and the solvent evaporated. The residue was purified by flash-chromatography (silica gel, cHex/EtOAc 8:2) to give the title compound as a white solid (85.6 mg, 70%).

NMR ($^1$H, CDCl$_3$): δ 7.77 (dd, 1H), 7.66 (d, 1H), 7.39 (d, 1H), 7.29 (dd, 1H), 6.72 (d, 1H), 6.40 (t, 1H), 2.85 (bs, 1H). MS (m/z): 174 [MH]$^+$.

Intermediate 84

(5-Methoxy-2-nitro-phenyl)-methanol

To a suspension of cyanuric chloride (1.84 g, 1 eq) in anh. DME (60 mL) at r.t., under N$_2$, was added NMM (1.1 mL, 1 eq). The reaction mixture was stirred for 2 min and a precipitate was formed. A solution of 5-(methyloxy)-2-nitrobenzoic acid (2.0 g, 10 mmol) in anh. DME (20 mL) was added and the reaction mixture was stirred for 4 hr. The suspension was filtered and a solution of NaBH$_4$ (0.57 g, 1.5 eq) in water (30 mL) was added at 0° C. The reaction mixture was stirred for 20 min at 0° C. It was then diluted with Et$_2$O (10 mL) and acidified to pH 5 by addition of sat. aq. NH$_4$Cl. The phases were separated and the aqueous layer was extracted with Et$_2$O (2×100 mL). The combined organic extracts were washed with sat. aq. Na$_2$CO$_3$ and dried over anh. Na$_2$SO$_4$. The solids were filtered and the solvent evaporated to dryness. The crude product was purified by flash chromatography (silica gel, cHex/EtOAc 8:2) to give the title compound (958 mg, 53%).

NMR ($^1$H, CDCl$_3$): δ 8.15 (d, 1H), 7.19 (m, 1H), 6.85 (dd, 1H), 4.95 (d, 2H), 3.89 (s, 3H), 2.5 (t, 1H).

Intermediate 85

5-(Methyloxy)-2-nitrobenzaldehyde

To a solution of intermediate 84 (1:44 g, 7.9 mmol) in anh. CH$_2$Cl$_2$ (40 mL) at r.t., under N$_2$, was added Dess-Martin periodinane (3.68 g, 1.1 eq). The reaction mixture was stirred for 3 hr at r.t., then sat.aq. Na$_2$S$_2$O$_3$ (5 mL) and sat.aq. NaHCO$_3$ (20 mL) were added. The phases were separated and the aqueous layer was extracted with EtOAc (2×100 mL). The combined organic extracts were dried over anh. Na$_2$SO$_4$, the solids were filtered and the solvent evaporated to dryness to give 1.45 g (100%) of the title compound.

NMR ($^1$H, CDCl$_3$): δ 10.47 (s, 1H), 8.14 (d, 1H), 7.31 (d, 1H), 7.13 (dd, 1H), 3.94 (s, 3H).

Intermediate 86

2-(Difluoromethyl)-4-(methyloxy)-1-nitrobenzene

To a solution of intermediate 85 (250 mg, 1.38 mmol) in anh. CH$_2$Cl$_2$ (10 mL), at –78° C., under N$_2$, was added slowly DAST (2×0.4 mL, 2.2 eq). The reaction mixture was stirred at r.t. for 1.5 hr, after which was added sat.aq. NaCl. The phases were separated and the aqueous layer was extracted with EtOAc (3×20 mL). The combined organic extracts were dried over anh. Na$_2$SO$_4$, the solids were filtered and the solvent was evaporated to dryness. The crude product was purified by flash chromatography (silica gel, cHex/EtOAc 8:2) to give the title compound (176 mg, 63%) as a yellow oil.

NMR ($^1$H, CDCl$_3$): δ 8.21 (d, 1H), 7.43 (t, 1H, J$_{(H-F)}$=54.9 Hz), 7.33 (d, 1H), 7.06 (dd, 1H), 3.95 (s, 3H).

Intermediate 87

2-(Difluoromethyl)-4-(methyloxy)aniline

To a solution of intermediate 86 (176 mg, 0.87 mmol) in anh. MeOH (8.7 mL), at r.t., under N$_2$, was added Pd/C 10% (88 mg, 5% wt). The reaction mixture was placed under an atmosphere of H$_2$ for 5 hr. The catalyst was filtered off and the solution obtained was evaporated to dryness. The crude product was purified by flash chromatography (silica gel, cHex/EtOAc 9:1) to give the title compound (27 mg, 20%) as a yellow oil.

NMR ($^1$H, CDCl$_3$): δ 6.88-6.80 (m, 2H), 6.7-6.67 (m, 1H), 6.62 (t, 1H, J$_{(H-F)}$=55.6 Hz), 3.8-3.5 (bs, 2H), 3.76 (s, 3H) MS (m/z): 174 [MH]$^+$.

Intermediate 88

2-(Methyloxy)-4-(1H-pyrazol-1-yl)aniline

To a solution of 4-bromo-2-(methyloxy)aniline (400 mg, 1.979 mmol) in anh. NMP (4 mL), at r.t., under N$_2$, were added pyrazole (269 mg, 2 eq), K$_2$CO$_3$ (819 mg, 3 eq), CuI (377 mg, 1 eq) and (1R,2R)-diaminomethylcyclohexane (281 mg, 1 eq). The reaction mixture was stirred at 150° C. for 3 hr. It was cooled down to r.t. and poured into EtOAc/sat.aq. NaCl. The phases were separated and the organic layer was washed with sat.aq. NH$_4$Cl (20 mL) and sat.aq. NaCl (20 mL). The combined aqueous layers were extracted back with EtOAc (20 mL) and the combined organic extracts were dried over anh. Na$_2$SO$_4$. The solids were filtered and the solvent evaporated. The crude product was purified by flash chromatography (silica gel, cHex/EtOAc 7:3) to give the title compound as a brown oil (336 mg, 90%)

NMR ($^1$H, CDCl$_3$): δ 7.78 (d, 1H), 7.65 (d, 1H), 7.21 (d, 1H), 6.97 (dd, 1H), 6.73 (d, 1H), 6.40 (m, 1H), 4.05 (bs, 2H), 3.87 (s, 3H). MS (m/z): 190 [MH]$^+$.

Intermediate 89

6-Methyl-1,3-benzodioxol-5-amine

A mixture of 5-methyl-6-nitro-benzo(1,3)dioxole (50 mg, 0.28 mmol), Fe (54 mg, 3.5 eq) and ammonium chloride (51.2 mg, 3.5 eq) in a 1:1 mixture of MeOH/H$_2$O (2.8 mL) was subjected to microwave irradiation (60W, P=100 p.s.i.) at 80° C. for four 10 min periods. The brown solution was allowed to cool to r.t. and more Fe (3.5 eq) and ammonium chloride (3.5 eq) were added. The mixture was subjected to microwave irradiation (60W, P=100 p.s.i.) at 80° C. for an additional 10 min. Fe was filtered off and the solvent evaporated. The crude product was purified on an SCX cartridge (cHex/EtOAc 9:1) to give the title compound as a brown solid (40 mg, 93%).

NMR ($^1$H, CDCl$_3$): δ 6.54 (s, 1H), 6.27 (s, 1H), 5.80 (s, 2H), 2.27 (bs, 2H), 2.07 (s, 3H). MS (m/z): 152 [MH]$^+$.

Intermediate 90

4-{[2-Methyl-4-(methyloxy)phenyl]amino}butanenitrile

A solution of DIPEA (39 mL, 1 eq) and 4-methoxy-2-methylaniline (30 g, 0.22 mol) in anh. DMF (90 mL), under N₂, was heated at 100° C. 4-Bromobutanenitrile (21 mL, 1 eq) was added dropwise. The internal temperature was raised to 110° C. and the reaction mixture was stirred for 2 hr. The mixture was cooled down to r.t. and diluted with MTBE (240 mL). Water (270 mL) was added and the phases were separated. The organic layer was further washed with water (150 mL) and evaporated to 150 mL. Fresh MTBE (150 mL) was added and the mixture again evaporated to 150 mL. The mixture was treated with cHex (540 mL) over 20 min and the resulting suspension left at room temperature for 1.5 hr. The suspension was filtered and the cake washed with a mixture MTBE (30 mL)/cHex (90 mL). The title compound was collected as a violet solid (23.8 g, 53%).

NMR ($^1$H, DMSO-$d_6$): δ 6.65 (d, 1H), 6.63 (dd, 1H), 6.47 (d, 1H), 4.49 (bt, 1H), 3.64 (s, 3H), 3.10 (q, 2H), 2.59 (t, 2H), 2.09 (s, 3H), 1.86 (m, 2H). MS (m/z): 205 [MH]$^+$.

Intermediate 91

1-[2-Methyl-4-(methyloxy)phenyl]-2-pyrrolidinimine

To a suspension of intermediate 90 (35.0 g, 0.173 mol) in anh. IPA (280 mL), at r.t., under N₂, was added 6N HCl/IPA (51.45 mL, 1.5 eq). The mixture was heated to reflux for 4 hr, allowed to cool down to r.t. and evaporated to 140 mL. Water (350 mL) was added, the clear solution evaporated again to 140 mL and treated with 10% NaOH (140 mL). The mixture was extracted with CH₂Cl₂ (350 mL) and the organic layer further washed with 10% NaCl (140 mL). The organic layer was evaporated to dryness. The crude product was used as such in the next step (36.4 g, 100%)

NMR ($^1$H, DMSO-$d_6$): δ 7.09 (d, 1H), 6.87 (d, 1H), 6.80 (dd, 1H), 5.8-5.4 (b, 1H), 3.75 (s, 1H), 3.54 (t, 2H), 2.51 (t, 2H), 2.11 (s, 3H), 2.01 (m, 2H). MS (m/z): 205 [MH]$^+$.

Intermediate 92

4-Bromo-6-methyl-1-[2-methyl-4-(methyloxy)phenyl]-2,3-dihydro-1H-pyrrolo[2,3-b]pyridine To a solution of intermediate 4 (50.0 g, 0.15 mol) in anh. DMF (175 mL), at r.t., under N₂, was added CH₃SO₃H (58.1 mL, 1.2 eq) followed by NaBr (19.18 g, 1.5 eq) and the resulting mixture was heated at 85° C. for 2 hr. It was then diluted with MTBE (250 mL) and washed with 1N NaOH (250 mL). The aqueous phase was extracted with MTBE (150 mL) and the combined organic extracts washed twice with water (250 mL), then dried over anh. Na₂SO₄. The solids were filtered and the solvent evaporated to give the title compound (38 g, 76%) as a yellow solid.

NMR ($^1$H, DMSO-$d_6$): δ 7.17 (d, 1H), 6.87 (d, 1H), 6.80 (dd, 1H), 6.56 (s, 1H), 3.86 (t, 2H), 3.76 (s, 3H), 3.06 (t, 2H), 2.15-2.14 (2s, 6H). MS (m/z): 333/335 [MH]$^+$.

Intermediate 93

{6-Methyl-1-[2-methyl-4-(methyloxy)phenyl]-2,3-dihydro-1H-pyrrolo[2,3-b]pyridin-4-yl}boronic acid To a mixture of triisopropyl borate (185 µL, 3 eq) and intermediate 5 (100 mg, 1 eq) in an anh. 1:4 mixture of THF/toluene (0.5 mL), at −70° C., under N2, was added n-BuLi (329 µL, 2 eq) dropwise. The reaction mixture was stirred at −70° C. for 2.5 hr. It was warmed up to −20° C. and quenched with 1M HCl (0.5 mL, 2 eq). The mixture was warmed up to r.t. and precipitation of the boronic acid was observed. The solid was filtered and washed with CH₃CN. The title compound was obtained as a white solid (70 mg, 89%).

NMR ($^1$H, CDCl₃): δ 7.21 (d, 1H), 6.91 (d, 1H), 6.84 (dd, 1H), 6.61 (d, 1H), 4.02 (bt, 2H), 3.74 (s, 3H), 3.29 (bt, 2H), 2.21 (s, 3H), 2.15 (s, 3H). MS (m/z): 299 [MH]$^+$.

Intermediate 94

N-(6-Bromo-2-pyridinyl)-N'-(2-chloroethyl)urea

To a solution of 6-bromo-2-pyridinamine (1 g, 5.78 mmol) in anh. THF (25 mL), at r.t., under N₂, was added 1-chloro-2-isocyanatoethane (1.2 mL, 2.5 eq) and the reaction mixture was stirred at r.t. for 18 hr. The crude mixture was partitioned between CH₂Cl₂ and water. The phases were separated and the organic layer was dried over anh. Na₂SO₄. The solids were filtered and the solvent evaporated to give the title compound (1.06 g, 66%) which was used in the next step without further purification.

NMR ($^1$H, DMSO-$d_6$): δ 9.56 (bs, 1H), 7.75 (m, 2H), 7.32 (t, 1H), 7.14 (t, 1H), 3.65 (t, 2H), 3.46 (m, 2H)

Intermediate 95

1-(6-Bromo-2-pyridinyl)-2-imidazolidinone

To a solution of intermediate 94 (1.06 g, 3.82 mmol) in anh. THF (25 mL), at 0° C., under N₂, was added t-BuOK (644 mg, 1.5 eq) and the reaction mixture was allowed to warm up to r.t. After 1 h at r.t. the reaction mixture was partitioned between CH₂Cl₂ and water. The organic layer was dried over anh. Na₂SO₄, the solids were filtered and the solvent evaporated to give the title compound (0.988 g, quantitative) which was used in the next step without further purification.

NMR ($^1$H, DMSO-$d_6$): δ 8.14 (d, 1H), 7.61 (t, 1H), 7.33 (bs, 1H), 7.19 (d, 1H), 3.95 (t, 2H), 3.40 (t, 2H)

Intermediate 96

1-(6-Bromo-2-pyridinyl)-3-{[4-(methyloxy)phenyl]methyl}-2-imidazolidinone

To a solution of intermediate 95 (0.5 g, 2.06 mmol) in anh. DMF (25 mL), at r.t., under N₂, was added NaH 60%/oil (82 mg, 1 eq) and p-methoxybenzyl chloride (280 µL, 1 eq) and the mixture was stirred at r.t. for 2 hr. It was then partitioned between CH₂Cl₂ and water. The organic layer was dried over anh. Na₂SO₄, the solids were filtered and the solvent evaporated. The resulting crude product was purified by flash chromatography (silica gel, CH₂Cl₂/MeOH 9:1) to give the title compound (0.635 g, 85%).

NMR ($^1$H, CDCl₃): δ 8.33 (d, 1H), 7.71 (t, 1H), 7.29 (d, 2H), 7.10 (d, 1H), 6.85 (d, 2H), 4.43 (s, 2H), 4.00 (t, 2H), 3.83 (s, 3H), 3.55 (t, 2H)

Intermediate 97

1-(6-{6-Methyl-1-[2-methyl-4-(methyloxy)phenyl]-2,3-dihydro-1H-pyrrolo[2,3-b]pyridin-4-yl}-2-pyridinyl)-3-{[4-(methyloxy)phenyl]methyl}-2-imidazolidinone To a solution of intermediate 93 (50 mg, 1 eq) and intermediate 96 (121 mg, 2 eq) in a 1:1 mixture of toluene/EtOH (5 mL), at r.t., under N₂, were added 2M Na₂CO₃ (168 µL), Pd(PPh₃)₄ (19 mg, 0.1 eq) and tetra-n-butylammonium bromide (9 mg, 0.1 eq). The reaction mixture was stirred at 90° C. for 2 hr in a sealed vial. It was partitioned between EtOAc and water. The phases were separated and the organic layer was washed with sat.aq. NaCl. It was dried over anh. Na₂SO₄, the solids were filtered and the solvent evaporated. The crude product was purified by flash chromatography (silica gel, cHex/EtOAc 8:2) to give the title compound as a white solid (35 mg, 39%).

NMR ($^1$H, CDCl$_3$): δ 8.32 (d, 1H), 7.71 (d, 1H), 7.30-6.71 (m, 9H), 4.43 (s, 2H), 4.09 (t, 2H), 3.84-3.78 (m, 8H), 3.43-3.33 (m, 4H), 2.33 (s, 3H), 2.24 (s, 3H). MS (m/z): 536 [MH]$^+$.

Intermediate 98

N-{[3,4-Bis(methyloxy)phenyl]methyl}-N'-(2-chloroethyl)urea

To a solution of 3,4-dimethoxybenzylamine (2 g, 12 mmol) in anh. THF (25 mL), at r.t., under N$_2$, was added 2-chloroethyl isocyanate (1.02 mL, 1 eq). The reaction was complete after the addition. It was concentrated and the residue was purified by flash chromatography (silica gel, cHex/EtOAc 1:1→7:3 EtOAc/NH$_3$ (0.5 in MeOH)) to give the title compound as a white solid (2.9 g, 89%).

NMR ($^1$H, DMSO-d$_6$): δ 6.85 (d, 1H), 6.82 (d, 1H), 6.73 (dd, 1H), 6.41 (t, 1H), 6.16 (t, 1H), 4.10 (d, 2H), 3.70 (s, 3H), 3.69 (s, 3H), 3.56 (t, 2H), 3.31 (m, 2H). MS (m/z): 273 [MH]$^+$.

Intermediate 99

1-{[3,4-Bis(methyloxy)phenyl]methyl}-2-imidazolidinone

To a suspension of intermediate 98 (1 g, 3.68 mmol) in anh. THF (30 mL), at 0° C., under N$_2$, was added t-BuOK (500 mg, 1.2 eq). The ice bath was removed and the reaction mixture was stirred at r.t. for 1 hr. Sat.aq. NH$_4$Cl was added and the solvents were evaporated to dryness. The residue was purified by flash chromatography (silica gel, 100% EtOAc→EtOAc/MeOH 8:2) to give the title compound as a white solid (555 mg, 64%).

NMR ($^1$H, DMSO-d$_6$): δ 6.88 (d, 1H), 6.79 (d, 1H), 6.73 (dd, 1H), 6.33 (s, 1H), 4.12 (s, 2H), 3.70 (s, 6H), 3.16 (m, 4H). MS (m/z): 237 [MH]$^+$.

Intermediate 100

1-{[3,4-Bis(methyloxy)phenyl]methyl}-3-(4-chloro-2-pyrimidinyl)-2-imidazolidinone and intermediate 101 1-{[3,4-bis(methyloxy)phenyl]methyl}-3-(2-chloro-4-pyrimidinyl)-2-imidazolidinone To a solution of 2,4-dichloropyrimidine (600 mg, 2.54 mmol, 1 eq) and intermediate 99 (100 mg, 0.42 mmol) in anh. DMF (27 mL), at r.t., under N$_2$, was added NaH 60%/oil (112 mg, 1.1 eq). The reaction mixture was stirred at r.t. for 1 hr. Water and EtOAc were added and the two phases were separated. The aqueous layer was further extracted with EtOAc (3×20 mL). The combined organic extracts were concentrated and the residue was purified by flash chromatography (silica gel, cHex/EtOAc 7:3) to give intermediate 100 as a white solid (377 mg, 42%). The other regioisomer was collected in mixture with the unreacted intermediate 99. This crude mixture was repurified by flash chromatography (silica gel, CH$_2$Cl$_2$/NH$_3$(0.5 in MeOH) 95:5) to give intermediate 101 as a white solid (193.1 mg, 22%).

Intermediate 100

NMR ($^1$H, CDCl$_3$): δ 8.36 (d, 1H), 8.28 (d, 1H), 6.87 (s, 1H), 6.86 (d, 2H), 4.46 (s, 2H), 4.05 (dd, 2H), 3.91 (s, 6H), 3.43 (dd, 2H). MS (m/z): 349 [MH]$^+$.

Intermediate 101

NMR ($^1$H, DMSO): δ 8.55 (d, 1H), 7.19 (d, 1H), 6.88 (d, 1H), 6.83 (d, 1H), 6.78 (dd, 1H), 4.29 (s, 2H), 3.88 (dd, 2H), 3.70 (s, 3H), 3.69 (s, 3H), 3.28 (dd, 2H). MS (m/z): 349 [MH]$^+$.

Intermediate 102

1-{[3,4-Bis(methyloxy)phenyl]methyl}-3-(4-bromo-2-pyrimidinyl)-2-imidazolidinone To a suspension of intermediate 100 (50 mg, 0.144 mmol) in propionitrile (2 mL), at r.t., under N$_2$, was added TMSBr (38 μL, 2 eq). The reaction mixture was subjected to microwave irradiation (2×10 min, T=100° C.). 2N NaOH and EtOAc were added to the reaction mixture and the two phases were separated. The aqueous layer was further extracted with EtOAc (3×10 mL) and the combined organic extracts were concentrated in vacuo. The residue was purified on an SCX cartridge (100% CH$_2$Cl$_2$→NH$_3$ (0.5 in MeOH)) to give the title compound as a white solid (43 mg, 76%).

NMR ($^1$H, CDCl$_3$): δ 8.27 (m, 2H), 6.81-6.83 (m, 3H), 4.24 (s, 2H), 4.01 (t, 2H), 3.88 (s, 3H), 3.87 (s, 3H), 3.40 (t, 2H). MS (m/z): 393 [MH]$^+$.

Intermediate 103

1-{[3,4-Bis(methyloxy)phenyl]methyl}-3-(4-{6-methyl-1-[2-methyl-4-(methyloxy)phenyl]-2,3-dihydro-1H-pyrrolo[2,3-b]pyridin-4-yl}-2-pyrimidinyl)-2-imidazolidinone To a solution of intermediate 102 (43 mg, 0.112 mmol) and intermediate 93 (50 mg, 1.5 eq) in a 1:1 mixture of EtOH/toluene (4 mL), at r.t., under N$_2$, were added Pd(PPh$_3$)$_4$ (13 mg, 0.1 eq), tetra-n-butylammonium bromide (4 mg, 0.1 eq) and 2N Na$_2$CO$_3$ (1.6 ml, 28.5 eq). The reaction mixture was heated at 100° C. for 2 hr. It was cooled down to r.t. and poured into water. EtOAc was added and the phases were separated. The aqueous layer was further extracted with EtOAc (2×10 mL). The combined organic extracts were dried over anh. Na$_2$SO$_4$, the solids were filtered and the solvent evaporated. The residue was purified by flash chromatography (silica gel, cHex/EtOAc 9:1) to give the title compound as a yellow solid (71 mg, quantitative).

NMR ($^1$H, CDCl$_3$): δ 8.61 (dd, 1H), 8.24 (dd, 1H), 7.18-7.26 (m, 4H), 6.76-6.85 (m, 3H), 4.46 (s, 2H), 4.13 (t, 2H), 3.80-3.88 (m, 11H), 3.59 (t, 2H), 3.44 (t, 2H), 2.38 (s, 3H), 2.25 (s, 3H). MS (m/z): 567 [MH]$^+$.

Intermediate 104

1-{[3,4-Bis(methyloxy)phenyl]methyl}-3-(2-bromo-4-primidinyl)-2-imidazolidinone

To a suspension of intermediate 101 (188 mg, 0.54 mmol) in propionitrile (2 mL), at r.t., under N$_2$, was added TMSBr (143 μL, 2 eq). The reaction mixture was subjected to microwave irradiation (10 min, P=155 W, T=100° C., p=60 psi). 2N NaOH was added and the reaction mixture was concentrated in vacuo. The residue was purified on a MEGA Bond Elut silica cartridge (CH$_2$Cl$_2$/MeOH 95:5) to give the title compound as a yellow solid (33 mg, 16%).

NMR ($^1$H, DMSO-d$_6$): δ 8.44 (d, 1H), 7.35 (d, 1H), 6.80-6.90 (m, 3H), 4.31 (s, 2H), 3.90 (t, 2H), 3.73 (s, 3H), 3.72 (s, 3H), 3.22-3.34 (m, 2H). MS (m/z): 393 [MH]$^+$.

Intermediate 105

1-{[3,4-Bis(methyloxy)phenyl]methyl}-3-(2-{6-methyl-1-[2-methyl-4-(methyloxy)phenyl]-2,3-dihydro-1H-pyrrolo[2,3-b]pyridin-4-yl}-4-pyrimidinyl)-2-imidazolidinone To a solution of intermediate 104 (33 mg, 0.084 mmol) and intermediate 93 (37 mg, 1.5 eq) in a 1:1 mixture of EtOH/ toluene (3 mL) were added Pd(PPh$_3$)$_4$ (10 mg, 0.1 eq), tetra-n-butylammonium bromide (3 mg, 0.1 eq) and 2N Na$_2$CO$_3$ (1.2 mL, 28.5 eq). The reaction mixture was heated at 100° C. for 2.5 hr. It was cooled down to r.t. and poured into water. EtOAc was added and the phases were separated. The aqueous layer was further extracted with EtOAc (2×10 mL). The combined organic extracts were dried over anh. Na$_2$SO$_4$, the solids were filtered and the solvent evaporated. The residue was purified by flash chromatography (silica gel, CH$_2$Cl$_2$/MeOH 95:5) and on a Strata NH$_2$ deactivated silica cartridge (cHex/EtOAc 1:0→cHex/EtOAc 0:1) to give 13 mg of the title compound still contaminated by unidentified by-products. This crude mixture was used in the next step without further purification.

NMR ($^1$H, CDCl$_3$): δ 8.73 (d, 1H), 7.43-7.69 (m, 4H), 7.17 (d, 1H), 6.75-6.92 (m, 2H), 6.70 (s, 1H), 4.47 (s, 2H), 4.06-4.15 (m, 2H), 3.80-3.91 (m, 8H), 3.80 (s, 3H), 3.55-3.63 (m, 2H), 3.40 (m, 2H), 2.35 (s, 3H), 2.24 (s, 3H). MS (m/z): 567 [MH]$^+$.

Intermediate 106

1-{6-Methyl-1-[2-methyl-4-(methyloxy)phenyl]-2,3-dihydro-1H-pyrrolo[2,3-b]pyridin-4-yl}-1H-1,2,4-triazol-3-amine A suspension of intermediate 5 (50 mg, 0.13 mmol), 1H-1,2,4-triazol-3-amine (22 mg, 2 eq), CuI (145 mg, 6 eq), K$_2$CO$_3$ (37 mg, 2.1 eq) and 1-2-N,N'-dimethylcyclohexanediamine (106 mg, 6 eq) in anh. NMP (5 mL) at r.t., under N$_2$, was subjected to microwave irradiation (3×45 min, 150° C.). Sat.aq. NaCl (15 mL) was then added and the reaction mixture extracted with CH$_2$Cl$_2$ (2×15 mL). The combined organic extracts were dried over anh. Na$_2$SO$_4$, the solids were filtered and the solvents evaporated in vacuo The crude compound thus obtained was purified on an SCX cartridge (cHex/EtOAc 1:1→EtOAc/MeOH 9:1) to give the title compound as a white solid (20 mg, 46%).

NMR ($^1$H, CDCl$_3$): δ 8.7 (s, 1H), 7.2 (d, 1H), 6.8 (d, 1H), 6.7 (dd, 2H), 6.67 (s, 1H), 5.75 (bs, 2H), 3.75 (t, 2H), 3.7 (s, 3H), 3.4 (t, 2H), 2.2 (s, 3H), 2.2 (s, 3H). MS (m/z): 337 [MH]$^+$.

Intermediate 107

N-(2-Chloroethyl)-N'-(1-{6-methyl-1-[2-methyl-4-(methyloxy)phenyl]-2,3-dihydro-1H-pyrrolo[2,3-b]pyridin-4-yl}-1H-1,2,4-triazol-3-yl)urea To a solution of intermediate 106 (20 mg, 0.06 mmol) in anh. DMF (2 mL), at 0° C., under N$_2$, was added 3-chloroethyl isocyanate (0.5 mL, excess) and the reaction mixture was stirred at r.t. for 6 days. H$_2$O (15 mL) was then added and the mixture extracted with CH$_2$Cl$_2$ (2×15 mL). The combined organic extracts were dried over anh. Na$_2$SO$_4$, the solids were filtered and the solvents evaporated in vacuo. The crude product was purified on a MEGA Bond Elut silica cartridge (cHex/EtOAc 3:7→7:3) to give the title compound as a white solid (30 mg, 100%).

MS (m/z): 442 [MH]$^+$.

Intermediate 108

1-{1-[2-Chloro-3-(2-hydroxypropyl)-6-methyl-4-pyridinyl]-1H-pyrazol-3-yl}-3-{[4-(methyloxy)phenyl]methyl}-2-imidazolidinone To a clear solution of intermediate 43 (160 mg, 0.36 mmol) in anh THF (2 mL), cooled at 0° C., was added 3.0 M MeMgBr/Et$_2$O (0.18 mL, 1.5 eq). The reaction mixture was stirred at 0° C. for 1 h and then slowly warmed to r.t. After 1 h, the reaction was complete. EtOAc and sat.aq. NH$_4$Cl were added and the phases were separated. The organic layer was washed with sat.aq. NaCl and dried over anh. Na$_2$SO$_4$, the solids were filtered and the solvent evaporated. The crude product was purified by flash chromatography (silica gel, EtOAc/cHex 1:1→6:4) to give the title compound as a white solid (138 mg, 84%).

NMR ($^1$H, CDCl$_3$): δ 7.85 (bs, 1H), 7.65 (d, 1H), 7.21 (d, 2H), 7.1 (d, 1H), 6.88 (d, 2H), 4.45 (q, 1H), 4.3 (m, 1H), 3.9 (t, 2H), 3.7 (s, 3H), 3.4 (t, 2H), 2.95 (d, 2H), 2.5 (s, 3H), 1.25 (d, 3H). MS (m/z): 456 [MH]$^+$.

Intermediate 109

1-{1-[2-Chloro-3-(2-{[(1,1-dimethylethyl)(dimethyl)silyl]oxy}propyl)-6-methyl-4-pyridinyl]-1H-pyrazol-3-yl}-3-{[4-(methyloxy)phenyl]methyl}-2-imidazolidinone To a clear solution of intermediate 108 (135 mg, 0.3 mmol) in anh CH$_2$Cl$_2$ (2 mL), at 0° C., under N$_2$, were added 2,6-lutidine (77 μL, 2.2 eq) and tert-butyldimethylsilyl triflate (100 μL, 1.5 eq). The reaction mixture was stirred at r.t. for 4 hr. Sat.aq. NH$_4$Cl was added, the phases were separated and the organic layer was washed with sat.aq. NaCl and dried over anh. Na$_2$SO$_4$. The solids were filtered and the solvent evaporated. The crude product was purified by flash chromatography (silica gel, EtOAc/cHex 1:1) to give the title compound as a white solid (130 mg, 76%).

NMR ($^1$H, CDCl$_3$): δ 8.35 (bs, 1H), 7.19 (m, 3H), 7.00 (bs, 1H), 6.87 (d, 2H), 4.40 (s, 2H), 4.36 (m, 1H), 3.89 (m, 2H), 3.79 (s, 3H), 3.36 (t, 2H), 2.96 (m, 2H), 2.50 (s, 3H), 1.23 (d, 3H), 0.70 (s, 9H), −0.06 (s, 3H), −0.33 (s, 3H). MS (m/z): 570 [MH]$^+$.

Intermediate 110

1-[1-(3-(2-{[(1,1-Dimethylethyl)(dimethyl)silyl]oxy}propyl)-6-methyl-2-{[2-methyl-4-(methyloxy)phenyl]amino}-4-pyridinyl)-1H-pyrazol-3-yl]-3-{[4-(methyloxy)phenyl]methyl}-2-imidazolidinone To a mixture of intermediate 109 (130 mg, 0.227 mmol), Pd$_2$(DBA)$_3$ (20.8 mg, 10% mol), K$_3$PO$_4$ (145 mg, 3 eq), 2-(Dicyclohexylphosphino)-2'-methylbiphenyl (24.8 mg, 30% mol) and 4-methoxy-2-methylaniline (47 mg, 1.5 eq), at r.t., under N$_2$, was added anh. DME (2 mL). The reaction mixture was stirred at 90° C. for 3 hr. The mixture was cooled to r.t. and more Pd$_2$(DBA)$_3$ (20.8 mg, 10% mol) and 2-(Dicyclohexylphosphino)-2'-methylbiphenyl (24.8 mg, 30% mol) were added. The reaction was heated at 90° C. for an additional 2 hr and left overnight at r.t. After an addition of Pd$_2$(DBA)$_3$ (20.8 mg, 10% mol) and 2-(Dicyclohexylphosphino)-2'-methylbiphenyl (24.8 mg, 30% mol), the reaction mixture was heated for an additional 2 hr at 90° C. Then it was, cooled to r.t., treated with water and EtOAc, and the phases were separated. The organic layer was dried over anh. Na$_2$SO$_4$, the solids were filtered and the solvent concentrated in vacuo. The crude product was purified by flash chromatography (silica gel, cHex/EtOAc 8:2→7:3) to give the title compound as a yellow oil (84 mg), still contaminated with the unreacted aniline. The mixture was used in the next step without further purification.

MS (m/z): 671 [MH]$^+$.

Intermediate 111

1-[1-(3-(2-Hydroxypropyl)-6-methyl-2-{[2-methyl-4-(methyloxy)phenyl]amino}-4-pyridinyl)-1H-pyrazol-3-yl]-3-{[4-(methyloxy)phenyl]methyl}-2-imidazolidinone To a solution of intermediate 110 (80 mg, 0.12 mmol) in anh. THF (2.5 mL), at r.t., under N$_2$, was added Et$_3$N.3HF (156 μL, 8 eq) and the reaction mixture was stirred at r.t. for 18 hr. EtOAc and water were added, the phases were separated and the organic layer was dried over anh. Na$_2$SO$_4$. The solids were filtered and the solvent evaporated. The crude product was purified by flash chromatography (silica gel, cHex/EtOAc 1:1) to give the title compound as a pale yellow solid (23 mg, 18%, two steps).

($^1$H, CDCl$_3$): δ 7.63 (d, 1H), 7.57 (d, 1H), 7.21 (d, 2H), 7.00 (d, 1H), 6.87 (d, 2H), 6.74 (s, 1H), 6.72 (m, 2H), 6.44 (s, 1H), 4.74 (m, 1H), 4.40 (s, 2H), 4.35 (m, 1H), 3.87 (m, 2H), 3.78 (s, 3H), 3.77 (s, 3H), 3.36 (t, 2H), 2.81 (d, 1H), 2.78 (d, 1H), 2.34 (s, 3H), 2.22 (s, 3H), 1.33 (d, 3H). MS (m/z): 557 [MH]$^+$.

Intermediate 112

1-(1-{2,6-Dimethyl-1-[2-methyl-4-(methyloxy)phenyl]-2,3-dihydro-1H-pyrrolo[2,3-b]pyridin-4-yl}-1H-pyrazol-3-yl)-3-{[4-(methyloxy)phenyl]methyl}-2-imidazolidinone To a clear solution of intermediate 111 (23 mg, 0.04 mmol) in anh. CH$_2$Cl$_2$ (1 mL), at r.t., under N$_2$, were added Et$_3$N (10 μL, 2 eq), triphenylphosphine (21.7 mg, 2 eq) and I$_2$ (21 mg, 2 eq) and the reaction mixture was stirred at r.t. for 2 hr. CH$_2$Cl$_2$ and water were added, the phases were separated, the organic layer dried over anh. Na$_2$SO$_4$, the solids were filtered and the solvent evaporated. The crude product was purified by flash chromatography (cHex/EtOAc 1:1) to give the title compound as white solid (10 mg, 46%).

NMR ($^1$H, CDCl$_3$): δ 7.80 (d, 1H), 7.21 (d, 2H), 7.09 (d, 1H), 6.99 (d, 1H), 6.88 (d, 2H), 6.81 (d, 1H), 6.76 (dd, 1H), 6.53 (s, 1H), 4.41 (s, 2H), 4.35 (m, 1H), 3.91 (t, 2H), 3.79 (s, 6H), 3.63 (dd, 1H), 3.42 (t, 2H), 2.96 (dd, 1H), 2.28 (s, 3H), 2.17 (s, 3H), 1.18 (d, 3H). MS (m/z): 539 [MH]$^+$.

Intermediate 113

Methyl (4,6-dichloro-2-methyl-5-pyrimidinyl)acetate

Sodium (1.74 g, 3 eq) was added portionwise to anh. MeOH (60 mL), at 0° C., under N$_2$. After consumption of metallic sodium, acetamidine hydrochloride (7.06 g, 3 eq) was added. After 20 min. of stirring the precipitated NaCl was filtered off. A solution of 2-ethoxycarbonyl-succinic acid diethyl ester (6.04 g, 24.5 mmol) in anhydrous CH$_3$OH (20 mL) was added to the solution of free acetamidine and the mixture was stirred at r.t. for 2 days. The reaction mixture was concentrated to dryness in vacuo and the yellow foam (8.69 g) obtained was then mixed with POCl$_3$ (6 eq) and CH$_3$CN (80 mL) and heated at reflux for 18 hours. The resulting solution was cooled to r.t. and poured slowly into ice/water and conc. NH$_4$OH with vigorous stirring. The product was extracted with EtOAc (3×50 mL). The combined organic extracts were washed with brine, dried over anh. Na$_2$SO$_4$, filtered and concentrated in vacuo. The crude oil was purified by flash chromatography (silica gel, cHex/EtOAc 8:2). The title compound was obtained as a yellow solid (98% in two steps)

NMR ($^1$H, CDCl$_3$): δ 5.85 (m, 1H), 5.15 (dq, 1H), 5.11 (dq, 1H), 3.61 (dt, 2H), 2.67 (s, 3H). MS (m/z): 202 [M]$^+$ (2Cl).

Intermediate 114

2-(4,6-Dichloro-2-methyl-5-pyrimidinyl)ethanol

To a solution of intermediate 113 (4.0 g, 0.017 mol) in anh. THF (60 mL), at −78° C., under N$_2$, was added DIBAl-H 1M/THF (52.5 mL, 3 eq) dropwise. After the addition was complete, the reaction mixture was stirred at −30° C. for 3 hr. A Rochelle salt solution was then added at 0° C. and the phases were separated. The aqueous layer was extracted with EtOAc (2×50 mL) and the combined organic extracts were dried over anh. Na$_2$SO$_4$. The solids were filtered and the solvent evaporated. The title compound was obtained as a clear oil (3.1 gr, 89%) and was used in the next step without further purification.

NMR ($^1$H, CDCl$_3$): δ 4.90 (t, 2H), 3.15 (t, 2H), 2.64 (s, 3H), 1.70 (bs, 1H). MS (m/z): 207 [MH]$^+$

Intermediate 115

4,6-Dichloro-5-(2-{[(1,1-dimethylethyl)(dimethyl)silyl]oxy}ethyl)-2-methylpyrimidine To a solution of intermediate 114 (3.1 g, 0.015 mol) in anh. DMF (100 mL), at 0° C., under N$_2$, were added imidazole (17 g, 17 eq), t-butyldimethylsilyl chloride (6.35 gr, 2.8 eq) and DMAP (catalytic amount). The solution was stirred at r.t. for 18 hr. EtOAc (100 mL) and sat.aq. NH$_4$Cl (50 mL) were added and the phases were separated. The organic layer was washed with sat.aq. NaCl (2×100 mL) and dried over anh. Na$_2$SO$_4$. The solids were filtered and the solvent evaporated. The crude compound was purified by flash chromatography (silica gel, cHex/EtOAc 9:1) to give the title compound as a clear oil (4.6 g, 95%).

NMR ($^1$H, CDCl$_3$): δ 3.80 (t, 2H), 3.12 (t, 2H), 2.66 (s, 3H), 0.85 (s, 9H), 0.01 (s, 6H). MS (m/z): 321 [MH]$^+$

Intermediate 116

N-[2,4-Bis(trifluoromethyl)phenyl]-6-chloro-5-(2-{[(1,1-dimethylethyl)(dimethyl)-silyl]oxy}ethyl)-2-methyl-4-pyrimidinamine To absolution of 2,4-bis-trifluoromethyl-aniline (984 μL, 1 eq) in anh. DMF (15 mL), at 0° C., under N$_2$, was added NaH 80%/oil (400 mg, 2.2 eq). The reaction mixture was stirred at 0° C. for 30 min and was then added to a solution of intermediate 115 (2 g, 6 mmol) in anh. DMF (15 mL) at r.t., under N$_2$. The reaction mixture was stirred at r.t. for 30 min. The excess NaH was carefully destroyed with sat.aq. NaCl and the reaction mixture was diluted with EtOAc. The phases were separated, the organic layer was washed with sat.aq. NaCl (2×30 mL) and dried over anh. Na$_2$SO$_4$. The solids were filtered and the solvent evaporated. The crude compound was purified by flash chromatography (silica gel, cHex/EtOAc 95:5→90:10). The title compound was obtained as a clear oil (1.84 g, 56%).

NMR ($^1$H, CDCl$_3$): δ 8.61 (d, 1H), 8.04 (bs, 1H), 7.86 (s, 1H), 7.79 (d, 1H), 4.95 (t, 2H), 3.95 (t, 2H), 2.53 (s, 3H), 0.73 (s, 9H), −0.90 (s, 6H). MS (m/z): 514 [MH]$^+$

Intermediate 117

2-(4-{[2,4-Bis(trifluoromethyl)phenyl]amino}-6-chloro-2-methyl-5-pyrimidinyl)ethanol To a solution of intermediate 116 (1.84 g, 3.58 mmol) in anh. DMF (30 mL), at r.t., under N$_2$, was added Et$_3$N.3HF (2.4 mL, 3 eq). The reaction mixture was stirred at r.t. for 18 hr. It was then diluted with cold sat.aq. NaCl (50 mL) and extracted with EtOAc (3×50 mL). The combined organic extracts were dried over anh. Na$_2$SO$_4$. The solids were filtered and the solvent evaporated. The title compound was obtained as a clear oil (1.4 gr, 98%) and was used in the next step without further purification.

NMR ($^1$H, CDCl$_3$): δ 8.59 (bs, 1H), 8.22 (d, 1H), 7.84 (s, 1H), 7.75 (d, 1H), 4.06 (t, 2H), 3.01 (t, 2H), 2.50 (s, 3H) MS (m/z): 400 [MH]$^+$

Intermediate 118

7-[2,4-Bis(trifluoromethyl)phenyl]-4-chloro-2-methyl-6,7-dihydro-5H-pyrrolo[2,3-d]pyrimidine To a solution of intermediate 117 (514 mg, 1.29 mmol) in anh. CH$_2$Cl$_2$ (20 mL), at 0° C., under N$_2$, were added Et$_3$N (712 μL, 4 eq) and methanesulfonyl chloride (197 μL, 2 eq) and the reaction mixture was stirred at r.t. for 18 hr. Water (20 mL) was then added and the phases were separated. The aqueous layer was extracted with $CH_2Cl_2$ (2×20 mL) and the combined organic extracts were dried over anh. $Na_2SO_4$. The solids were filtered and the solvent evaporated. The crude product was purified by flash chromatography (silica gel, cHex/EtOAc 8:2) to give the title compound as a white solid (430 mg, 87%).

NMR ($^1$H, CDCl$_3$): δ 8.04 (s, 1H), 7.93 (s, 1H), 7.53 (d, 1H), 4.00 (t, 2H), 3.24 (t, 2H), 2.42 (s, 3H). MS (m/z): 381 [MH]$^+$.

Intermediate 119

2-{4-Chloro-6-[(2,4-dichlorophenyl)amino]-2-methyl-5-pyrimidinyl}ethanol

Intermediate 114 (1.34 g, 6.47 mmol) and 2,4-dichloroaniline (1.06 g, 1 eq) were heated in a sealed vial, at 100° C., under N$_2$, for 18 hr. A 1:1 mixture of H$_2$O/MeOH was added and a white precipitate was formed. The solids were filtered and dried to give the title compound as a white solid (960 mg, 44%).

MS (m/z): 332 [M]$^+$.

Intermediate 120

4-Chloro-7-(2,4-dichlorophenyl)-2-methyl-6,7-dihydro-5H-pyrrolo[2,3-d]pyrimidine To a solution of intermediate 119 (960 mg, 2.87 mmol) in anh. $CH_2Cl_2$ (10 mL), at 0° C., under N$_2$, were added Et$_3$N (1.21 mL, 3 eq) and MsCl (0.5 ml, 2.3 eq). The reaction mixture was kept at r.t. for 4 hr. Then Et$_3$N (0.6 mL, 2 eq) was added and the mixture was refluxed for 3 hr. The reaction mixture was diluted with $CH_2Cl_2$ and washed with 10% HCl (15 mL). The organic phases were separated and washed with sat.aq. NaCl. It was dried over anh. $Na_2SO_4$, the solids were filtered and the solvent evaporated. The title compound was obtained as a white solid (900 mg, quantitative yield) and was used as such in the next step without further purification.

NMR ($^1$H, CDCl$_3$): δ 7.45 (d, 1H), 7.3 (d, 2H), 4.05 (t, 2H), 3.16 (t, 2H), 2.45 (s, 3H). MS (m/z): 315 [MH]$^+$.

Intermediate 121

3-{6-Methyl-1-[2-methyl-4-(methyloxy)phenyl]-2,3-dihydro-1H-pyrrolo[2,3-b]pyridin-4-yl}aniline A suspension of intermediate 5 (100 mg, 0.263 mmol), 3-aminophenylboronic acid (61 mg, 1.5 eq), Pd(PPh$_3$)$_4$ (30 mg, 0.1 eq), TBAB (8 mg, 0.1 eq) and 2N Na$_2$CO$_3$ (3.7 ml, 28.5 eq), in a 1:1 mixture of anh. EtOH/Toluene (10 mL) was heated at 100° C. for 2.5 h. It was cooled down to r.t. and poured into water. EtOAc was added and the phases were separated. The aqueous layer was further extracted with EtOAc (2×10 mL). The combined organic extracts were dried over anh. Na$_2$SO$_4$, the solids were filtered and the solvent evaporated. The residue was purified on an SCX cartridge (100% $CH_2Cl_2$→NH$_3$ (0.5 in MeOH)) and on a MEGA Bond Elut silica cartridge ($CH_2Cl_2$/MeOH 95:5) to give the title compound as a white solid (91 mg, quantitative yield).

NMR ($^1$H, DMSO-d$_6$): δ 7.18 (d, 1H), 7.09 (t, 1H), 6.87 (d, 1H), 6.81 (dd, 1H), 6.76 (d, 1H), 6.69 (d, 2H), 6.61 (d, 2H), 6.41 (s, 1H), 5.18 (bs, 2H), 3.8 (m, 5H), 3.15 (t, 2H), 2.2 (s, 6H). MS (m/z): 346 [MH]$^+$.

Intermediate 122

N-(2-Chloroethyl)-N'-(3-{6-methyl-1-[2-methyl-4-(methyloxy)phenyl]-2,3-dihydro-1H-pyrrolo[2,3-b]pyridin-4-yl}phenyl)urea To a solution of intermediate 121 (91 mg, 0.26 mmol) in anh. THF (3 mL), at r.t., under N$_2$, was added 2-chloroethyl isocyanate (51 μL, 2 eq). The reaction mixture was stirred at r.t. for 2 hr. It was evaporated to dryness and the residue was purified by flash chromatography (silica gel, cHex/EtOAc 7:3→EtOAc/Et$_3$N 1:0.02) to give the title compound as a white solid (113.4 mg, 97%).

NMR ($^1$H, DMSO-d$_6$): δ 8.76 (s, 1H), 7.69 (s, 1H), 7.28 (m, 2H), 7.14 (d, 1H), 7.05 (t, 1H), 8.23 (d, 1H), 6.74 (dd, 1H), 6.4 (m, 2H), 3.75 (m, 5H), 3.6 (m, 2H), 3.4 (m, 2H), 3.1 (t, 2H), 2.15 (s, 3H), 2.15 (s, 3H). MS (m/z): 451 [MH]$^+$.

Intermediate 123

5-Methyl-1-{6-methyl-1-[2-methyl-4-(methyloxy)phenyl]-2,3-dihydro-1H-pyrrolo[2,3-b]pyridin-4-yl}-1H-pyrazol-3-amine A solution of intermediate 5 (200 mg, 0.52 mmol), 5-methyl-3-aminopyrazole (200 mg, 2 eq), CuI (285 mg, 3 eq), K$_2$CO$_3$ (150 mg, 2.1 eq), N-N'-dimethyltranscyclohexandiamine (213 mg, 3 eq) in anh. NMP (1 mL), was heated at 150° C. for 36 hr. H$_2$O (50 mL) was then added and the solution extracted with $CH_2Cl_2$ (3×25 mL). The organic layer was dried over anh. Na$_2$SO$_4$, the solids were filtered and the solvents evaporated in vacuo. The crude compound thus obtained was purified by flash chromatography (silica gel, cHex/EtOAc 9:1→3:7) to give the title compound as a white solid (60 mg, 33%).

NMR ($^1$H, CDCl$_3$): 7.15 (d, 1H); 6.85 (d, 1H); 6.75 (m, 1H); 6.45 (s, 1H); 5.48 (s, 1H); 4.74 (s, 2H); 3.71 (s, 3H); 3.23 (t, 2H); 3.12 (t, 2H); 2.20 (s, 3H), 2.11 (s, 6H) δ. MS (m/z): 350 [MH]$^+$.

Intermediate 124

N-(2-Chloroethyl)-N'-(1-{6-methyl-1-[2-methyl-4-(methyloxy)phenyl]-2,3-dihydro-1H-pyrrolo[2,3-b]pyridinyl-4-yl}-1H-1,2,4-triazol-3-yl)urea To a solution of intermediate 123 (60 mg, 0.17 mmol) in anh. DMF (2 mL), at 0° C., under N$_2$, was added 2-chloroethyl isocyanate (0.2 mL, excess) and the reaction mixture was stirred at r.t. for 16 hr. H$_2$O (10 mL) was then added and the solution extracted with $CH_2Cl_2$ (2×10 mL). The combined organic extracts was dried over anh. Na$_2$SO$_4$, the solids were filtered and the solvents evaporated in vacuo. The crude product was purified on an SCX cartridge ($CH_2Cl_2$, then 0.05 M NH$_3$/MeOH) to give the title compound as a white solid (30 mg, 40%).

MS (m/z): 455 [MH]$^+$.

Intermediate 125

1-Acetyl-3-[1-(1-{4-[(difluoromethyl)oxy]-2-methylphenyl}-6-methyl-2,3-dihydro-1H-pyrrolo[2,3-b]pyridin-4-yl)-1H-pyrazol-3-yl]-2-imidazolidinone To a solution of intermediate 29 (2.87 g, 4.63 mmols) in anh. DMF (80 mL), under N$_2$, at r.t., was added NaH 60%/oil (0.240 g, 1.2 eq). The reaction mixture was stirred at r.t. for 10 min, then the flask was sealed with a rubber septum. CF$_2$Br$_2$ (2.5 mL, 6 eq) was added and the mixture heated at 60° C. for 3 hr. The mixture was cooled down to r.t., quenched with sat.aq. NaHCO$_3$ and extracted with $CH_2Cl_2$ (1×50 mL). The organic layer was washed with sat.aq. NaCl and dried over anh. Na$_2$SO$_4$. The solids were filtered and the solvent evaporated. The residue was purified by flash chromatography twice (silica gel, 2.5% MeOH/$CH_2Cl_2$) to give 554 mg of a crude compound still contaminated by side products. It was re-purified by fraction lynx chromatography (M+H=483) and the resulting fractions (174 mg), still contaminated, were re-purified by flash chromatography (silica gel, 2% MeOH/CH₂Cl₂) to give the title compound (76 mg, 3.4%) as a white solid.

NMR (¹H, CDCl₃): δ 7.93 (d, 1H), 7.23 (dd, 1H), 7.1-7.0 (m, 3H), 6.63 (s, 1H), 6.54 (t, 1H), 4.07 (m, 4H), 4.03 (t, 2H), 3.53 (t, 2H), 2.63 (s, 3H), 2.40 (bs, 3H), 2.31 (s, 3H).

Example 1

Synthesis of compounds of general formula (II)

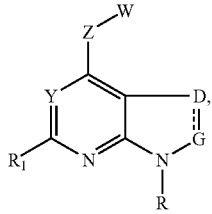

(II)

in which
Y is ═══CR₇;
W is a W2 derivative:

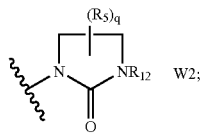

Z is a pyrazolyl, phenyl, pyridyl, pyrimidinyl, trazolyl, derivitive and

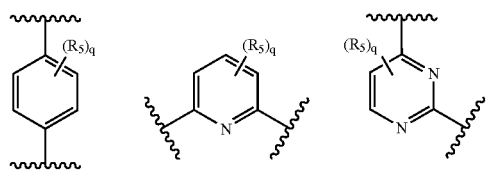

m is an integer from 0 to 2;
q is an integer from 0 to 4.

Example 1-1

1-{1-[1-(4-Methoxy-2-methylphenyl)-6-methyl-2,3-dihydro-1H-pyrrolo[2,3-b]pyridin-4-yl]-1H-pyrazol-3-yl}imidazolidin-2-one In a sealed vial, at r.t., under N₂, are mixed together intermediate 5 (60 mg, 0.158 mmol), CuI (6 mg, 0.2 eq) and K₂CO₃ (4.5 mg, 2.5 eq). A solution of dodecane (14.3 µL, 0.4 eq), trans-cyclohexanediamine (14 µL, 0.6 eq) and intermediate 8 (48 mg, 2 eq) in anh. NMP (5 mL) was added and the reaction mixture was stirred at 130° C. for 3.5 hr. It was then cooled down to r.t. and poured in EtOAc/H₂O. The phases were separated and the aqueous layer was extracted with EtOAc (2×10 mL). The combined organic extracts were dried over anh. Na₂SO₄, the solids were filtered and the solvent evaporated. The crude product was purified by flash chromatography (EtOAc/cHex 6:4, then 1:1, then 3:7) followed by an SCX cartridge (100% MeOH, then 2M NH₃/MeOH) to give the title compound as a white solid (34 mg, 53%).

Alternatively, to a suspension of CuI (8 mg, 0.02 eq) in anh. DMF (1.8 mL), at r.t., under N₂, was added (1R,2R)-N,N'-dimethyl-1,2-cyclohexanediamine (90 mg, 0.3 eq) and the blue solution obtained stirred at r.t. for 1.5 hr. Intermediate 8 (0.80 g, 2.5 eq) and K₂CO₃ (0.87 g, 3.0 eq) were added followed by intermediate 92 (0.7 g, 21 mmol) in anh. DMF (1.8 mL). The resulting mixture was heated at 125° C. for 30 hr. The mixture was cooled at 60° C. and water (10 mL) was added dropwise. The suspension was stirred at room temperature for 1 hr and the white precipitate was filtered and washed once with a 1:2 mixture of DMF/water (10 mL), then twice with water (10 mL). The collected solid was dried at 80° C. for 24 hr. The crude solid thus obtained was dissolved at r.t. in a 9:1 mixture of CH₂Cl₂/MeOH (10 mL). The solution was filtered through a carbon pad and the cake washed with the same solvent (10 mL). Heptane (20 mL) was added dropwise at r.t., the resulting suspension was left standing for 2 hr, filtered and washed with MeOH. The collected solid was dried at 80° C. for 24 hr to obtain the title compound (410 mg, 48%) as a white solid.

Example 1-2

1-{1-[1-(4-Methoxy-2-methylphenyl)-6-methyl-2,3-dihydro-1H-pyrrolo[2,3-b]pyridin-4-yl]-1H-pyrazol-3-yl}-3-methylimidazolidin-2-one To a solution of example 1 (20 mg, 0.05 mmol) in anh. THF (1 mL), at r.t., under N₂, was added KOt-Bu (5 mg, 1 eq) and the reaction mixture was stirred for 15 min. Methyl iodide (6 µL, 2 eq) was then added and the reaction mixture was stirred at r.t. for 3 hr. It was then poured into EtOAc/H₂O and the phases were separated. The aqueous layer was extracted with EtOAc (2×20 mL) and the combined organic extracts were dried over anh. Na₂SO₄. The solids were filtered and the solvent evaporated. The crude product was purified by flash chromatography (silica gel, cHex/EtOAc 1:1) to give the title compound as a yellow solid (6 mg, 29%).

Example 1-3

1-{1-[1-(2,4-Dichlorophenyl)-6-methyl-2,3-dihydro-1H-pyrrolo[2,3-b]pyridin-4-yl]-1H-pyrazol-3-yl}imidazolidin-2-one To a solution of intermediate 37 (25 mg, 0.062 mmol) and 1-(1H-pyrazol-3-yl)-2-imidazolidinone (18.8 mg, 2 eq) in anh. NMP (2 mL), at r.t., under N₂, were added K₂CO₃ (26 mg, 3 eq), CuI (1.2 mg, 0.1 eq) and (1R,2R)-diaminoethyl-cyclohexane (2.9 mg, 0.3 eq) and the reaction mixture was stirred at 100° C. for 1 hr, at 120° C. for 1 hr, at 150° C. for 1 hr and at 180° C. for 2 hr. The reaction mixture was then cooled to r.t., then partitioned between EtOAc/sat.aq. NaCl (100 mL/50 mL). The phases were separated and the organic layer was dried over anh. Na₂SO₄, the solids were filtered, the solvent evaporated and the crude product was purified by flash chromatography (silica gel, cHex/EtOAc 2:8) to give the title compound as a white solid (2 mg, 7%).

Example 1-4

1-(1-{1-[2,4-Bis(trifluoromethyl)phenyl]-6-methyl-2,3-dihydro-1H-pyrrolo[2,3-b]pyridin-4-yl}-1H-pyrazol-3-yl)-2-imidazolidinone To a solution of intermediate 81 (120 mg, 0.19 mmol) in TFA (12 mL), at r.t., under N₂, was added anisole (61 µL, 3 eq) and the reaction mixture was stirred at 80° C. for 2 hr. The solution was concentrated in vacuo. The residue was diluted with CH₂Cl₂ and washed with sat.aq. NaHCO₃. The organic layer was dried over anh. Na₂SO₄, the solids were filtered and the solvent evaporated. The crude product was purified by flash chromatography (CH$_2$Cl$_2$→CH$_2$Cl$_2$/MeOH 95:5) to give the title compound as a white solid (80 mg, 84%).

Example 1-5

1-{1-[1-(4-Hydroxy-2-methylphenyl)-6-methyl-2,3-dihydro-1H-pyrrolo[2,3-b]pyridin-4-yl]-1H-pyrazol-3-yl}-2-imidazolidinone To a solution of example 1 (131 mg, 0.324 mmol) in anh. CH$_2$Cl$_2$ (6.5 mL), at 0° C., under N$_2$, was added BBr$_3$ 1M/CH$_2$Cl$_2$ (1.6 mL, 5 eq) and the reaction mixture was stirred at 0° C. for 3 hr. MeOH (5 mL) was slowly added and the solvents were evaporated. The residue was taken up in CH$_2$Cl$_2$ and the organic layer was washed with sat.aq. NaHCO$_3$ (2×20 mL) and dried over anh. Na$_2$SO$_4$. The solids were filtered and the solvent evaporated. The crude compound was purified by flash chromatography (silica gel, 100% EtOAc→5% MeOH/EtOAc) to give the title compound as a yellow solid (65 mg, 51%).

Example 1-6

1-Acetyl-3-(1-{6-methyl-1-[2-methyl-4-(methyloxy)phenyl]-2,3-dihydro-1H-pyrrolo[2,3-b]pyridin-4-yl}-1H-pyrazol-3-yl)-2-imidazolidinone To a solution of example 1 (205 mg, 0.507 mmol) in anh. DMF (10 mL), at r.t., under N$_2$, was added NaH 60%/oil (24 mg, 1.2 eq). The reaction mixture was stirred at r.t. for 20 min. It was then cooled to 0° C. and acetyl chloride (72 µL, 2 eq) was added slowly. The reaction mixture was stirred at 0° C. for 15 min (a white precipitate formed) and at r.t. for 30 min. It was then poured into EtOAc/sat.aq. NaCl and the phases were separated. The organic layer was washed with sat.aq. NaCl (2×20 mL) and the combined aqueous phases extracted back with CH$_2$Cl$_2$ (2×20 mL). The combined organic extracts were dried over anh. Na$_2$SO$_4$, the solids were filtered and the solvent evaporated. The crude compound was purified by flash chromatography (silica gel, 2.5% MeOH/CH$_2$Cl$_2$). The title compound was obtained as a yellow solid (190 mg, 84%)

Example 1-7

1-(1-{1-[4-(Ethyloxy)-2-methylphenyl]-6-methyl-2,3-dihydro-1H-pyrrolo[2,3-b]pyridin-4-yl}-1H-pyrazol-3-yl)-2-imidazolidinone To a solution of intermediate 30 (5 mg, 0.011 mmol) in an anh. 3:1 mixture of MeOH/CH$_2$Cl$_2$ (1 mL), at r.t., under N$_2$, was added Cs$_2$CO$_3$ (18 mg, 5 eq) and the reaction mixture was stirred at r.t. for 1 hr. The solvent was evaporated and the residue purified by flash chromatography (MEGA-BondElut, 500 mg, cHex/EtOAc 1:1) to give the title compound (2.3 mg, 50%) as a white solid.

Example 1-8

1-[1-(6-Methyl-1-{2-methyl-4-[(1-methylethyl)oxy]phenyl}-2,3-dihydro-1H-pyrrolo[2,3-b]pyridin-4-yl)-1H-pyrazol-3-yl]-2-imidazolidinone To a solution of intermediate 31 (11 mg, 0.023 mmol) in an anh. 3:1 mixture of MeOH/CH$_2$Cl$_2$ (1 mL), at r.t., under N$_2$, was added Cs$_2$CO$_3$ (38 mg, 5 eq) and the reaction mixture was stirred at r.t. for 2 hr. The solvent was evaporated and the residue purified by flash chromatography (MEGA-BondElut, 1 gr, cHex/EtOAc 1:1) to give the title compound (2.1 mg, 21%) as a white solid.

Example 1-9

1-[1-(6-Methyl-1-{2-methyl-4-[(trifluoromethyl)oxy]phenyl}-2,3-dihydro-1H-pyrrolo[2,3-b]pyridin-4-yl)-1H-pyrazol-3-yl]-2-imidazolidinone To a solution of intermediate 48 (140 mg, 0.242 mmol) in TFA (3.0 mL), under N$_2$, was added anisole (263 µL, 10 eq) and the reaction mixture was stirred and heated at 80° C. for 2 hr. It was then cooled down to r.t., TFA was evaporated and the reaction mixture was partitioned between CH$_2$Cl$_2$/sat.aq. NaHCO$_3$. The phases were separated and the organic layer was washed with sat. aq. NaCl (2×10 mL). It was dried over anh. Na$_2$SO$_4$, the solids were filtered and the solvent evaporated. The crude product was purified by flash chromatography (silica gel, CH$_2$Cl$_2$/MeOH 95:5) to give the title compound as a white solid (110 mg, 99%).

Example 1-10

3-Methyl-4-{6-methyl-4-[3-(2-oxo-1-imidazolidinyl)-1H-pyrazol-1-yl]-2,3-dihydro-1H-pyrrolo[2,3-b]pyridin-1-yl}benzonitrile To a solution of intermediate 51 (120 mg, 0.23 mmol) in TFA (15 mL), at r.t., under N$_2$, was added anisole (75 µL, 3 eq) and the reaction mixture was stirred at 80° C. for 1.5 hr. The solution was concentrated in vacuo. The residue was diluted with CH$_2$Cl$_2$ and washed with a sat.aq. NaHCO$_3$. The organic layer was dried over anh. Na$_2$SO$_4$, the solids were filtered and the solvent evaporated. The crude product was purified on an SCX cartridge (CH$_2$Cl$_2$→CH$_2$Cl$_2$/MeOH 95:5) to give the title compound as a white solid (58 mg, 63%).

Example 1-11

1-(1-{6-Methyl-1-[2-methyl-4-(1H-pyrazol-1-yl)phenyl]-2,3-dihydro-1H-pyrrolo[2,3-b]pyridin-4-yl}-1H-pyrazol-3-yl)-2-imidazolidinone To a solution of intermediate 54 (95 mg, 0.169 mmol) in TFA (2.0 mL), under N$_2$, was added anisole (184 µL, 10 eq) and the reaction mixture was stirred and heated at 80° C. for 2 hr. It was then cooled down to r.t., TFA was evaporated and the reaction mixture was partitioned between CH$_2$Cl$_2$/sat.aq. NaHCO$_3$. The phases were separated and the organic layer was washed with sat.aq. NaCl (2×10 mL). It was dried over anh. Na$_2$SO$_4$, the solids were filtered and the solvent evaporated. The crude product was purified by flash chromatography (silica gel, CH$_2$Cl$_2$/MeOH 95:5) to give the title compound as a white solid (77 mg, 99%).

Example 1-12

4-{6-Methyl-4-[3-(2-oxo-1-imidazolidinyl)-1H-pyrazol-1-yl]-2,3-dihydro-1H-pyrrolo[2,3-b]pyridin-1-yl}-3-(trifluoromethyl)benzonitrile To a solution of intermediate 57 (70 mg, 0.122 mmol) in TFA (2.0 mL), under N$_2$, was added anisole (133 µL, 10 eq) and the reaction mixture was stirred and heated at 80° C. for 2 hr. It was then cooled down to r.t., TFA was evaporated and the crude product was directly purified on an SCX cartridge (100% CH$_2$Cl$_2$→CH$_2$Cl$_2$/MeOH and then 2.0M Et$_3$N/MeOH) to give the title compound as a white solid (55 mg, 99%).

Example 1-13

1-(1-{1-[2-(Difluoromethyl)-4-(methyloxy)phenyl]-6-methyl-2,3-dihydro-1H-pyrrolo[2,3-b]pyridin-4-yl}-1H-pyrazol-3-yl)-2-imidazolidinone To a solution of intermediate 60 (19.6 mg, 0.035 mmol) in TFA (4 mL), at r.t., under N$_2$, was added anisole (12 µL, 0.003 eq). The reaction mixture was stirred for 2 hr. Sat.aq.

NaHCO$_3$ was added until neutral pH and the mixture was evaporated to dryness. The residue was purified on an SCX cartridge (0.5M NH$_3$/MeOH) to give the title compound as a white foam (7.2 mg, 47%).

Example 1-14

4-{6-Methyl-4-[3-(2-oxo-1-imidazolidinyl)-1H-pyrazol-1-yl]-2,3-dihydro-1H-pyrrolo[2,3-b]pyridin-1-yl}-3-[(trifluoromethyl)oxy]benzonitrile To a solution of intermediate 63 (115 mg, 0.19 mmol) in TFA (12 mL), at r.t., under N$_2$, was added anisole (61 μL, 3 eq) and the reaction mixture was stirred at 80° C. for 1.5 hr. The solution was concentrated in vacuo. The residue was diluted with CH$_2$Cl$_2$ and washed with sat.aq. NaHCO$_3$. The organic layer was dried over anh. Na$_2$SO$_4$, the solids were filtered and the solvent evaporated. The crude product was purified on an SCX cartridge (CH$_2$Cl$_2$→CH$_2$Cl$_2$/MeOH 95:5) to give the title compound as a white solid (52.9 mg, 59%).

Example 1-15

3-Ethyl-4-{6-methyl-4-[3-(2-oxo-1-imidazolidinyl)-1H-pyrazol-1-yl]-2,3-dihydro-1H-pyrrolo[2,3-b]pyridin-1-yl}benzonitrile To a solution of intermediate 66 (70 mg, 0.13 mmol) in TFA (9 mL), at r.t., under N$_2$, was added anisole (42 μL, 3 eq) and the reaction mixture was stirred at 80° C. for 1 hr. The solution was concentrated in vacuo. The residue was diluted with CH$_2$Cl$_2$ and washed with sat.aq.NaHCO$_3$. The organic layer was dried over anh. Na$_2$SO$_4$, the solids were filtered and the solvent evaporated. The crude product was purified on an SCX cartridge (100% CH$_2$Cl$_2$→CH$_2$Cl$_2$/MeOH 95:5) to give the title compound as a white solid (29 mg, 54%).

Example 1-16

1-(1-{6-Methyl-1-[2-(methyloxy)-4-(1H-pyrazol-1-yl)phenyl]-2,3-dihydro-1H-pyrrolo[2,3-b]pyridin-4-yl}-1H-pyrazol-3-yl)-2-imidazolidinone To a solution of intermediate 69 (72 mg, 0.12 mmol) in TFA (7.5 mL), at r.t., under N$_2$, was added anisole (41 μL, 3 eq) and the reaction mixture was stirred at 80° C. for 1.5 hr. The solution was concentrated in vacuo. The residue was diluted with CH$_2$Cl$_2$ and washed with sat.aq. NaHCO$_3$. The organic layer was dried over anh. Na$_2$SO$_4$, the solids were filtered and the solvent evaporated. The crude product was purified on an SCX cartridge (CH$_2$Cl$_2$/0.5M NH3/MeOH 95:5) to give the title compound as a white solid (35 mg, 64%).

Example 1-17

1-{1-[6-Methyl-1-(6-methyl-1,3-benzodioxol-5-yl)-2,3-dihydro-1H-pyrrolo[2,3-b]pyridin-4-yl]-1H-pyrazol-3-yl}-2-imidazolidinone To a solution of intermediate 72 (41 mg, 0.076 mmol) in TFA (4.7 mL), at r.t., under N$_2$, was added anisole (25 μL, 3 eq) and the reaction mixture was stirred at 80° C. for 1.5 hr. The solution was concentrated in vacuo. The residue was diluted with CH$_2$Cl$_2$ and washed with sat.aq. NaHCO$_3$. The organic layer was dried over anh. Na$_2$SO$_4$, the solids were filtered and the solvent evaporated. The crude product was purified on an SCX cartridge (100% CH$_2$Cl$_2$→CH$_2$Cl$_2$/MeOH 98:2) to give the title compound as a white solid (25 mg, 79%).

Example 1-18

1-(1-{6-Methyl-1-[2,4,6-tris(methyloxy)phenyl]-2,3-dihydro-1H-pyrrolo[2,3-b]pyridin-4-yl}-1H-pyrazol-3-yl)-2-imidazolidinone To intermediate 75 (16 mg, 0.028 mmol) were added TFA (1 mL) and anisole (10 μL, 3 eq). The reaction mixture was stirred at r.t. for 3 hr, and the solvent was evaporated under reduced pressure. The crude mixture was partitioned between CH$_2$Cl$_2$/sat.aq. NaHCO$_3$. The phases were separated and the organic layer was dried over anh. Na$_2$SO$_4$, the solids were filtered and the solvent evaporated. The crude product was purified by flash chromatography (silica gel, 100% CH$_2$Cl$_2$→CH$_2$Cl$_2$/MeOH 97:3) followed by a further purification on an SCX SPE cartridge (100% CH$_2$Cl$_2$ to CH$_2$Cl$_2$/MeOH/2M NH$_3$ in MeOH 80:19:1) to give the title compound as a white solid (9.5 mg, 71%).

Example 1-19

1-{1-[6-Methyl-1-(6-methyl-1,3-benzodioxol-5-yl)-2,3-dihydro-1H-pyrrolo[2,3-b]pyridin-4-yl]-1H-pyrazol-3-yl}-2-imidazolidinone To a solution of intermediate 78 (20 mg, 0.037 mmol) in TFA (2.3 mL), at r.t., under N$_2$, was added anisole (12 μL, 3 eq.) and the reaction mixture was stirred at 80° C. for 2 hr. The solution was concentrated in vacuo. The residue was diluted with CH$_2$Cl$_2$ and washed with sat.aq. NaHCO$_3$. The organic layer was dried over anh. Na$_2$SO$_4$, the solids were filtered and the solvent evaporated. The crude product was purified on an SCX cartridge (CH$_2$Cl$_2$→CH$_2$Cl$_2$/MeOH 98:2) to give the title compound as a white solid (12.4 mg, 76%).

Example 1-20

1-(6-{6-Methyl-1-[2-methyl-4-(methyloxy)phenyl]-2,3-dihydro-1H-pyrrolo[2,3-b]pyridin-4-yl}-2-pyridinyl)-2-imidazolidinone To a solution of intermediate 97 (30 mg, 1 eq) in TFA (0.75 ml), at r.t., under N$_2$, were added Anisole (18.3 μL, 3 eq) and a drop of H$_2$SO$_4$. The reaction mixture was refluxed for 3 h. It was concentrated and then partitioned between EtOAc and NaHCO$_3$ss. The phases were separated and the organic layer was washed with sat.aq. NaCl. It was dried over anh. Na2SO4, the solids were filtered and the solvent evaporated. The compound was obtained as a white solid (22 mg, 98%).

Example 1-21

1-(4-{6-Methyl-1-[2-methyl-4-(methyloxy)phenyl]-2,3-dihydro-1H-pyrrolo[2,3-b]pyridin-4-yl}-2-pyrimidinyl)-2-imidazolidinone To a solution of intermediate 103 (71 mg, 0.125 mmol) in TFA (1 mL), at r.t., under N$_2$, was added anisole (50 μL, 3.7 eq). The reaction mixture was refluxed for 3 hr. No traces of the desired product were detected by MS analysis. To the cooled reaction mixture was added conc. H$_2$SO$_4$ (2 drops). The reaction mixture was refluxed for 75 min, cooled down to r.t. and neutralized with solid Na$_2$CO$_3$. The solvents were evaporated and the residue was purified on a MEGA Bond Elut silica cartridge (CH$_2$Cl$_2$/Et$_2$O/EtOAc 1:1:2→CH$_2$Cl$_2$/MeOH/Et$_3$N 1:1:0.02) to give the title compound as a yellow solid (24.2 mg, 47%).

Example 1-22

1-(2-{6-Methyl-1-[2-methyl-4-(methyloxy)phenyl]-2,3-dihydro-1H-pyrrolo[2,3-b]pyridin-4-yl}-4-pyrimidinyl)-2-imidazolidinone To a solution of intermediate 105 (13 mg, 0.023 mmol) in TFA (1 mL), at r.t., under $N_2$, was added anisole (10 μL, 4 eq) and conc. $H_2SO_4$ (2 drops). The reaction mixture was refluxed for 2 hr and neutralized with solid $NaHCO_3$. The reaction mixture was partitioned between EtOAc and water. The aqueous layer was further extracted with EtOAc (3×10 mL) and the combined organic extracts were concentrated in vacuo. The residue was purified by flash chromatography (silica gel, 100% $CH_2Cl_2$→$CH_2Cl_2$/MeOH 95:5) and on an SCX cartridge (100% $CH_2Cl_2$→$NH_3$ (0.5 in MeOH)) to give the title compound as a white solid (2.8 mg, 10%, 2 steps).

Example 1-23

1-(1-{6-Methyl-1-[2-methyl-4-(methyloxy)phenyl]-2,3-dihydro-1H-pyrrolo[2,3-b]pyridin-4-yl}-1H-pyrazol-3-yl)-2-imidazolidinone To a solution of intermediate 107 (30 mg, 0.06 mmol) in anh. THF (2 mL), at r.t., under $N_2$, was added KOt-Bu (9 mg, 1.2 eq) and the reaction mixture was stirred for 1 hr. Water (0.5 mL) was added and the solvent was evaporated. The aqueous phase was diluted with $H_2O$ and extracted with $CH_2Cl_2$ (3×20 mL). The combined organic extracts were dried over anh. $Na_2SO_4$. The solids were filtered and the solvent evaporated. The crude product was purified on a MEGA Bond Elut silica cartridge (100% EtOAc→EtOAc/MeOH 9:1) to give the title compound as a white solid (6 mg, 25%).

Example 1-24

1-(1-{2,6-Dimethyl-1-[2-methyl-4-(methyloxy)phenyl]-2,3-dihydro-1H-pyrrolo[2,3-b]pyridin-4-yl}-1H-pyrazol-3-yl)-2-imidazolidinone To a solution of intermediate 112 (10 mg, 0.018 mmol) in TFA (1.1 mL), at r.t., under $N_2$, was added anisole (10 μL, 5 eq) and the reaction mixture was stirred at 80° C. for 1.5 hr. The solution was then concentrated in vacuo. The residue was diluted with $CH_2Cl_2$, washed with sat.aq. $NaHCO_3$ and the phases were separated. The organic layer was dried over anh. $Na_2SO_4$, the solids were filtered and the solvent evaporated. The crude product was purified on a MEGA Bond Elut silica cartridge (100% $CH_2Cl_2$→$CH_2Cl_2$/MeOH 98:2) to give the title compound (racemate) as a white solid (6 mg, 80%).

Example 1-25

1-(3-{6-Methyl-1-[2-methyl-4-(methyloxy)phenyl]-2,3-dihydro-1H-pyrrolo[2,3-b]pyridin-4-yl}phenyl)-2-imidazolidinone To a suspension of intermediate 122 (60 mg, 0.13 mmol) in anh. THF (3 mL), at r.t., under $N_2$, was added t-BuOK (18 mg, 1.2 eq). The reaction mixture was stirred at r.t. for 3 hr. Sat.aq. $NH_4Cl$ and EtOAc were added and the phases were separated. The aqueous layer was further extracted with EtOAc (2×10 mL). The combined organic extracts were dried over anh. $Na_2SO_4$, the solids were filtered and the solvent evaporated. The residue was purified by flash chromatography (silica gel, cHex/EtOAc 8:2→100% EtOAc) to give the desired compound still contaminated with aliphatic impurities. This crude product was further purified by preparative HPLC (Column: X Terra MS C18 5 mm, 30×75 mm, Mobile phase: A: H2O+0.1% TFA, B: CH3CN+0.1% TFA, Gradient: 10% (B) for 1 min, from 10% (B) to 90% (B) in 12 min, Flow rate (ml/min): 43, UV wavelength range (nm): 200-400 Mass range (amu): 100-900, Ionization: ES+) to give the title compound as a white solid (31.3 mg, 58%).

Example 1-26

1-(5-Methyl-1-{6-methyl-1-[2-methyl-4-(methyloxy)phenyl]-2,3-dihydro-1H-pyrrolo[2,3-b]pyridin-4-yl}-1H-pyrazol-3-yl)-2-imidazolidinone To a solution of intermediate 124 (35 mg, 0.072 mmol) in anh. THF (2 mL), at r.t., under $N_2$, was added t-BuOK (9.8 mg, 1.2 eq) and the reaction mixture was stirred at r.t. for 18 hr. Water (0.5 mL) was added and the solvent was evaporated. The aqueous phase was diluted with $H_2O$ and extracted with $CH_2Cl_2$ (3×10 mL). The combined organic extracts were dried over anh. $Na_2SO_4$. The solids were filtered and the solvent evaporated. The crude product was purified on a MEGA Bond Elut silica cartridge (EtOAc/cHex 2:8→3:7) to give the title compound as a white solid (12 mg, 39%).

Example 1-27

1-[1-(1-{4-[(difluoromethyl)oxy]-2-methylphenyl}-6-methyl-2,3-dihydro-1H-pyrrolo[2,3-b]pyridin-4-yl)-1H-pyrazol-3-yl]-2-imidazolidinone To a suspension of intermediate 125 (76 mg, 0.156 mmol) in a 3:1 mixture of MeOH/$CH_2Cl_2$ (10 mL), at r.t., was added $CsCO_3$ (0.257 g, 5 eq). The mixture was stirred at r.t. for 1 hr. The solvent was evaporated and the residue purified by flash chromatography (silica gel, 2% MeOH/$CH_2Cl_2$) to give the title compound (45 mg, 71%) as white solid.

All the analytical data are set forth in the following Table 1-1 and in which:

| Cpd. No. | R | $R_{12}$ | Z | Analytical Data |
|---|---|---|---|---|
| 1-1 | 2-methyl-4-methoxy-phenyl | H | 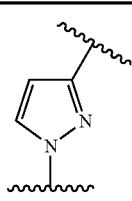 | NMR ($^1$H, CDCl$_3$): δ 8.29(d, 1H), 7.15(d, 1H), 7.04(s, 1H), 6.85(d, 1H), 6.79-6.74(m, 3H), 3.91(t, 2H), 3.82(t, 2H), 3.75 (s, 3H), 3.44(t, 4H), 2.17(s, 3H), 2.15(s, 3H) Structure confirmed by NOE experiment MS(m/z): 405[MH]$^+$ |

-continued

| Cpd. No. | R | R₁₂ | Z | Analytical Data |
|---|---|---|---|---|
| 1-2 | 2-methyl-4-methoxy-phenyl | CH₃ | 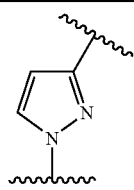 | NMR (¹H, CDCl₃): δ 7.76(d, 1H), 7.15(d, 1H), 6.93(d, 1H), 6.77(d, 1H), 6.75(dd, 1H), 6.52(s, 1H), 3.96(t, 2H), 3.84(t, 2H), 3.77(s, 3H), 3.50(t, 2H), 3.42(t, 2H), 3.89(s, 3H), 2.28(s, 3H), 2.20(s, 3H) MS(m/z): 419[MH]⁺ |
| 1-3 | 2,4-dichloro-phenyl | H | 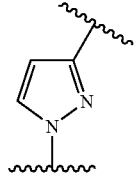 | NMR (¹H, CDCl₃): δ 7.82δ (s, 1H), 7.44(s, 1H), 7.42(s, 1H), 7.26(s, 1H), 6.95(s, 1H), 6.66(s, 1H), 4.57(bs, 1H), 4.09(t, 1H), 3.96(t, 1H), 3.61(t, 1H), 3.48(t, 1H), 2.34(s, 3H). Structure confirmed by NOE experiment MS(m/z): 429[M]⁺ |
| 1-4 | 2,4-bis-trifluoromethyl-phenyl | H | 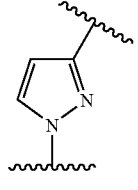 | NMR (¹H, CDCl₃): δ 7.96(s, 1H), 7.83(d, 1H), 7.80(bs, 1H), 7.61(d, 1H), 6.97(d, 1H), 6.70(s, 1H), 4.66(bs, 1H), 4.08(t, 2H), 3.91(t, 2H), 3.61(t, 2H), 3.50(t, 2H), 2.31(s, 3H). MS(m/z): 497[MH]⁺ |
| 1-5 | 2-methyl-4-hydroxy-phenyl | H | 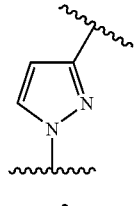 | NMR (¹H, DMSO-d₆): δ 9.31 (bs, 1H), 8.31(d, 1H), 7.07(bs, 1H), 7.04(d, 1H), 6.78(d, 1H), 6.75(s, 1H), 6.68(d, 1H), 6.62(dd, 1H), 3.93(t, 2H), 3.81(t, 2H), 3.46(m, 4H), 3.18(s, 3H), 2.10(s, 3H). MS(m/z): 391[MH]⁺. |
| 1-6 | 2-methyl-4-methoxy-phenyl | Ac | 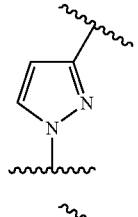 | NMR (¹H, CDCl₃): δ 7.85(d, 1H), 7.15(d, 1H), 6.95(d, 1H), 6.80(d, 1H), 6.75(dd, 1H), 6.55(s, 1H), 4.00(m, 4H), 3.85(t, 2H), 3.80(s, 3H), 3.45(t, 2H), 2.60(s, 3H), 2.30(s, 3H), 2.20(s, 3H). MS(m/z): 447[MH]⁺. |
| 1-7 | 2-methyl-4-ethoxy-phenyl | H | 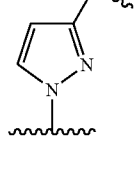 | NMR (¹H,): δ 7.82(d, 1H), 7.15(d, 1H), 6.90(d, 1H), 6.78(d, 1H), 6.75(dd, 1H), 6.70(dd, 1H), 4.70(bs, 1H), 4.2-4.0(m, 4H), 3.80(t, 2H), 3.60(t, 2H), 3.40(t, 2H), 2.30(s, 3H), 2.25(s, 2H), 1.45(t, 3H). Structure confirmed by NOE experiment MS(m/z): 419[MH]⁺. |
| 1-8 | 2-methyl-4-isopropoxy-phenyl | H | 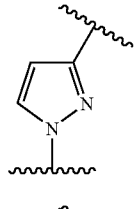 | NMR (¹H,): δ 7.90(d, 1H), 7.10(d, 1H), 6.90(d, 1H), 6.8-6.7(m, 2H), 6.55(s, 1H), 4.60(bs, 1H), 4.50(m, 1H), 4.10(t, 2H), 3.90(t, 2H), 3.60(t, 2H), 3.45(t, 2H), 2.30(s, 3H), 2.20(s, 3H), 1.26(d, 6H). MS(m/z): 475[MH]⁺. |
| 1-9 | 2-methyl-4-trifluoromethyloxy-phenyl | H | 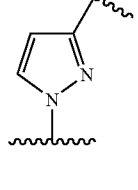 | NMR (¹H, CDCl₃): δ 7.84(d, 1H), 7.30(d, 1H), 7.12(s, 1H), 7.09(d, 1H), 6.98(d, 1H), 6.63(s, 1H), 4.68(s, 1H), 4.10(t, 2H), 3.91(t, 2H), 3.63(t, 2H), 3.50(t, 2H), 2.36(s, 3H), 2.29(s, 3H). MS(m/z): 459[MH]⁺. |

-continued

| Cpd. No. | R | R$_{12}$ | Z | Analytical Data |
|---|---|---|---|---|
| 1-10 | 2-methyl-4-cyano-phenyl | H | 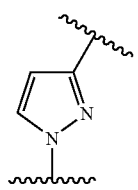 | NMR ($^1$H, CDCl$_3$): δ 7.82(d, 1H), 7.54(bs, 1H), 7.48(dd, 1H), 7.36(d, 1H), 6.96(d, 1H), 6.67(s, 1H), 4.55(bs, 1H), 4.11 (t, 2H), 3.95(t, 2H), 3.62(t, 2H), 3.49(t, 2H), 2.34(s, 3H), 2.29 (s, 3H).<br>MS(m/z): 400[MH]$^+$. |
| 1-11 | 2-methyl-4-(pyrazol-1-yl)-phenyl | H | 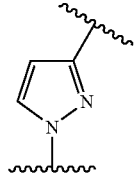 | NMR ($^1$H, CDCl$_3$): δ 7.90(d, 1H), 7.84(d, 1H), 7.72(d, 1H), 7.68(m, 1H), 7.64(m, 1H), 7.37(d, 1H), 6.97(d, 1H), 6.62 (s, 1H), 6.45(t, 1H), 4.77(s, 1H), 4.11(t, 2H), 3.94(t, 2H), 3.63(t, 2H), 3.50(t, 2H), 2.34 (s, 6H).<br>MS(m/z): 441[MH]$^+$. |
| 1-12 | 2-trifluoromethyl-4-cyano-phenyl | H | 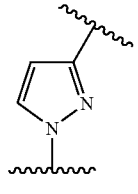 | NMR ($^1$H, CDCl$_3$): δ 8.01(d, 1H), 7.85(d, 1H), 7.84(dd, 1H), 7.69(d, 1H), 7.00(d, 1H), 6.75 (s, 1H), 4.65(s, 1H), 4.10(t, 2H), 3.98(t, 2H), 3.64(t, 2H), 3.51(t, 2H), 2.36(s, 3H).<br>MS(m/z): 454[MH]$^+$. |
| 1-13 | 2-difluoromethyl-4-methoxy | H | 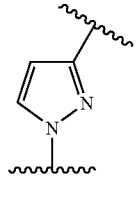 | NMR ($^1$H, CDCl$_3$): δ 7.84(d, 1H), 7.21(m, 2H), 7.02(dd, 1H), 6.87(t, 1H, J$_{(H-F)}$=57 Hz), 6.97(d, 1H), 6.64(s, 1H), 4.84 (bs, 1H), 4.13(t, 2H), 3.93(t, 2H), 3.9(s, 3H), 3.66(t, 2H), 3.53(t, 2H), 2.33(s, 3H).<br>MS(m/z): 441[MH]$^+$. |
| 1-14 | 2-trifluoromethyloxy-4-cyano-phenyl | H | 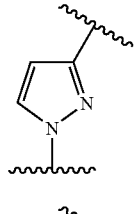 | NMR ($^1$H, CDCl$_3$): δ 8.05(d, 1H), 7.84(m, 1H), 7.54(bs, 1H), 7.5(m, 1H), 6.98(m, 1H), 678(s, 1H), 4.63(bs, 1H), 4.11 (m, 4H), 3.62(t, 2H), 3.48(t, 2H), 2.41(s, 3H).<br>MS(m/z): 470[MH]$^+$. |
| 1-15 | 2-ethyl-4-cyano-phenyl | H | 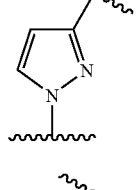 | NMR ($^1$H, CDCl$_3$): δ 7.82(d, 1H), 7.6(bs, 1H), 7.49(m, 1H), 7.34(m, 1H), 6.96(d, 1H), 6.65 (s, 1H), 4.7(bs, 1H), 4.11(t, 2H), 3.92(t, 2H), 3.62(t, 2H), 3.49(t, 2H), 2.66(m, 2H), 2.41 (s, 3H), 1.22(t, 3H).<br>MS(m/z): 414[MH]$^+$. |
| 1-16 | 2-methoxy-4-(pyrazol-1-yl)-phenyl | H | 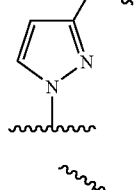 | NMR ($^1$H, CDCl$_3$): δ 7.89(d, 1H), 7.82(d, 1H), 7.69(d, 1H), 7.58(d, 1H), 7.42(d, 1H), 7.16 (dd, 1H), 6.94(d, 1H), 6.62(s, 1H), 6.44(t, 1H), 4.68(bs, 1H), 4.13-3.66(t/t, 4H), 3.89(s, 3H), 3.93-3.53(t/t, 4H), 2.34(s, 3H).<br>MS(m/z): 457[MH]$^+$. |
| 1-17 | 2-methyl-4,5-benzodioxolyl | H | 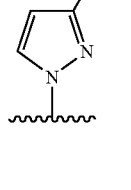 | NMR ($^1$H, CDCl$_3$): δ 7.8(d, 1H), 6.95(d, 1H), 6.8(s/s, 2H), 6.5 (s, 1H), 5.95(s, 2H), 4.5(bs, 1H), 4.1-3.5(t/t, 4H), 3.8-3.6 (t/t, 4H), 2.2(s, 3H), 2.1(s, 3H).<br>MS(m/z): 419[MH]$^+$. |

-continued

| Cpd. No. | R | $R_{12}$ | Z | Analytical Data |
|---|---|---|---|---|
| 1-18 | 2,4,6-trimethoxy-phenyl | H | pyrazol-3-yl (N1-linked) | NMR ($^1$H, CDCl$_3$): δ 8.26 (bs, 1H), 7.04(bs, 1H), 6.76 (bs, 1H), 6.65(bs, 1H), 6.29 (bs, 1H), 3.92-3.46(t, t, 4H), 3.81-3.46(t, t, 4H), 3.79(s, 3H), 3.69(s, 6H), 2.13(s, 3H). MS(m/z): 451[MH]$^+$. |
| 1-19 | 2-methyl-3,4-benzodioxolyl | H | pyrazol-3-yl (N1-linked) | NMR ($^1$H, CDCl$_3$): δ 7.81(d, 1H), 6.94(d, 1H), 6.75(dd, 2H), 6.56(s, 1H), 5.95(s, 2H), 4.61 (bs, 1H), 4.09(t, 2H), 3.84(t, 2H), 3.60(t, 2H), 3.43(t, 2H), 2.31(s, 3H), 2.08(s, 3H). MS(m/z): 419[MH]$^+$. |
| 1-20 | 2-methyl-4-methoxy-phenyl | H | 2-oxo-pyrrolidin-1-yl | NMR ($^1$H, CDCl$_3$): 8.15(d, 1H), 7.77(t, 1H), 7.42(d, 1H), 7.14 (d, 1H), 6.86(d, 1H), 6.8(m, 1H), 6.79(s, 1H), 4.22(t, 2H), 3.84(t, 2H), 3.78(s, 3H), 3.51 (m, 4H), 2.26(s, 3H), 2.21(s, 3H)δ. MS(m/z): 416[MH]$^+$. |
| 1-21 | 2-methyl-4-methoxy-phenyl | H | pyrimidin-2,4-diyl | NMR ($^1$H, DMSO-d$_6$): δ 8.62(d, 1H), 8.1(d, 1H), 7.65(bs, 1H), 7.21(s, 1H), 7.18(d, 1H), 6.86 (d, 1H), 6.79(d, 1H), 4.13(t, 2H), 3.85(t, 2H), 3.75(s, 3H), 3.57(t, 2H), 3.47(t, 2H), 2.21 (s, 3H), 2.16(s, 3H). Structure confirmed by NOE experiment MS(m/z): 417[MH]$^+$. |
| 1-22 | 2-methyl-4-methoxy-phenyl | H | pyrimidin-2,4-diyl | NMR ($^1$H, CDCl$_3$): δ 8.77(d, 1H), 7.29(d, 1H), 7.2(d, 1H), 6.83(d, 1H), 6.76(dd, 1H), 6.71(s, 1H), 4.95(bs, 1H), 4.28 (t, 2H), 3.93(t, 2H), 3.81(s, 3H), 3.61(t, 2H), 3.58(t, 2H), 2.37(s, 3H), 2.25(s, 3H). Structure confirmed by NOE experiment MS(m/z): 417[MH]$^+$. |
| 1-23 | 2-methyl-4-methoxy-phenyl | H | 1,2,4-triazol-3-yl (N1-linked) | NMR ($^1$H, CDCl$_3$): δ 8.98(s, 1H), 7.14(d, 1H), 7.05(s, 1H), 6.83(d, 1H), 6.76(m, 2H), 3.89 (t, 2H), 3.37(t, 2H), 3.82(t, 2H), 3.41(t, 2H), 3.71(s, 3H), 2.17(s, 3H), 2.11(s, 3H). Structure confirmed by NOE experiment MS(m/z): 406[MH]$^+$. |
| 1-24 | 2-methyl-4-methoxy-phenyl | H | pyrazol-3-yl (N1-linked) | NMR ($^1$H, CDCl$_3$): δ 7.80(d, 1H), 7.09(d, 1H), 6.93(d, 1H), 6.81(d, 1H), 6.77(dd, 1H), 6.53(s, 1H), 4.56(bs, 1H), 4.25 (m, 1H), 4.10(t, 2H), 3.79(s, 3H), 3.61(m, 3H), 2.97(dd, 1H), 2.27(s, 3H), 2.17(s, 3H), 1.21(d, 3H). MS(m/z): 419[MH]$^+$. |

-continued

| Cpd. No. | R | $R_{12}$ | Z | Analytical Data |
|---|---|---|---|---|
| 1-25 | 2-methyl-4-methoxyphenyl | H | (phenyl group) | NMR ($^1$H, DMSO-$d_6$): δ 7.79(s, 1H), 7.6(d, 1H), 7.43(t, 1H), 7.2(d, 2H), 7.02(bs, 1H), 6.89(d, 1H), 6.83(dd, 1H), 6.49(s, 1H), 3.85(t, 2H), 3.8(t, 2H), 3.77(s, 3H), 3.4(t, 2H), 3.2(t, 2H), 2.21(s, 6H). MS(m/z): 415[MH]$^+$. |
| 1-26 | 2-methyl-4-methoxyphenyl | H | (methylpyrazolyl group) | NMR ($^1$H, CDCl$_3$): δ 7.18(d, 1H); 6.9(d, 1H); 7.85(d, 1H); 6.77(m, 1H); 6.53(s, 2H); 6.43(s, 1H); 3.80(t, 2H); 3.75(s, 3H); 3.41(t, 2H); 3.3(s, 3H); 3.15(t, 2H); 2.34(s, 3H), 2.18(s, 3H), 2.17(s, 3H). MS(m/z): 418.2[MH]$^+$. |
| 1-27 | 2-methyl-4-difluoromethyloxyphenyl | H | (pyrazolyl group) | NMR ($^1$H, CDCl$_3$): δ 7.87(d, 1H), 7.30(dd, 1H), 7.08(d, 1H), 7.01(dd, 1H), 7.00(d, 1H), 6.64(s, 1H), 6.53(t, 1H), 4.66(s, 1H), 4.14(t, 2H), 3.92(t, 2H), 3.66(t, 2H), 3.51(t, 2H), 2.38(bs, 3H), 2.31(s, 3H). MS(m/z): 441[MH]+ |

$R_1$ is —CH$_3$;
$R_5$ is hydrogen;
$R_6$ is hydrogen,
$R_7$ is hydrogen;
D corresponds to —CR$_8$R$_9$;
G corresponds to —CR$_{10}$R$_{11}$;
$R_8$, $R_9$, $R_{10}$, $R_{11}$ are all hydrogen, except for example 1-24 where $R_{10}$ is a methyl group

Example 2

Synthesis of compounds of general formula (II)

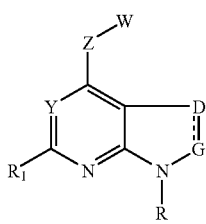

(II)

in which
Y   is —CR$_7$;
W   is a W9 derivative:

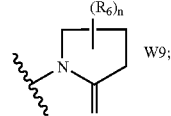

Z   is a pyrazolyl derivative

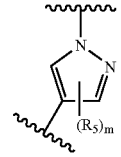

m   is an integer from 0 to 2;
n   is an integer from 0 to 6.

Example 2-1

1-{1-[1-(4-Methoxy-2-methylphenyl)-6-methyl-2,3-dihydro-1H-pyrrolo[2,3-b]pyridin-4-yl]-1H-pyrazol-3-yl}pyrrolidin-2-one In a sealed vial, at r.t., under N$_2$, are mixed together intermediate 5 (50 mg, 0.16 mmol), CuI (6 mg, 0.2 eq) and K$_2$CO$_3$ (46 mg, 2.1 eq). A solution of dodecane (14.5 μL, 0.4 eq), trans-cyclohexanediamine (11.5 μL, 0.6 eq) and intermediate 10 (30 mg, 1.2 eq) in anh. NMP (1.5 mL) was added and the reaction mixture was subjected to microwave irradiation (150° C.) for three cycles (5 min, 10 min, 15 min). It was then cooled down to r.t. and poured in EtOAc/H$_2$O. The phases were separated and the aqueous layer was extracted with EtOAc (2×10 mL). The combined organic extracts were dried over anh. Na$_2$SO$_4$, the solids were filtered and the solvent evaporated. The crude product was purified on a first SCX cartridge (cHex/EtOAc 9:1), a second SCX cartridge (CH$_2$Cl$_2$/MeOH 9:1) and finally preparative HPLC (Column: X Terra MS C18 5 um, 50×4.6 mm, Mobile phase: A: H2O+ 0.1% TFA.; B: CH3CN+0.1% TFA, Gradient: 10% (B) for 1 min, from 10% (B) to 90% (B) in 12 min, Flow rate: 1 ml/min, UV wavelength range: 200-400 nm, Mass range: 150-900 amu, Ionization: ES+) to give the title compound as a pale yellow solid (21 mg, 35%)

All the analytical data are set forth in the following Table 2-1 and in which:

| | |
|---|---|
| $R_1$ | is —CH$_3$; |
| $R_5$ | is hydrogen; |
| $R_6$ | is hydrogen, |

|   |   |
|---|---|
| $R_7$ | is hydrogen; |
| D | corresponds to —$CR_8R_9$; |
| G | corresponds to —$CR_{10}R_{11}$; |
| $R_8, R_9, R_{10}, R_{11}$ | are all hydrogen. |

| Cpd. No. | R | Analytical Data |
|---|---|---|
| 2-1 | 2-methyl-4-methoxy-phenyl | NMR($^1$H, DMSO): δ 8.35(d, 1H), 7.20(d, 1H), 6.95(d, 1H), 6.85(d, 1H), 6.75(m, 2H), 3.90(m, 4H), 3.70(s, 3H), 3.45(t, 2H), 2.50(m, 2H), 2.15(s, 3H), 2.10(m, 2H), 2.10(s, 3H). MS(m/z): 404[MH]$^+$ |

Example 3

Synthesis of compounds of general formula (II)

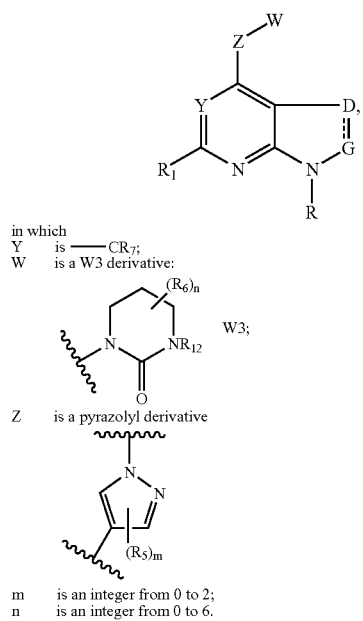

(II)

in which
Y   is ——$CR_7$;
W   is a W3 derivative:

W3;

Z   is a pyrazolyl derivative m   is an integer from 0 to 2;
n   is an integer from 0 to 6.

Example 3-1

1-{1-[1-(4-Methoxy-2-methylphenyl)-6-methyl-2,3-dihydro-1H-pyrrolo[2,3-b]pyridin-4-yl]-1H-pyrazol-3-yl}tetrahydropyrimidin-2(1H)-one In a sealed vial, at r.t., under $N_2$, are mixed together intermediate 5 (15 mg, 0.04 mmol), CuI (1.5 mg, 0.2 eq) and $K_2CO_3$ (11.6 mg, 2.1 eq). A solution of dodecane (2 μL, 0.2 eq), trans-cyclohexanediamine (2 μL, 0.3 eq) and intermediate 13 (8 mg, 1 eq) in anh. NMP (2 mL) was added and the reaction mixture was stirred at 130° C. for 6 hr. It was then cooled down to r.t. and poured in EtOAc/$H_2O$. The phases were separated and the aqueous layer was extracted with EtOAc (2×10 mL). The combined organic extracts were dried over anh. $Na_2SO_4$, the solids were filtered and the solvent evaporated The crude product was purified on an SCX cartridge (EtOAc/cHex 6:4, then 100% EtOAc, then, 5% MeOH/EtOAc) to give the title compound as a white solid (5.1 mg, 25%)

All the analytical data are set forth in the following Table 3-1 and in which:

|   |   |
|---|---|
| $R_1$ | is —$CH_3$; |
| $R_5$ | is hydrogen; |
| $R_6$ | is hydrogen; |
| $R_7$ | is hydrogen; |
| $R_{12}$ | is hydrogen; |
| D | corresponds to —$CR_8R_9$; |
| G | corresponds to —$CR_{10}R_{11}$; |
| $R_8, R_9, R_{10}, R_{11}$ | are all hydrogen. |

| Cpd. No. | R | Analytical Data |
|---|---|---|
| 3-1 | 2-methyl-4-methoxy-phenyl | NMR($^1$H, CDCl$_3$): δ 7.80(d, 1H), 7.2(d, 1H), 7.0(d, 1H), 6.80(d, 1H), 6.75(dd, 1H), 6.60(s, 1H), 4.95(bs, 1H), 4.05(dd, 2H), 3.90(t, 2H), 3.80(s, 3H), 3.45(t, 2H), 3.40(bm, 2H), 2.45(s, 3H), 2.25(s, 3H), 2.05(m, 2H). MS(m/z): 419[MH]$^+$ |

Example 4

Synthesis of compounds of general formula (II)

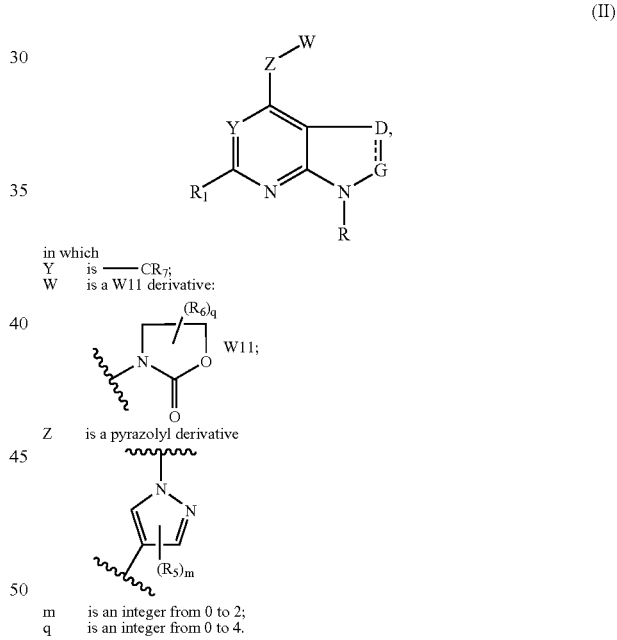

(II)

in which
Y   is ——$CR_7$;
W   is a W11 derivative:

W11;

Z   is a pyrazolyl derivative m   is an integer from 0 to 2;
q   is an integer from 0 to 4.

Example 4-1

3-(1-{6-Methyl-1-[2-methyl-4-(methyloxy)phenyl]-2,3-dihydro-1H-pyrrolo[2,3-b]pyridin-4-yl}-1H-pyrazol-3-yl)-1,3-oxazolidin-2-one To a vial under $N_2$ were added intermediate 5 (38 mg, 0.1 mmol), intermediate 16 (15 mg, 0.1 mmol), CuI (1.9 mg, 0.1 eq), (1R,2R)-diaminomethylcyclohexane (4.3 mg, 0.3 eq), $K_2CO_3$ (41 mg, 0.3 mmol) and anh. NMP (1 mL). The vial was sealed and the reaction mixture was stirred at 130° C. for 4 hr. It was poured into water/EtOAc. The phases were separated and the aqueous layer was further extracted with EtOAc (2×10 mL). The combined organic extracts were dried over anh. Na$_2$SO$_4$, the solids were filtered and the solvent evaporated. The residue was purified by flash chromatography (silica gel, EtOAc/cHex 1:1) to give the title compound as a white solid (20 mg, 49%).

All the analytical data are set forth in the following Table 4-1 and in which:

| | |
|---|---|
| R$_1$ | is —CH$_3$; |
| R$_5$ | is hydrogen; |
| R$_6$ | is hydrogen, |
| R$_7$ | is hydrogen; |
| D | corresponds to —CR$_8$R$_9$; |
| G | corresponds to —CR$_{10}$R$_{11}$; |
| R$_8$, R$_9$, R$_{10}$, R$_{11}$ | are all hydrogen. |

| Cpd. No. | R | Analytical Data |
|---|---|---|
| 4-1 | 2-methyl-4-methoxy-phenyl | NMR($^1$H, CDCl$_3$): δ 7.85(d, 1H), 7.16(d, 1H), 6.93(d, 1H), 6.81(d, 1H), 6.77(dd, 1H), 6.55(s, 1H), 4.54(t, 2H), 4.2(t, 2H), 3.87(t, 2H), 3.8(s, 3H), 3.44(t, 2H), 2.32(s, 3H), 2.24(s, 3H). MS(m/z): 406[MH]$^+$. |

Example 5

Synthesis of compounds of general formula (II)

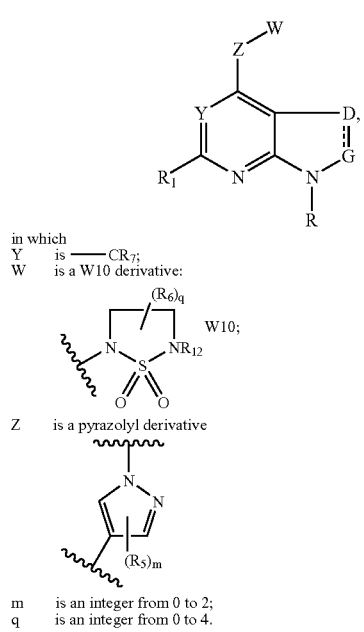

(II)

in which
Y is ——CR$_7$;
W is a W10 derivative:

W10;

Z is a pyrazolyl derivative m is an integer from 0 to 2;
q is an integer from 0 to 4.

Example 5-1

Methyl 5-(1-{6-methyl-1-[2-methyl-4-(methyloxy) phenyl]-2,3-dihydro-1H-pyrrolo[2,3-b]pyridin-4-yl}-1H-pyrazol-3-yl)-1,2,5-thiadiazolidine-2-carboxylate 1,1-dioxide)

To a vial under N$_2$ were added intermediate 21 (20 mg, 0.052 mmol), (methoxycarbonylsulfamoyl)triethylammonium hydroxide inner salt (40 mg, 3.2 eq) and anh. THF (1 mL). The reaction mixture was refluxed for 1 hr. It was cooled down to r.t. and diluted with CH$_2$Cl$_2$. 1N HCl was added and the phases were separated. The aqueous layer was further extracted with CH$_2$Cl$_2$ (3×10 mL). The combined organic extracts were concentrated and the residue was purified by flash chromatography (silica gel, cHex/EtOAc 7:3) to give the title compound as a white solid (8.2 mg, 32%).

Example 5-2

4-[3-(1,1-Dioxido-1,2,5-thiadiazolidin-2-yl)-1H-pyrazol-1-yl]-6-methyl-1-[2-methyl-4-(methyloxy) phenyl]-2,3-dihydro-1H-pyrrolo[2,3-b]pyridine To a solution of example 5-1 (7.2 mg, 0.0144 mmol) in anh. MeOH (1 mL) and anh. CH$_2$Cl$_2$ (2 mL), at r.t., under N$_2$, was added 25% NaOH (40 μL). The reaction mixture was stirred at r.t. for 30 min. It was then poured into sat.aq. NaHCO$_3$ and CH$_2$Cl$_2$ was added. The phases were separated and the aqueous layer was further extracted with CH$_2$Cl$_2$ (2×10 mL). The combined organic extracts were dried over anh. Na$_2$SO$_4$, the solids were filtered and the solvent evaporated to give the title compound (6.4 mg, quantitative yield) as a white solid.

All the analytical data are set forth in the following Table 5-1 and in which:

| | |
|---|---|
| R$_1$ | is —CH$_3$; |
| R$_5$ | is hydrogen; |
| R$_6$ | is hydrogen, |
| R$_7$ | is hydrogen; |
| D | corresponds to —CR$_8$R$_9$; |
| G | corresponds to —CR$_{10}$R$_{11}$; |
| R$_8$, R$_9$, R$_{10}$, R$_{11}$ | are all hydrogen. |

| Cpd. No. | R | R$_{12}$ | Analytical Data |
|---|---|---|---|
| 5-1 | 2-methyl-4-methoxy-phenyl | CO$_2$Me | NMR($^1$H, CDCl$_3$): δ 7.88(d, 1H), 7.17(d, 1H), 6.82(d, 1H), 6.77(dd, 1H), 6.51(s, 1H), 6.5(d, 1H), 4.1(bst, 4H), 3.95(s, 3H), 3.87(t, 2H), 3.81(s, 3H), 3.46(t, 2H), 2.32(s, 3H), 2.24(s, 3H). MS(m/z): 499[MH]$^+$ |
| 5-2 | 2-methyl-4-methoxy-phenyl | H | NMR($^1$H, DMSO-d$_6$): δ 8.37(d, 1H), 7.71(bs, 1H), 7.15(d, 1H), 6.84(d, 1H), 6.76(dd, 1H), 6.74(s, 1H), 6.31(d, 1H), 3.93(t, 2H), 3.82(t, 2H), 3.74(s, 3H), 3.50(t, 2H), 3.42(t, 2H), 2.16(s, 3H), 2.13(s, 3H). MS(m/z): 441[MH]$^+$ |

Example 6

Synthesis of compounds of general formula (II)

(II)

-continued in which
Y   is ——CR$_7$;
W   is a W12 derivative:

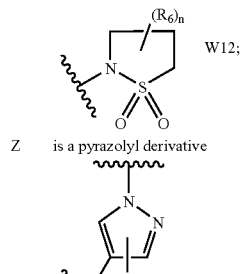

Z   is a pyrazolyl derivative m   is an integer from 0 to 2;
n   is an integer from 0 to 6.

Example 6-1

4-[3-(1,1-Dioxido-2-isothiazolidinyl)-1H-pyrazol-1-yl]-6-methyl-1-[2-methyl-4-(methyloxy)phenyl]-2,3-dihydro-1H-pyrrolo[2,3-b]pyridine Intermediate 22 (10 mg, 0.022 mmol) and POCl$_3$ (1 mL) were mixed together in a vial under N$_2$. The reaction mixture was refluxed for 1 hr. Sat.aq. NaHCO$_3$ was added until neutral pH and the mixture was partitioned between water and EtOAc. The two phases were separated and the aqueous layer was further extracted with EtOAc (3×10 mL). The combined organic extracts were concentrated and the residue was purified by flash chromatography (silica gel, cHex/EtOAc 1:1→EtOAc/sol. NH$_3$ in MeOH (0.5 M) 7:3) to give the title compound as a white solid (4.2 mg, 50%).

All the analytical data are set forth in the following Table 6-1 and in which:

| | | |
|---|---|---|
| | R$_1$ | is —CH$_3$; |
| | R$_5$ | is hydrogen; |
| | R$_6$ | is hydrogen, |
| | R$_7$ | is hydrogen; |
| | D | corresponds to —CR$_8$R$_9$; |
| | G | corresponds to —CR$_{10}$R$_{11}$; |
| | R$_8$, R$_9$, R$_{10}$, R$_{11}$ | are all hydrogen. |

| Cpd. No. | R | Analytical Data |
|---|---|---|
| 6-1 | 2-methyl-4-methoxy-phenyl | NMR($^1$H, CDCl$_3$): δ 7.84(d, 1H), 7.16(d, 1H), 6.82(d, 1H), 6.77(dd, 1H), 6.52(s, 1H), 6.51(d, 1H), 3.98(t, 2H), 3.87(t, 2H), 3.80(s, 3H), 3.46(m, 2H), 3.37(t, 2H), 2.57(m, 2H), 2.32(s, 3H), 2.23(s, 3H). IR(film, cm$^{-1}$): - MS(m/z): 439[M]$^+$. |

Example 7

Synthesis of compounds of general formula (II)

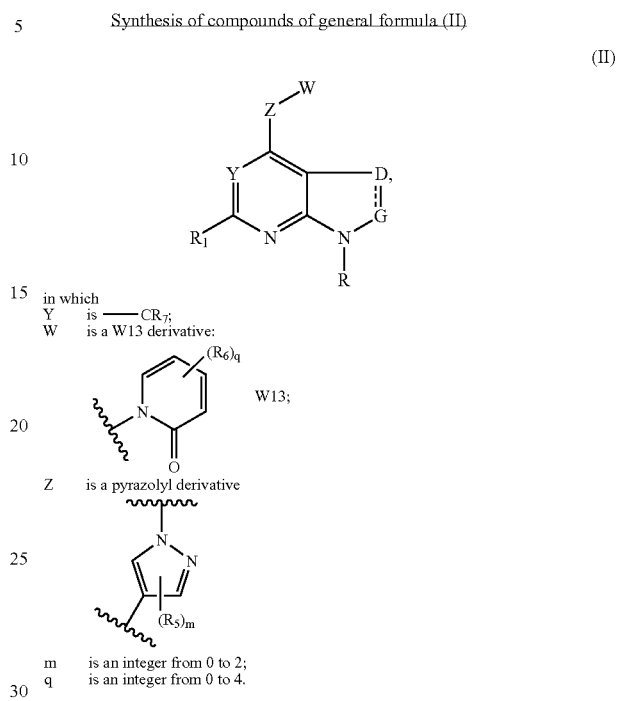

(II)

in which
Y   is ——CR$_7$;
W   is a W13 derivative:

Z   is a pyrazolyl derivative m   is an integer from 0 to 2;
q   is an integer from 0 to 4.

Example 7-1

3-Methyl-1-(1-{6-methyl-1-[2-methyl-4-(methyloxy)phenyl]-2,3-dihydro-1H-pyrrolo[2,3-b]pyridin-4-yl}-1H-pyrazol-3-yl)-2(1H)-pyridinone A solution of intermediate 5 (20 mg, 0.05 mmol), intermediate 26 (14 mg, 2 eq), CuI (10 mg, 1 eq), K$_2$CO$_3$ (15 mg, 2.1 eq) and N-N'-dimethyl trans-cyclohexanediamine (9 mg, 1 eq) in anh. NMP (1 mL) at r.t., was heated at 150° C. for 18 hr. Sat.aq. NH$_4$Cl (10 mL) was then added and the solution extracted with CH$_2$Cl$_2$ (25 mL). The organic layer was dried over anh. Na$_2$SO$_4$, the solids were filtered and the solvents evaporated in vacuo The crude compound thus obtained was purified by flash chromatography (silica gel, cHex/EtOAc 1:9) to give 5.5 mg (44%) of the title compound as a white solid.

All the analytical data are set forth in the following Table 7-1 and in which:

| | | |
|---|---|---|
| | R$_1$ | is —CH$_3$; |
| | R$_5$ | is hydrogen; |
| | R$_6$ | is hydrogen, |
| | R$_7$ | is hydrogen; |
| | D | corresponds to —CR$_8$R$_9$; |
| | G | corresponds to —CR$_{10}$R$_{11}$; |
| | R$_8$, R$_9$, R$_{10}$, R$_{11}$ | are all hydrogen. |

| Cpd. No. | R | Analytical Data |
|---|---|---|
| 7-1 | 2-methyl-4-methoxy-phenyl | NMR($^1$H, CDCl$_3$): δ 8.00(dd, 1H), 7.9(d, 1H), 7.3(m, 2H), 7.25(d, 1H), 6.8(m, 2H), 6.7(s, 1H), 6.2(t, 1H), 3.9(t, 2H), 3.4(t, 2H), 3.7(s, 3H), 2.4(s, 3H), 2.3(s, 3H), 2.25(s, 3H), MS(m/z): 428[MH]$^+$. |

Example 8

Synthesis of compounds of general formula (II)

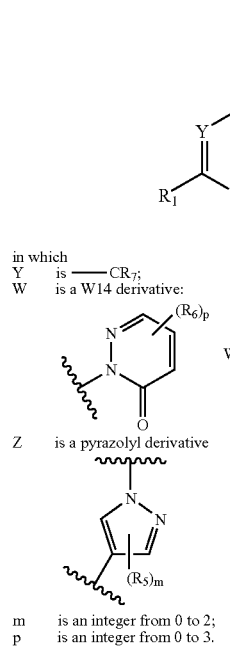

(II)

in which
Y is —CR$_7$;
W is a W14 derivative:

W14;

Z is a pyrazolyl derivative m is an integer from 0 to 2;
p is an integer from 0 to 3.

Example 8-1

2-(1-{6-Methyl-1-[2-methyl-4-(methyloxy)phenyl]-2,3-dihydro-1H-pyrrolo[2,3-b]pyridin-4-yl}-1H-pyrazol-3-yl)-3(2H)-pyridazinone A solution of intermediate 5 (25 mg, 0.06 mmol), intermediate 28 (20 mg, 2 eq), CuI (10 mg, 1 eq), K$_2$CO$_3$ (15 mg, 2.1 eq) and N-N'-dimethyl trans-cyclohexanediamine (9 mg, 1 eq) in anh. NMP (1 mL) was heated at 150° C. for 3 days. Sat.aq. NH$_4$Cl (10 mL) was then added and the solution extracted with CH$_2$Cl$_2$ (25 ml). The organic layer was dried over anh. Na$_2$SO$_4$, the solids were filtered and the solvents evaporated in vacuo. The crude compound thus obtained was purified by flash chromatography (silica gel, cHex/EtOAc 1:9) to give 6 mg (24%) of the title compound as a white solid.

All the analytical data are set forth in the following Table 8-1 and in which:

| | |
|---|---|
| R$_1$ | is —CH$_3$; |
| R$_5$ | is hydrogen; |
| R$_6$ | is hydrogen, |
| R$_7$ | is hydrogen; |
| D | corresponds to —CR$_8$R$_9$; |
| G | corresponds to —CR$_{10}$R$_{11}$; |
| R$_8$, R$_9$, R$_{10}$, R$_{11}$ | are all hydrogen. |

| Cpd. No. | R | Analytical Data |
|---|---|---|
| 8-1 | 2-methyl-4-methoxy-phenyl | NMR($^1$H, CDCl$_3$): δ 7.96(dd-d, 2H), 7.27(dd, 1H), 7.16(d, 1H), 6.98(d, 1H), 6.82(d, 1H), 6.77(dd, 1H), 6.64(s, 1H), 3.88(t, 2H), 3.8(s, 3H), 3.46(t, 2H), 2.33(s, 3H), 2.23(s, 3H). MS(m/z): 415[MH]$^+$. |

Example 9

Synthesis of compounds of general formula (II)

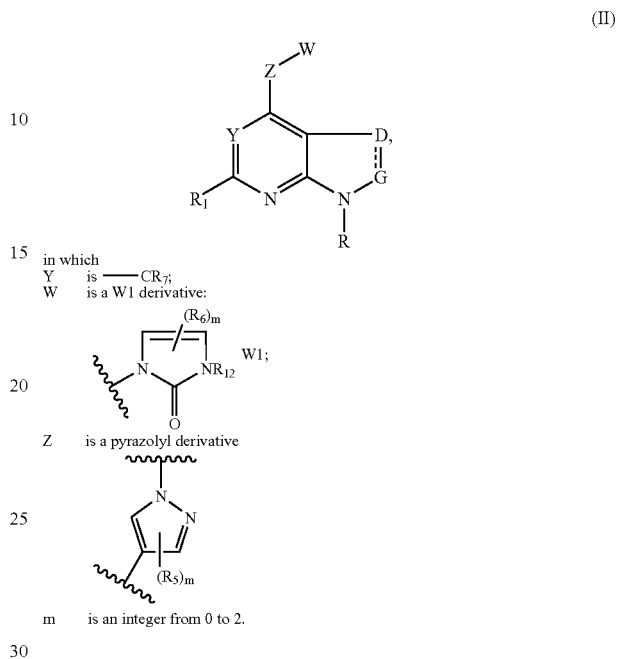

(II)

in which
Y is —CR$_7$;
W is a W1 derivative:

W1;

Z is a pyrazolyl derivative m is an integer from 0 to 2.

Example 9-1

1-(1-{6-Methyl-1-[2-methyl-4-(methyloxy)phenyl]-2,3-dihydro-1H-pyrrolo[2,3-b]pyridin-4-yl}-1H-pyrazol-3-yl)-1,3-dihydro-2H-imidazol-2-one To a solution of intermediate 24 (50 mg, 0.1 mmol), in anh. CH$_2$Cl$_2$ (2 mL) was added HCl 6N (200 µL). The reaction mixture was stirred at rt. for 45 min. It was then neutralized with 1M NaHCO$_3$ (1 mL) and the solvents were evaporated in vacuo. The crude compound thus obtained was purified by flash chromatography (silica gel, cHex/EtOAc 1:1) to give 18 mg (45%) of the title compound as a white solid.

All the analytical data are set forth in the following Table 9-1 and in which:

| | |
|---|---|
| R$_1$ | is —CH$_3$; |
| R$_5$ | is hydrogen; |
| R$_6$ | is hydrogen, |
| R$_7$ | is hydrogen; |
| R$_{12}$ | is hydrogen; |
| D | corresponds to —CR$_8$R$_9$; |
| G | corresponds to —CR$_{10}$R$_{11}$; |
| R$_8$, R$_9$, R$_{10}$, R$_{11}$ | are all hydrogen. |

| Cpd. No. | R | Analytical Data |
|---|---|---|
| 9-1 | 2-methyl-4-methoxy-phenyl | NMR($^1$H, CDCl$_3$): δ 7.85(d, 1H), 7.79(bs, 1H), 7.12(d, 1H), 7.03(d, 1H), 6.96(m, 1H), 6.76(d, 1H), 6.72(dd, 1H), 6.52(s, 1H), 6.33(m, 1H), 3.82(t, 2H), 3.74(s, 3H), 3.41(t, 2H), 3.27(s, 3H), 2.18(s, 3H). MS(m/z): 403[MH]$^+$. |

Example 10

Synthesis of compounds of general formula (II)

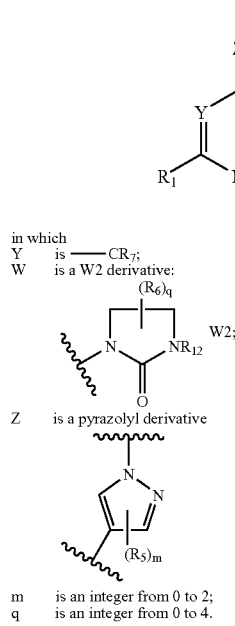
(II)

in which
Y    is ——CR₇;
W    is a W2 derivative:

(R₆)$_q$, W2;

Z    is a pyrazolyl derivative (R₅)$_m$ m    is an integer from 0 to 2;
q    is an integer from 0 to 4.

Example 10-1

1-(1-{6-Methyl-1-[2-methyl-4-(methyloxy)phenyl]-1H-pyrrolo[2,3-b]pyridin-4-yl}-1H-pyrazol-3-yl)-2-imidazolidinone To a solution of example 1 (90 mg, 0.223 mmol) in anh. CH$_2$Cl$_2$ (6 mL) at r.t., under N$_2$, was added DDQ (56 mg, 5 eq). The reaction mixture was stirred at r.t. for 24 hr. The solvent was evaporated in vacuo. The crude compound thus obtained was purified by flash chromatography (silica gel, cHex/EtOAc 1:1) to give 14.8 mg of a white solid, which was further purified by Mass Direct Autoprep (Fraction Lynks), affording the title compound as white solid (9 mg, 10%).

All the analytical data are set forth in the following Table 10-1 and in which:

|   |   |
|---|---|
| R$_1$ | is —CH$_3$; |
| R$_5$ | is hydrogen; |
| R$_6$ | is hydrogen, |
| R$_7$ | is hydrogen; |
| R$_{12}$ | is hydrogen; |
| D | corresponds to —CR$_8$; |
| G | corresponds to —CR$_{10}$; |
| D and G | are double bonded; |
| R$_8$, R$_{10}$ | are all hydrogen. |

| Cpd. No. | R | Analytical Data |
|---|---|---|
| 10-1 | 2-methyl-4-methoxy-phenyl | NMR($^1$H, CDCl3): 8.57(d, 1H), 7.42(d, 1H), 7.37(s, 1H), 7.21(d, 1H), 7.18(d, 1H), 7.09(bs, 1H), 6.97(d, 1H), 6.89(dd, 1H), 4.00(m, 2H), 3.81(s, 3H), 3.48(m, 2H), 2.46(s, 3H), 1.95(s, 3H)δ.<br>MS(m/z): 403[MH]$^+$. |

Example 11

Synthesis of compounds of general formula (II)

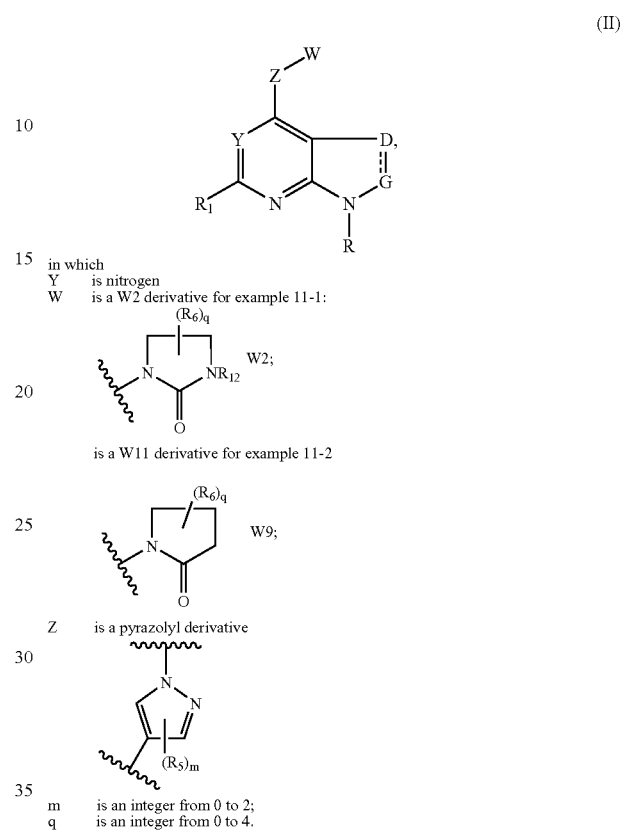
(II)

in which
Y    is nitrogen
W    is a W2 derivative for example 11-1:

(R₆)$_q$, W2;

is a W11 derivative for example 11-2

(R₆)$_q$, W9;

Z    is a pyrazolyl derivative (R₅)$_m$ m    is an integer from 0 to 2;
q    is an integer from 0 to 4.

Example 11-1

1-(1-{7-[2,4-bis(trifluoromethyl)phenyl]-2-methyl-6,7-dihydro-5H-pyrrolo[2,3-d]pyrimidin-4-yl}-1H-pyrazol-3-yl)-2-imidazolidinone To a solution of intermediate 8 (7 mg, 2 eq) in anh. DMF (3.5 mL), at r.t., under N$_2$, was added NaH 60%/oil (2 mg, 2 eq). The reaction mixture was stirred at r.t. for 20 min. A solution of intermediate 118 (8 mg, 0.021 mmol) in anh. DMF (3 mL) was added to the reaction mixture and it was heated at 80° C. for 5 hr. Water and EtOAc were added and the phases were separated. The aqueous layer was further extracted with EtOAc (2×10 mL). The combined organic extracts were dried over anh. Na$_2$SO$_4$, the solids were filtered and the solvent evaporated. The residue was purified on a MEGA Bond Elut silica cartridge (100% cHex→100% EtOAc) to give the title compound as a white solid (1.2 mg, 12%).

Example 11-2

1-{1-[7-(2,4-Dichlorophenyl)-2-methyl-6,7-dihydro-5H-pyrrolo[2,3-d]pyrimidin-4-yl]-1H-pyrazol-3-yl}-2-pyrrolidinone To a suspension of NaH 60%/oil (5 mg, 3.0 eq) in anh. DMF (1 mL) at r.t., under N$_2$, was added intermediate 10 (30 mg, 3 eq). The reaction mixture was stirred at 80° C. for 30 min. Intermediate 120 (20 mg, 0.064 mmol) was then added and the reaction mixture was heated at 100° C. for 5 h. It was then cooled down to r.t., poured into EtOAc, washed with sat.aq. NaCl (3×10 mL) and dried over anh. $Na_2SO_4$. The solid was filtered and the solvent evaporated. The crude product was purified by flash chromatography (silica gel, cHex/EtOAc 7:3) to give the title compound as white solid (10 mg, 35%).

All the analytical data are set forth in the following Table 11-1 and in which:

| | |
|---|---|
| $R_1$ | is —$CH_3$; |
| $R_5$ | is hydrogen; |
| $R_6$ | is hydrogen, |
| $R_{12}$ | is hydrogen; |
| D | corresponds to —$CR_8R_9$; |
| G | corresponds to —$CR_{10}R_{11}$; |
| $R_8, R_9, R_{10}, R_{11}$ | are all hydrogen. |

| Cpd. No. | R | W | Analytical Data |
|---|---|---|---|
| 11-1 | 2,4-bis-tri-fluoromethyl-phenyl | | NMR ($^1H$, $CDCl_3$): δ 8.43 (d, 1H), 7.94 (d, 1H), 7.83 (dd, 1H), 7.45 (d, 1H), 6.88 (d, 1H), 4.05 (t, 2H), 3.89 (t, 2H), 3.85 (t, 2H), 3.85 (t, 2H), 2.35 (s, 3H). MS (m/z): 498 $[MH]^+$. |
| 11-2 | 2,4-dichloro-phenyl | | NMR ($^1H$, $CDCl_3$): δ 8.50 (d, 1H), 7.47 (d, 1H), 7.34 (d, 1H), 7.29 (dd, 1H), 7.08 (d, 1H), 4.08 (m, 4H), 3.60 (t, 4H), 2.60 (t, 2H), 2.42 (s, 2H), 2.19 (t, 2H). MS (m/z): 429 $[MH]^+$. |

Example 12

CRF Binding Activity

CRF binding affinity has been determined in vitro by the compounds' ability to displace $^{125}$I-oCRF and $^{125}$I-Sauvagine for CRF1 and CRF2 SPA, respectively, from recombinant human CRF receptors expressed in Chinese Hamster Ovary (CHO) cell membranes. For membrane preparation, CHO cells from confluent T-flasks were collected in SPA buffer (HEPES/KOH 50 mM, EDTA 2 mM, $MgCl_2$ 10 mM, pH 7.4.) in 50 mL centrifuge tubes, homogenized with a Polytron and centrifuged (50,000 g for 5 min at 4° C.: Beckman centrifuge with JA20 rotor). The pellet was resuspended, homogenized and centrifuged as before.

The SPA experiment has been carried out in Optiplate by the addition of 100 μL the reagent mixture to 1 μL of compound dilution (100% DMSO solution) per well. The assay mixture was prepared by mixing SPA buffer, WGA SPA beads (2.5 mg/mL), BSA (1 mg/mL) and membranes (50 and 5 μg of protein/mL for CRF1 and CRF2 respectively) and 50 pM of radioligand.

The plate was incubated overnight (>18 hrs) at room temperature and read with the Packard Topcount with a WGA-SPA $^{125}$I counting protocol.

Example 13

CRF Functional Assay

Compounds of the invention were characterised in a functional assay for the determination of their inhibitory effect. Human CRF-CHO cells were stimulated with CRF and the receptor activation was evaluated by measuring the accumulation of cAMP.

CHO cells from a confluent T-flask were resuspended with culture medium without G418 and dispensed in a 96-well plate, 25,000 c/well, 100 μL/well and incubated overnight. After the incubation the medium was replaced with 100 μL of cAMP IBMX buffer warmed at 37° C. (5 mM KCl, 5 mM $NaHCO_3$, 154 mM NaCl, 5 mM HEPES, 2.3 mM $CaCl_2$, 1 mM $MgCl_2$, 1 g/L glucose, pH 7.4 additioned by 1 mg/mL BSA and 1 mM IBMX) and 1 μL of antagonist dilution in neat DMSO. After 10 additional minutes of incubation at 37° C. in a plate incubator without CO2, 1 μL of agonist dilution in neat DMSO was added. As before, the plate was incubated for 10 minutes and then cAMP cellular content was measured by using the Amersham RPA 538 kit.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular and preferred groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:

1. A compound which is 1-{1-[1-(4-Methoxy-2-methylphenyl)-6-methyl-2,3-dihydro-1H-pyrrolo[2,3-b]pyridin-4-yl]-1H-pyrazol-3-yl}imidazolidin-2-one or a pharmaceutically acceptable salt thereof.

2. A pharmaceutical composition comprising a therapeutically effective amount of a compound according to claim 1, or a pharmaceutically acceptable salt thereof, in admixture with one or more pharmaceutically acceptable carriers or excipients.

3. A pharmaceutical composition according to claim 2 wherein the pharmaceutical composition is formulated for oral administration.

4. A pharmaceutical composition according to claim 3 in the form of a tablet or capsule.

5. A pharmaceutical composition according to claim 4 in the form of a tablet.

6. A pharmaceutical composition according to claim 5 wherein the tablet is coated.

7. A pharmaceutical composition according to claim 3 formulated to give controlled release of 1-{1-[1-(4-Methoxy-2-methylphenyl)-6-methyl-2,3-dihydro-1H-pyrrolo[2,3-b]pyridin-4-yl]-1H-pyrazol-3-yl} imidazolidin-2-one or a pharmaceutically acceptable salt thereof.

8. A pharmaceutical composition according to claim 3 wherein at least one pharmaceutically acceptable excipient is selected from the group consisting of binding agents, fillers, lubricants, disintegrants, wetting agents, suspending agents, emulsifling agents, non-aqueous vehicles, preservatives, buffer salts, flavouring agents, coloring agents, and sweetening agents.

9. A pharmaceutical composition according to claim 8 wherein at least one pharmaceutically acceptable excipient is selected from the group consisting of binding agents, fillers, lubricants, disintegrants, and wetting agents.

10. A compound which is 1-{1-[1-(4-Methoxy-2-methylphenyl)-6-methyl-2,3-dihydro-1H-pyrrolo[2,3-b]pyridin-4-yl]-1H-pyrazol-3-yl} imidazolidin-2-one.

11. A pharmaceutical composition comprising a therapeutically effective amount of a compound according to claim 10 in admixture with one or more pharmaceutically acceptable carriers or excipients.

12. A pharmaceutical composition according to claim 11 wherein the pharmaceutical composition is formulated for oral administration.

13. A pharmaceutical composition according to claim 12 in the form of a tablet or capsule.

14. A pharmaceutical composition according to claim 13 in the form of a tablet.

15. A pharmaceutical composition according to claim 14 wherein the tablet is coated.

16. A pharmaceutical composition according to claim 12 formulated to give controlled release of 1-{1-[1-(4-Methoxy-2-methylphenyl)-6-methyl-2,3-dihydro-1H-pyrrolo [2,3-b]pyridin-4-yl]-1H-pyrazol-3-yl} imidazolidin-2-one.

17. A pharmaceutical composition according to claim 12 wherein at least one pharmaceutically acceptable excipient is selected from the group consisting of binding agents, fillers, lubricants, disintegrants, wetting agents, suspending agents, emulsifying agents, non-aqueous vehicles, preservatives, buffer salts, flavouring agents, coloring agents, and sweetening agents.

18. A pharmaceutical composition according to claim 17 wherein at least one pharmaceutically acceptable excipient is selected from the group consisting of binding agents, fillers, lubricants, disintegrants, and wetting agents.

* * * * *